US008206724B2

(12) United States Patent
Johnston et al.

(10) Patent No.: US 8,206,724 B2
(45) Date of Patent: Jun. 26, 2012

(54) METHOD AND COMPOSITIONS FOR VACCINATION COMPRISING NUCLEIC ACID AND/OR POLYPEPTIDE SEQUENCE OF CHLAMYDIA

(75) Inventors: Stephen A. Johnston, Tempe, AZ (US); Katherine Stemke-Hale, Houston, TX (US); Kathryn F. Sykes, Tempe, FL (US); Bernhard Kaltenboeck, Auburn, AL (US)

(73) Assignees: Auburn University, Auburn, AL (US); Board of Regents, The University of Texas System, Austin, TX (US)

( * ) Notice: Subject to any disclaimer, the term of this patent is extended or adjusted under 35 U.S.C. 154(b) by 785 days.

(21) Appl. No.: 11/788,692

(22) Filed: Apr. 19, 2007

(65) Prior Publication Data

US 2008/0025998 A1 Jan. 31, 2008

Related U.S. Application Data

(63) Continuation-in-part of application No. 10/023,437, filed on Dec. 17, 2001, now Pat. No. 7,811,592.

(60) Provisional application No. 60/255,839, filed on Dec. 15, 2000.

(51) Int. Cl.

| | |
|---|---|
| *A61K 39/118* | (2006.01) |
| *A61K 39/38* | (2006.01) |
| *A61K 39/02* | (2006.01) |
| *A61K 38/00* | (2006.01) |

(52) U.S. Cl. ............... 424/263.1; 424/184.1; 424/190.1; 530/300; 530/324

(58) Field of Classification Search ........................ None
See application file for complete search history.

(56) References Cited

U.S. PATENT DOCUMENTS

| | | | |
|---|---|---|---|
| 5,212,062 | A | 5/1993 | Daniels et al. |
| 5,989,553 | A | 11/1999 | Johnston et al. |
| 6,559,294 | B1 | 5/2003 | Graffais et al. |

FOREIGN PATENT DOCUMENTS

| | | |
|---|---|---|
| WO | WO9928475 | 6/1999 |
| WO | WO9953948 | 10/1999 |
| WO | WO02053588 | 7/2002 |

OTHER PUBLICATIONS

Greenspan et al. (Nature Biotechnology 7: 936-937, 1999).*
Bowie et al (Science, 1990, 257:1306-1310).*
Kaltenboeck et al (FASE B Journal, Apr. 20, 2000, vol. 14, No. 6, p. A1130, meeting May 12-16, 2000).*
Kaltenboeck et al (FASE B Journal, Apr. 20, 2000, vol. 14, No. 6, p. A1130, meeting May 12-16, 2000)(Abstract only).*
Shewen (Can Vet. J. 21:2-11, Jan. 1980).*
Sato et al (Science, vol. 273, Jul. 19, 1996, p. 352-354).*
McHenry (2003) "Chromosomal replicases as asymmetric dimers: studies and subunit arrangement and functional consequences," Molecular Microbiology 49(5), p. 1157-1185.
Curnow et al. (1997) "Glu-tRNAgin amidotransferase: A novel heterotrimeric enzyme required for correct decoding of glutamine codons during translation," Proc. Natl. Acad. Sci. vol. 94, pp. 11819-11826.
Racznjak et al. (2001) "A Single Amidotransferase Forms Asparaginyl-tRNA and Glutaminyl-tRNA in Chalmydia trachomatis," J. Biological Chem. 49 (276) pp. 45862-45867.
Kaltenboeck et al. Poster, "Fully Protective Vaccine Candidate Genes of Chlamydia Psittaci Identified by Random Expression Library Immunization,", Apr. 2000.
Kaltenboeck et al. (2000) FASEB Journal Apr. 2000, vol. 14, No. 6, pp. A1130, meetings held May 12-16, 2000 (Abstract).
Creighton, Thomas E. (1984) Proteins: Structures and Molecular Properties.
Creighton. Thomas E. (1989) Protein Structure: A Practical Approach.
Nosoh, Y et al. (1991) Protein Stability and Stabilization through Protein Engineering.

* cited by examiner

*Primary Examiner* — Vanessa L. Ford
(74) *Attorney, Agent, or Firm* — Andrus, Sceales, Starke & Sawall, LLP

(57) ABSTRACT

The instant invention relates to antigens and nucleic acids encoding such antigens obtainable by screening a *Chlamydia* genome. In more specific aspects, the invention relates to methods of isolating such antigens and nucleic acids and to methods of using such isolated antigens for producing immune responses. The ability of an antigen to produce an immune response may be employed in vaccination or antibody preparation techniques.

15 Claims, 8 Drawing Sheets

*Chlamydia psittaci* Addition Experiments

FIG. 7

METHOD AND COMPOSITIONS FOR VACCINATION COMPRISING NUCLEIC ACID AND/OR POLYPEPTIDE SEQUENCE OF CHLAMYDIA

The present application is a Continuation-in-Part of application Ser. No. 10/023,437, filed Dec. 17, 2001, which claims priority to U.S. Provisional Patent Application Ser. No. 60/225,839 filed on Dec. 15, 2000. The entire text of the above-referenced disclosure is specifically incorporated herein by reference without disclaimer.

The government owns rights in the present invention pursuant to DARPA grant number MDA 972-97-1-0013.

BACKGROUND OF THE INVENTION

1. Field of the Invention

The present invention relates generally to the files of immunology, bacteriology and molecular biology. More particularly, the invention relates to methods for screening and obtaining vaccines generated from the administration of expression libraries constructed from a *Chlamydia psittaci* geonome or corresponding homologs from other *Chlamydia* species. In particular embodiments, it concerns methods and compositions for the vaccination of vertebrate animals against *Chlamydia* bacterial infections, wherein vaccination of the animal is via a protein or gene derived from part or all of the genes validated as vaccines.

2. Descriptions of Related Art

Intracelluar bacteria of the genus *Chlamydia* are important pathogens in both man and vertebrate animals, causing blindness in man, sexually transmitted disease, and community-acquired pneumonia, and most likely act as co-factors in atherosclerotic plaque formation in human coronary heart disease.

Ubiquitous *Chlamydia* (C) *psittaci* infections in cattle cause mastitis, infertility and abortion. A primary economic impact of *Chlamydia* in a dairy cattle is the loss of milk production and quality. Serological evidence for infection with ruminant *Chlamydia psittaci* is found in virtually all cattle (Kaltenbock et al., 1997). These infections typically do not cause overt signs of disease, but under stress the host animal may elicit transient inflammation of the mammary gland and uterus. These stress-related herd health problems, while not clinically pronounced, result in major losses for animal agriculture due to reduced output and quality of animal products like milk.

Most existing vaccines for the treatment of bacterial infections are composed of live/attenuated or killed pathogens (Babiuk, 1999). Live/attenuated vaccines present the risk of residual, or reacquisition of, pathogenicity, and are associated with a high cost of production. In addition, efficacious live/attenuated vaccines cannot be developed against may pathogens, or are impractical to produce. Killed pathogens typically have less utility than live/attenuated vaccines, as they are not usually effective in eliciting cellular immune responses. An alternative is subunit vaccines that consist of one or a few proteins of the pathogen (Babiuk, 1999; Ellis, 1999). The proteins being developed for these vaccines are typically based on a dominant image response in infected hosts, and/or on surmised importance in the disease process. Due to the high genetic complexity of bacteria or protozoa, the empirical approach to identify these proteins often requires extensive research on the pathogen's biology and produces a small, biased set of potential vaccine candidates. However, this is currently the only practical method when proteins are the commodity for testing a vaccine.

The development of genetic (DNA) immunization (Tang et al., 1992) not only offers a new method of vaccine delivery, but also enables a new, unbiased, approach to vaccine discovery. The inventors have proposed that the whole genome of a pathogen could be searched for protein vaccine candidates by directly assessing protection from challenge, termed expression library immunization (ELI) (U.S. Pat. No. 5,703,057, specifically incorporated herein by reference). It involves making an expression library representing the whole genome of the pathogen in a genetic immunization vector. The library is subdivided into smaller groups, and DNA from each library is used to vaccinate animals that are subsequently challenged. The advantage of this approach is that all of the potentially protective genes could be discovered and used in any useful combination to reconstitute a vaccine devoid of non-protective, immunopathological, or immunosuppressive antigens. The potential of ELI was demonstrated in a murine *Mycoplasma pulmonis* infection, against which random *M. pulmonis* libraries were protective (Barry et al., 1995). Since then, others have reported on protective libraries (Brayton et al., 1998; Piedrafita et al., 1999), but the reduction of these libraries to individual genes has not been demonstrated.

As described above, the widespread human and animal infections by the genus *Chlamydia* represents a particular challenge for vaccinology. *Chlamydia psittaci* infections n cattle cause mastitis, infertility, and abortion. A primary economic impact of *Chlamydia* in dairy cattle is the loss of milk production and quality. Thus, an effective vaccine against *Chlamydia* bacterial infections in cattle would be of great economic importance. However, there presently have been no effective vaccines developed against any *Chlamydia.*

SUMMARY OF THE INVENTION

The present invention overcomes these difficulties and problems in the art and provides for methods of immunization using *Chlamydia* antigens and polynucleotides. The instant invention relates to antigens and nucleic acids encoding such antigens obtainable by screening a *Chlamydia* genome. Inn more specific aspects, the invention relates to methods of isolating such antigens and nucleic acids and to methods of using such isolated antigens for producing immune responses. The ability of an antigen to produce an immune response may be employed in vaccination or antibody preparation techniques.

In some embodiments, the invention relates to isolated polynucleotides having a region that comprises a sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:24, SEQ ID NO:26, SEQ ID NO:28, SEQ ID NO:30, SEQ ID ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:50, SEQ ID NO:50, SEQ ID NO:52, SEQ ID NO:58, SEQ ID NO:60, SEQ ID NO:62, SEQ ID NO: 64, SEQ ID NO: 66, or SEQ ID NO:68 a complement of any of these sequences, or fragments thereof, or sequences closely related to these sequences. In some more specific embodiments, the invention relates to such polynucleotides comprising a region having a sequence comprising at least 17, 20, 25, 30, 35, 40, 45, 50, 60, 70, 80, 90, 100, 125, 150, 200, or more contiguous nucleotides in common with at least one of SEQ ID NO:6, SEQ ID NO:8, SEQ ID NO: 10, SEQ ID NO:12, SEQ ID NO:14, SEQ ID NO:16, SEQ ID NO:18, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:58, SEQ ID NO:60, SEQ ID NO:62, SEQ ID NO:64, SEQ ID NO:66, or SEQ ID NO:68 or its complement. Of course, such polynucleotides may comprise a region having all nucleotides in common with at least on of SEQ ID NO:6, SEQ ID NO:8, SEQ ID NO:10, SEQ ID NO:12, SEQ ID NO:14, SEQ ID NO:16, SEQ ID NO:18, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:58, SEQ ID NO:60, SEQ ID NO:62, SEQ ID NO:64, SEQ ID NO:66, or SEQ ID NO:68 or its compliment.

In another aspect, the invention relates to polypeptides having sequences of SEQ ID NO:7, SEQ ID NO:9, SEQ ID NO:11, SEQ ID NO:13, SEQ ID NO:15, SEQ ID NO:17, SEQ ID NO:19, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or an antigenic fragment thereof, or sequences closely related to these these sequences. The antibodies may be polyclonal or monoclonal and produced by methods known in the art.

The invention contemplates vaccines comprising: (a) a pharmaceutically acceptable carrier, and (b) at least one polynucleotide having a *Chlamydia* sequence. In presently preferred embodiments, the at least one polynucleotide has a *Chlamydia psittaci, Chlamydia pneumoniae, Chlamydia trachomatis*, or *Chlamydia pecorum* sequence. In some specific embodiments at least one polynucleotide has a *Chlamydia psittaci* or *Chlamydia pneumonia* sequence.

The at least one polynucleotide may be isolated from a *Chlamydia* genomic DNA expression library but it need not be. For example, the polynucleotide may also be a sequence form one species that is determined to be protective based on the protective ability of a homologous sequence in another species. For example, the polynucleotide could be a *Chlamydia pneumonia* sequence that was determined to be protective after analysis of the *Chlamydia pneumonia* genomic sequence for homologues of *Chlamydia psittaci* antigens that had previously been shown to be protective. As discussed below, the polynucleotides need not be of natural origin, or to encode an antigen that is precisely a naturally occurring *Chlamydia* antigen. It is anticipated that polynucleotides and antigens within the scope of this invention my be synthetic and/or engineering to mimic, or improve upon, naturally occurring polynucleotides and still be useful in the invention.

In some embodiments, the at least one polynucleotide has a sequence isolated from *Chlamydia psittaci*, for example, a sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:58, or SEQ ID NO:60, or fragment thereof, or sequences closely related to these to these sequences. In more specific such embodiments, the at least one polynucleotide has a sequence of SEQ ID NO:6, SEQ ID NO:8, SEQ ID NO:10, SEQ ID NO:12, SEQ ID NO:14, SEQ ID NO:16, SEQ ID NO:20, SEQ ID NO:20, SEQ ID NO:22, SEQ ID NO:24, or SEQ ID NO:26, or fragment thereof, or sequences closely related to these sequences.

In even more specific embodiments, the at least one polynucleotide has a sequence of SEQ ID NO:6, SEQ ID NO:10, SEQ ID NO:14, SEQ ID NO:20, or SEQ ID NO:24.

In some embodiments, the polynucleotide encodes an antigen having a sequence of SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69; or antigenic fragment thereof, or sequences closely related to these sequences.

In many embodiments, the polynucleotide is comprised in a genetic immunization vector. Such a vector may, but need not comprise a gene encoding a mouse ubiquitin fusion polypeptide. The vector, in some preferred embodiments, will comprise a promoter operable in eukaryotic cells for example, but not limited to a CMV promoter. Such promoters are well known to those of skill in the art. In some embodiments, the polynucleotide is comprised in a viral expression vector, for example, but not limited to, a vector selected from the group consisting of adenovirus, adeno-associated virus, retrovirus and herpes-simplex virus.

The vaccines of the invention may comprise multiple polynucleotide sequences from one or more *Chlamydia* species. In some embodiments, the vaccine will comprise at least a first polynucleotide and the second polynucleotide having a sequence, wherein the first polynucleotide and the second polynucleotide have different sequences. In some more specific embodiments, the first polynucleotide may first polynucleotide may have a sequence of SEQ ID NO:50.

The present invention also involves vaccines comprising: (a) a pharmaceutically acceptable carrier; and (b) at least one *Chlamydia* antigen. The at least one *Chlamydia* antigen can be a *Chlamydia psittaci, Chlamydia pneumoniae, Chlamydia trachomatis*, or *Chlamydia pecorum* antigen or an antigen of any other *Chlamydia* species. In some cases, the at least one *Chlamydia* antigen has a sequence of SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69 or antigenic fragment thereof, or sequences closely related to these sequences. In some specific embodiments, the at least one *Chlamydia* antigen has a sequence of SEQ ID NO:7, SEQ ID NO:9, SEQ ID NO:11, SEQ ID NO:13, SEQ ID NO:15, SEQ ID NO:17, SEQ ID NO:21, SEQ ID NO:23, SEQ ID NO:25, or SEQ ID NO:27, or an antigenic fragment thereof, or sequences closely related to these sequences. In even more specific embodiments, the at least one *Chlamydia* antigen has a sequence of SEQ ID NO:7, SEQ ID NO:11, SEQ ID NO:15, SEQ ID NO:21, or SEQ ID NO:25.

The invention also relates to methods of immunizing an animal comprising providing to the animal at least one *Chlamydia* antigen, or antigenic fragment thereof, in an mount effective to induce an immune response. Again, the at least one *Chlamydia* antigen can be of *Chlamydia psittaci, Chlamydia pneumoniae, Chlamydia trachomatis, Chlamydia pecorum*, or any other *Chlamydia* species. In some cases, the at least one *Chlamydia* antigen is a *Chlamydia psittaci* antigen, while in others it will not be. In further examples the *Chlamydia pneumoniae* antigens are comprises of SEQ ID NO:63; SEQ ID NO:65; SEQ ID NO:675; SEQ ID NO:69. As discussed above, and described in detail below, the *Chlamydia* antigens useful in the antigens useful in the invention need not be native antigens. Rather, these antigens may have sequences that have been modified in any number of ways know to these of skill in the art, so long as they result in or aid in an antigenic response.

In some embodiments of the invention, the provision of the at least one *Chlamydia* antigen comprises: (a) preparing cloned expression library from fragmented genomic DNA, cDNA or sequenced genes of *Chlamydia*; (b) administering at least one clone of the library in a pharmaceutically acceptable carrier into the animal; and (c) expressing at least one *Chlamydia* antigen in the animal. The expression library may comprise at least one or more polynucleotides having a sequence of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:56, SEQ ID NO:58, or SEQ ID NO:60, SEQ ID NO:62; SEQ ID NO:64; SEQ ID NO:66; or SEQ ID NO:68; or fragment thereof, or sequences closely related to these sequences. The expression library may be cloned in a genetic immunization vector, such as a vector of SEQ ID NO:1, or any other suitable vector. The vector may comprise a gene encoding a mouse ubiquitin fusion polypeptide designed to link the expression library polynucleotides to the ubiquitin gene. The vector may comprise a promoter operable in eukaryotic cells for example a CMV promoter, or any other suitable promoter. In such methods, the polynucleotide may be administered by a intramuscular injection or epidermal injection. The polynucleotide may likewise be administered by intravenous, subcutaneous, intralesional, intraperitoneal, oral or inhaled routes of administration. In some specific, exemplary embodiments, the administration may be via intramuscular injection of at least 1.0 μg to 200 μg of the polynucleotide. In other exemplary embodiments, administration may be epidermal injection of at least 0.001 μg to 5.0 μg of the polynucleotide. In some cases, a second administration, for second administration, for example an intramuscular injection and/or epidermal injection, may administered at least about three weeks after the first administration. In these methods, the polynucleotide may be, but need not be, cloned into viral expression vector selected from the group consisting of adenovirus, herpes-simple virus, retrovirus and adeno-associated virus. The polynucleotide may also be administered in any other method disclosed here or known to those of skill in the art.

In some embodiments, the provision of the *Chlamydia* antigen(s) may comprise: (a) preparing a pharmaceutical composition comprising at least one polynucleotide encoding a *Chlamydia* antigen or fragment thereof; (b) administering one or more clones of the library in a pharmaceutically acceptable carrier into the animal; and (c) expressing one or more *Chlamydia* antigens in the animal. The one or more polynucleotides can be comprised in one or more expression vectors, as described above and elsewhere in this specification.

Alternatively, the provision of the *Chlamydia* antigen(s) may comprise: (a) preparing a pharmaceutical composition of at least one *Chlamydia* antigen or an antigenic fragment thereof; and (b) administering the at least one antigen or fragment into the animal. The antigen(s) may be administered by a frist intramuscular injection, intravenous injection, parenteral injection, epidermal injection, inhalation or oral route.

In preferred embodiments of the invention, the animal is a mammal. In some cases the mammal is a bovine, in others, the mammal is a human.

In some embodiments, these methods may induce an immune response against *Chlamydia psittaci*. Alternatively, these methods may be practiced in order to induce an immune response against *Chlamydia* species other than *Chlamydia psittaci*, for example, but not limited to, *Chlamydia pneumoniae, Chlamydia trachomatis*, and/or *Chlamydia pecorum*. In some embodiments, these methods may be employed to induce an immune response against a non-Chlamydia infection or other disease.

These methods may comprise administering to the animal an antigen or antigenic fragment from a *Chlamydia* species other than *Chlamydia psittaci*. Also, these methods may comprise administering to the animal an antigen or antigenic fragment from a non-Chlamydia species.

This specification discusses methods of obtaining polynucleotide sequences effective for generating an immune response against the genus *Chlamydia* is a non-human animal comprising: (a) preparing a cloned expression library from fragmented genomic DNA of the genus *Chlamydia*; (b) administering one or more clones of the library in a pharmaceutically acceptable carrier into the animal in an amount effective to induce an immune response; and (c) selecting from the library the polynucleotide sequences that induce a immune response, where in the immune response in the animal is protective against *Chlamydia* infection. Such methods may further comprise testing the animal for immune resistance against a *Chlamydia* bacterial infection by challenging the animal with *Chlamydia*. In some cases, the genomic DNA has been fragmented physically or by restriction enzymes, for example, but not limited to, fragments that average about 200-1000 base pairs in length. In some cases, each clone in the library may comprise a gene encoding a mouse ubiquitin fusion polypeptide designed to link the expression library polynucleotides to the ubiquitin gene, but is not required in all cases. In some cases, the library may comprise about $1 \times 10^3$ to about $1 \times 10^6$ clones; in more specific cases, the library could have $1 \times 10^5$ clones. In some preferred methods, about 0.01 μg to about 200 μg of DNA, from the clones is administered into the animal. in some situations the genomic DNA, cDNA or sequenced gene is introduced by intramuscular injection or epidermal injection. In some versions of these protocols, the cloned expression library further comprises a promoter operably linked to the DNA that permits expression in a vertebrate animal cell.

The application also discloses methods of preparing antigens that confer protection against infection in a vertebrate animal comprising the steps of: (a) preparing a cloned expression library from fragmented genomic DNA of the genus *Chlamydia*; (b) administering one or more clones of the library in a pharmaceutically acceptable carrier into the animal in an amount effective to induce an immune response; (c) selecting from the library the polynucleotide sequences that induce an immune response and expressing the polynucleotide sequences in cell culture; and (d) purifying the polypeptide(s) expressed in the cell culture. Often, these methods further comprise testing the animal for immune resistance against infection by challenging the animal with one or more *Chlamydia* or other pathogens.

The invention relates to methods of preparing antibodies against *Chlamydia* antigen comprising the steps of: (a) identifying a *Chlamydia* antigen that confers immune resistance against *Chlamydia* bacterial infection when challenged with the *Chlamydia* species in which the antigen was prepared; (b) generating an immune response in a vertebrate animal with the antigen identified in step (a); and (c) obtaining antibodies produced in the animal.

The invention also relates to methods for assaying for the presence of *Chlamydia* infection in a vertebrate animal comprising: (a) obtaining an antibody directed against a *Chlamydia* antigen; (b) obtaining a sample from the animal; (c) admixing the antibody with the sample; and (d) assaying the sample for antigen-antibody binding, wherein the antigen-antibody binding indicates *Chlamydia* infection in the animal. In some cases, the antibody directed against the antigen is further defined as a polyclonal antibody. In others, the antibody directed against the antigen is further defined as a monoclonal antibody. In some embodiments, the *Chlamydia* antigen has a sequence of SEQ ID NO: 7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, SEQ ID NO:31, SEQ ID NO:33, SEQ ID NO:35, SEQ ID NO:37, SEQ ID NO:39, SEQ ID NO:41, SEQ ID NO:43, SEQ ID NO:45, SEQ ID NO:47, SEQ ID NO:49, SEQ ID NO:51, SEQ ID NO:53, SEQ ID NO:55, SEQ ID NO:57, SEQ ID NO:59, SEQ ID NO:61, SEQ ID NO:63, SEQ ID NO:65, SEQ ID NO:67, or SEQ ID NO:69; or fragment NO:69; or fragment thereof, or sequences closely related to these sequences. The assaying the sample for antigen-antibody binding may be by precipitation reaction, radioimmunoassay, ELISA, Western blot, immunofluorescence, or any other method known to those of skill in the art.

The invention also relates to kits for assaying a *Chlamydia* infection comprising, in a suitable container: (a) a pharmaceutically acceptable carrier; and (b) an antibody directed against a *Chlamydia* antigen.

The invention further relates to methods assaying for the presence of a *Chlamydia* infection in an animal comprising: (a) obtaining an oligonucleotide probe comprising a sequence comprised within one of SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, SEQ ID NO:54, SEQ ID NO:56, SEQ ID NO:56, SEQ ID NO:58, or SEQ ID NO:60, SEQ ID NO:62; SEQ ID NO:64; SEQ ID NO:66; or SEQ ID NO:68; or a complement thereof; and (b) employing the probe in PCR or other detection protocol.

As used herein the specification, "a" or "an" may mean one or more. As used herein, when used in conjunction with the word "comprising", the words "a" or "an" may mean one or more than one. As used herein "another" may mean at least a second or more.

As used herein "plurality" means more than one. In certain specific aspects, a plurality may mean 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 55, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 400, 500, 750, 1,000, 2,000, 3,000, 4,000, 5,000, 7,500, 10,000, 15,000, 20,000, 15,000, 20,000, 30,000, 40,000, 50,000, 60,000, 70,000, 80,000, 90,000, 100,000, 125,000, 150,000, 200,000 or more and any integer derivable therein, and any range derivable therein.

As used herein, "any integer derivable therein" means a integer between the numbers described in the specification, and "any range derivable therein" means any range selected from such numbers or integers.

As used herein, a "fragment" refers to a sequence having or having at least 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 890, 900, 910, 920, 930, 940, 950, 960, 970, 980, 990, 1000 or more contiguous residues of the recited SEQ ID NOS, but less than the full-length of the SEQ. ID. NOS. It is contemplated that the definition of "fragment" can be applied to amino acid and nucleic acid fragments.

As used herein, an "antigenic fragment" refers to a fragment, as defined above, that can elicit an immune response in an animal.

Reference to a sequence in an organism, such as *Chlamydia* sequence" refers to a segment of contiguous residues that is unique to that organism or that constitutes a fragment (or full-length region(s)) found in that organism (either amino acid or nucleic acid).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7 Protection data from DNA pools. CP1-6 is a negative pool from round 1. To test whether a single protective gene could be detected in a negative pool, 25 ng of either CP4 #4 or CP4 #11 was added to 50 µg of CP1-6.

DESCRIPTION OF ILLUSTRATIVE EMBODIMENTS

Figure 1:
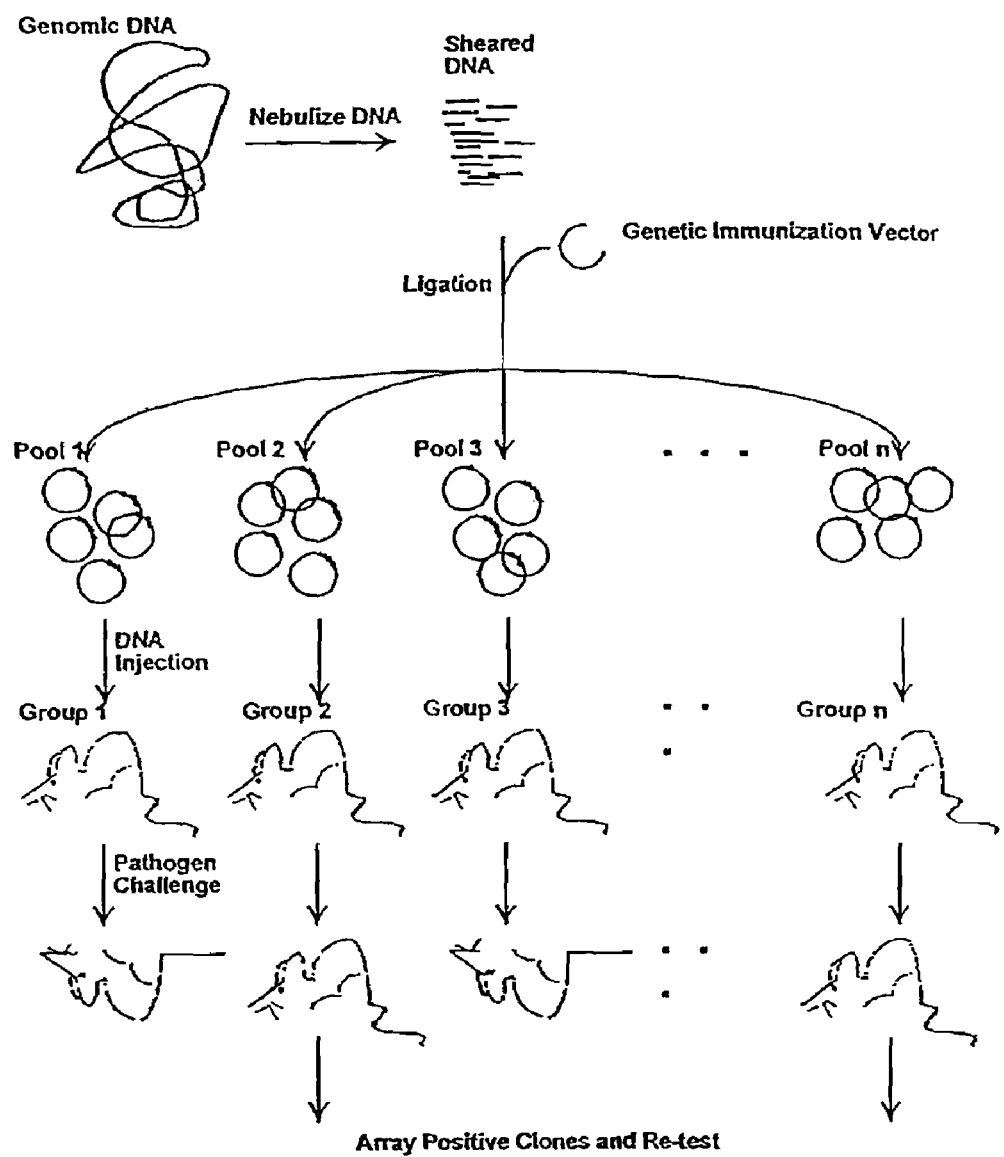
FIG. 1. Scheme for Expression Library Immunization

The widespread human and animal infections by the genus *Chlamydia* represents a particular challenge for vaccinology. Fore example, *Chlamydia psittaci* infections in cattle cause mastitis, infertility, and abortion. A primary economic impact of *Chlamydia* in dairy cattle is the loss of milk production and quality. Thus, an effective treatment for *Chlamydia* bacterial infections in human and other vertebrate animals would be of clinical and economic importance.

The present invention provides compositions and methods of the immunization of vertebrate animals, including humans, against infections using nucleic acid sequences and polypeptides elucidated by screening *Chlamydia psittaci*. These compositions and methods will be useful for immunization against *Chlamydia psittaci* bacterial infections and other infections and disease states. in particular embodiments, a vaccine composition directed against *Chlamydia* infections is provided. The vaccine according to the present invention comprises *Chlamydia* genes and polynucleotides identified by the inventors, that confer protective resistance in vertebrate animals to *Chlamydia* bacterial infections, and other infections. In other embodiments, the invention provides methods for immunizing an animal against *Chlamydia* infections, methods for preparing a cloned library via expression library immunization and methods for screening and identifying *Chlamydia* genes that confer protection against infection.

A. Expression Library Immunization

In particular embodiments, the immunization of vertebrate animals according to the present invention includes a cloned library of *Chlamydia* expression constructs. In specific embodiments, a cloned expression library of *Chlamydia psittaci* is provided. Expression library immunization, ELI herein, is well known in the art (U.S. Pat. No. 5,703,057, specifically incorporated herein by reference). In certain embodiments, the invention provides an ELI method applicable to virtually any pathogen and requires no knowledge of the biological properties of the pathogen. The method operates on the assumption, generally accepted by those skilled in the art, that all the potential antigenic determinants of any pathogen are encoded in its genome. The inventors have previously devised methods of identifying vaccines using a genomic expression library representing all of the antigenic determinants of a pathogen (U.S. Pat. No. 5,703,057). The method uses to its advantage the simplicity of genetic immunization to sort through a genome for immunological reagents in an unbiased, systematic fashion.

The preparation of an expression library is performed using techniques and methods familiar one of skill in the art. The pathogen's genome, may or may not be known or possibly may even have been cloned. Thus one obtains DNA (or cDNA), representing substantially the entire genome of the pathogen (e.g., *Chlamydia psittaci*). The DNA is broken up, by physical fragmentation or restriction endonuclease, into segments of some length so as to provide a library of about $10^5$ (approximately 18× the genome size) members. The library is then tested by inoculating a subject with purified DNA of the library or sub-library and the subject challenged with a pathogen, wherein immune protection of the subject from pathogen challenge indicates a clone that confers a protective immune response against infection.

B. Nucleic Acids

The present invention provides *Chlamydia* polynucleotide compositions and methods that induce a protective immune response in vertebrate animals challenged with a *Chlamydia* bacterial infection. The preparation and purification of antigenic *Chlamydia* polypeptides, or fragments thereof (Section C) and antibody preparations directed against *Chlamydia* antigens, or fragments thereof (Section E) are described below.

Thus, in certain embodiments of the present invention, genes or polynucleotides encoding *Chlamydia* polypeptides or fragments thereof are provided. It is contemplated in other embodiments, that a polynucleotide encoding a *Chlamydia* polypeptide or polypeptide fragment will be expressed in prokaryotic or eukaryotic cells and the polypeptides purified for use as anti-*Chlamydia* antigens in the vaccination of vertebrate animals or in generating antibodies immunoreactive with *Chlamydia* polypeptides (i.e., antigens). The genomes of *Chlamydia pneumonie* and *Chlamydia trachomatis* have been completely sequenced. The *Chlamydia* genes are quite similar, with the four most protective genes identified being 30-71% identical and 45-85% similar in amino acid sequence.

Genes for various species of the genus *Chlamydia* have been cloned, identified and compared (Kalman et al., 1999; Meijer et al, 1999). For example, the genomes of *Chlamydia pneumoniae, Chlamydia trachomatis, Chlamydia psittaci*, and *Chlamydia pecorum* have been studied. The present invention is not limited in scope to the genes of *Chlamydia psittaci*, however, as some of ordinary skill in the art could, using these nucleic acids, readily identify related homologues in various other species. In addition, it should be clear that the present invention is not limited to the specific nucleic acids disclosed herein. As discussed below, a specific "*Chlamydia*"

gene or polynucleotide fragment may contain a variety of different bases and yet sill produce a corresponding polypeptide that is functionally indistinguishable, and in some cases structurally indistinguishable, from the polynucleotide sequences disclosed herein by reference in U.S. patent application Ser. No. 09/738,269 filed on Dec. 15, 2000.

1. Nucleic Acids Encoding *Chlamydia* Polypeptides

The present invention provides polynucleotides encoding antigenic *Chlamydia psittaci* polypeptides capable of inducing a protective immune response in vertebrate animals and for use as an antigen to generate anti-*Chlamydia psittaci* or other pathogen antibodies. In certain instances, it may be desirable to express *Chlamydia psittaci* polynucleotides encoding a particular antigenic *Chlamydia psittaci* polypeptide domain or sequence to be used as a vaccine or in generating anti-*Chlamydia psittaci* or other pathogen antibodies. Nucleic acids according to the present invention may encode an entire *Chlamydia psittaci* gene, or any other fragment of the *Chlamydia psittaci* sequences set forth herein. The nucleic acid may be derived from genomic DNA, i.e., cloned directly from the genome of a particular organism. In other embodiments, however, the nucleic acid may comprise complementary DNA (cDNA). A protein may be derived from the designated sequences for use in a vaccine or to isolate useful antibodies.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when full or partial genomic sequence is preferred, such as where the non-doing regions are required for optimal expression.

It also contemplated that a given *Chlamydia* polynucleotide from a given species may be represented by natural variants that have slightly different nucleic acid sequences but, nonetheless, encode the same polypeptide (see Table 2 below). In addition, it is contemplated that a given *Chlamydia* polypeptide from a species may be generated using alternate codons that may be generated using alternate codons that result in a different nucleic acid sequence but encodes the same polypeptide.

As used in this application, the term "a nucleic acid encoding *Chlamydia* polynucleotide" refers to a nucleic acid molecule that has been isolated free of total cellular nucleic acid. The term "functionally equivalent codon" is used herein to refer to codons that encode the same amino acid, such as the six codons for arginine or serine (Table 2 below), and also refers to codons that encode the same amino acid, such as the six codons for arginine or serine (Table 22, below), and also refers to codons that biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic Acid | Glu | E | GAA GAG |
| Phenylalanine | Phe | F | UUC UUU |

TABLE 1-continued

| Amino Acids | | | Codons |
|---|---|---|---|
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for degeneracy of the genetic code, sequences that have at least about 50%, usually at least about 60%, more usually about 70%, most usually about 80%, preferably at least about 90% and most preferably about 95% of nucleotides that are identical to the nucleotides of given *Chlamydia* gene or polynucleotide. Sequences that are essentially the same as those set forth in a *Chlamydia* gene or polynucleotide may also be functionally defined as sequences that are capable of hybridizing to nucleic acid segment containing the complement of a *Chlamydia* polynucleotide under standard conditions.

The DNA segments of the present invention include those encoding biologically functional equivalent *Chlamydia* proteins and peptides, as described above. Such sequences may arise as a consequence of codon redundancy and amino acid functional equivalency that are know to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

2. Oligonucleotide Sequences

Naturally, the present invention also encompasses DNA segments that are complementary, or essentially complementary to the sequence of a *Chlamydia* polynucleotide. Nucleic acid sequences that are "complementary" are those that are capable of base-pairing according to the standard Watson-Crick complementary rules. As used herein the term "complementary sequences" means nucleic acid sequences that are substantially complementary, as may be assess by the same nucleotide comparison set forth above, or as defined as being capable of hybridizing to the nucleic acid segment of a *Chlamydia* polynucleotide under relatively stringent conditions such as those described herein. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introducted through the application of site-directed mutagenesis techniques or may be introduced randomly and screened later for the desired function, as described below.

Alternatively, the hybridizing segments may be shorter oligonucleotides. Sequences of 17 bases long should occur only once in the human genome and, therefore, suffice to specify a unique target sequence. Although short oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 250, 500, 1000, 1212, 1500, 2000, 2500, 3000 or 3500 bases and longer are contemplated as well. Such oligonucleotides will find use, for example as probes in Southern and Northern blots and as primers in amplification reactions, or for vaccines.

Suitable hybridization condition will be well known to those of skill in the art. In certain applications, for example, substitution of amino acids by site-directed mugtagenesis, it is appreciated that lower stringency conditions are required. Under these conditions, hybridization may occur even though the sequences of probe and target strand are not perfectly complimentary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C. Formamide and SDS also may be used to alter the hybridization conditions.

One method of using probes and primers of the present invention is in the search for genes related to *Chlamydia* or, more particularly, homologues of *Chlamydia* from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagensis of the underlying DNA. The techniques further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length in preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Polypeptides and Antigens

For the purposes of the present invention a *Chlamydia* polypeptide used as an antigen my be an naturally-occurring *Chlamydia* polypeptide that has been extracted using protein extraction techniques well know to those of skill in the art. In particular embodiments, a *Chlamydia* antigen is identified by ELI and prepared in a pharmaceutically acceptable carrier for the vaccination of an animal against *Chlamydia* infection.

In alternative embodiments, the *Chlamydia* polypeptide or antigen may be a synthetic peptide. In still other embodiments, the peptide may be a recombinant peptide produced through molecular engineering techniques. In other embodiments, gene fragment or sub-unit vaccines are utilized. The present section describes the methods and compositions involved in producing a composition of *Chlamydia* polypeptides for use as antigens in the present invention.

1. *Chlamydia* Polypeptides as Antigens

Section A describes methods for preparing a cloned *Chlamydia* library via ELI. Described also are methods for screening and identifying *Chlamydia* genes that confer protection against *Chlamydia* infection. Thus *Chlamydia* polypeptide encoding genes or their corresponding cDNA identified in the present invention can be inserted into an appropriate cloning vehicle for the production of *Chlamydia* polypeptides as antigens for the present invention. In addition, sequence variants of the polypeptide can be prepared. These may, for instance, be minor sequence variants of the polypeptide that arise due to natural variation within the population or they may be homologues found in other species. They also may be sequences that do not occur naturally, but that are sufficiently similar that they function similarly and/or elicit an immune response that cross-reacts with natural forms of the polypeptide. Sequence variants can be prepared by standard methods of site-directed mutagenesis such as those described below in the following section.

Another synthetic or recombinant variation of a *Chlamydia*-antigen is a polyepitopic moiety comprising repeats of epitopic determinants found naturally on *Chlamydia* proteins. Such synthetic polyepitopic proteins can be made up of several homomeric repeats of any one *Chlamydia* protein epitope; or can comprise of two or more heteromeric epitopes express on one or several *Chlamydia* protein epitopes.

Amino acid sequence variants of the polypeptide can be substitutional, insertional or deletion variants. Deletion variants lack one or more residues of the native protein which are not essential for function or immunogenic activity, and are exemplified by the variants lacking a transmembrane sequence described above. Another common type of deletion variant is one lacking secretory signal sequences or signal sequences directing a protein to bind to a particular part of a cell.

Substitutional variants typically contain the exchange of one amino acid for another at one or more sites within the protein, and may be designated to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: Alanine to serine, arginine to lysine; asparagine to glutamine or histidine; aspartate to glutamate; cysteine to serine; glutamine to asparagine; glatmate to aspartate; Glycine to praline; histidine to asparagine or glutamine isoleucine to leucine or valine; leucine to valine or isoleucine; lysine to arginine; methionine to leucine or isoleucine; phenylalanine to tyrosine, leucine or methionine; serine to Threonine; Threonine to serine; typtophan to tyrosine; tyrosine to trytophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide from one species, together with portions of the homologous polypeptide from another species. Other insertional variants can include those in which additional amino acids are introduced within the coding sequence of the polypeptide. These typically are smaller insertions that the fusion proteins described above and are introduced, for example, into a protease cleavage site.

In one embodiment, major antigenic determinants of the polypeptide may be identified by an empirical approach in which portions of the gene encoding the polypeptide are expressed in a recombinant host, and the resulting proteins tested for their ability to elicit an immune response. For example, the the polymerase chain reaction (PCR) can be used to prepare a range of cDNAs encoding peptides lacking successively longer fragments of the C-terminus of the protein. The immunogenic activity of each of these peptides then identifies those fragments or domains of the polypeptide that are essential for this activity. Further experiments in which only a small number of amino acids are removed or added at each iteration then allows the location of other antigenic determinants of the polypeptide. Thus, the polymerase chain reaction, a technique for amplifying a specific segment of DNA via multiple cycles of denaturation-renaturation, using a thermostable DNA polymerase, deoxyribonucleotides and primer sequences is contemplated in the present invention (Mullis, 1990; Mullis et al, 1992).

Another embodiment for the preparation of the polypeptides according to the invention is the use of peptide mimetics. Mimetics are peptide-containing molecules that mimic elements of protein secondary structure. Because many proteins exert their biological activity via relatively small regions of their folded surfaces, their actions can be reproduced by much smaller designer (mimetic) molecules that retain the bioactive surfaces and have potentially improved pharmacokinetic/dynamic properties (Fairlie et al., 1998).

The underlying rationale behind the use of peptide mimetics is that the peptide backbone of proteins exists chiefly to orient amino acid side chains in such a way as to facilitate molecular interactions, such as those antibody and antigen. However, unlike proteins peptides often lack well defined three dimensional structure in aqueous solution and tend to be conformationally mobile. Progress has been made with the use of molecular constraints to stabilize the bioactive conformations. By affixing or incorporating templates that fix secondary and tertiary structures of small peptides, synthetic molecules (protein surface mimetics) can be devised to mimic the localized elements of protein structure that constitute bioactive surfaces. Methods for mimicking individual elements of secondary structure (helices, turns, strands, sheets) and for assembling their combinations into tertiary structures (helix bundles, multiple loops, helix-loop-helix motifs) have been motifs) have been reviewed (Fairlie et al., 1998; Moore, 1994).

Methods for predicting, preparing, modifying, and screening mimetic peptides are described in U.S. Pat. No. 5,933,819 and U.S. Pat. No. 5,869,451 (each specifically incorporated herein by reference). It is contemplated in the present invention, that peptide mimetics will be useful in screening modulators of an immune response.

Modifications and changes may be made in the structure of a gene and still obtain a functional molecule that encodes a protein or polypeptide with desirable characteristics. The following is a discussion based upon changing the amino acids of a protein to create an equivalent, or even an improved, second-generation molecule. The amino acid changes may be achieved by changing the codons of the DNA sequences, according to the following data.

For example, certain amino acids may be substituted for other amino acids in a protein structure without appreciable loss of interactive binding capacity with structures such as, for example, antigen-binding region of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventor that various changes may be made in the DNA sequences of genes without appreciable loss of their biological utility or activity. Table 1 shows the codons that encode a particular amino acids.

In making such changes, the hydropathic index of amino acids may be considered. The importance of the hydropathic amino acid index in conferring interactive biologic function on a protein is generally understood in the art (Kyte and Doolittle, 1982).

It is accepted that the relative hydropathic character of the amino acid contributes to the secondary structure of the resultant protein, which in turn defines the interaction of the protein with other molecules, for example, enzymes, enzymes, substrates, receptors, DNA, antibodies, antigens and the like.

Each amino acid has been assigned a hydropathic index on the basis of their hydrophobicity and charge characteristics (Kyte and Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); Threonine (−0.7); serine (−0.8); tryptophan (−0.9); tyrosine (−1.3); praline (−1.6); histdine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index and score and still result in a protein with similar biological activity, i.e., still obtain a biological functionality equivalent protein. In making such changes, the substitution of amino acids whose hydropathic indices are within ±2 is preferred, those which are within ±1 are particularly preferred, and those within ±0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamine (+3.0±1); serine (+0.3); asparagine (+0.2); glutamine (+0.2); Glycine (0); threonine (−0.4); praline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. in such changes the substitution of amino acids whose hydrophilicity values are within ±2 is preferred, those that are within ±1 are particularly preferred, and those within ±0.5 are even more particularly preferred.

As outlined above, amino acid substitutions generally are based n the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

2. Synthetic Polypeptides

Contemplated in the present invention are *Chlamydia Psittaci* proteins and related peptides for use as antigens. In certain embodiments, the synthesis of a *Chlamydia* peptide fragment is considered. The peptides of the invention can be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Marrifield (1979), each incorporated herein by reference. Alternatively, recombinant DNA technology may be employed wherein a nucleotide sequence which encodes a peptide of the invention is inserted into an expression vector, transformed or transfected into an appropriate host cell and cultivated under conditions suitable for expression.

3. *Chlamydia* Polypeptide/Antigen Purification

*Chlamydia* polypeptides including *Chlamydia psittaci* polypeptides, of the present invention are used as antigens for inducing a protective immune response in an animal and for the preparation of anti-*Chlamydia* antibodies. Thus, certain aspects of the present invention concern the purification, of a of a *Chlamydia* polypeptide that is described herein above. The term "purified protein, or peptide" as used herein, is intended to refer to a composition, isolatable from other components, where the protein or peptide is purified to any degree relative to its naturally-obtainable state. A purified protein or peptide therefore also refers to a protein or peptide, free from environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be know to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known known in the art, it is believed that the order of conducting various purification steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecule sieve chromatography, is a special type of partition chromatography that is based on the molecular size. the theory behind gel chromatography is that the column, which is prepared with tiny particles of particles of an inert substance that contain small pores, separates large molecules form smaller molecules as they pass through or around the pores, depending on their size. As long as the material of which the particles are made does not absorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a sample matter to molecular weight.

Affinity Chromatography is a chromatographic procedure that relies on the specific affinity between substance to be isolated and the molecule that it can be specifically bind to. This is a receptor-ligand type interaction. The column material is synthesized by covalently coupling one of the binding partners to an insoluble matrix. The column material is then able to specifically absorb the substance from the solution. Elution occurs by changing the condition to those in which binding will not occur (alter pH, ionic strength, temperature, etc.).

4. Gene Fragment/Sub-Unit Vaccines

Gene fragment or sub-unit vaccines offer many advantages over conventional live or killed formulations. Notably, they are significantly safer. Additionally, by eliminating pathogen factors attenuating the host immune response, it is possible to create more effective vaccines. As discussed, the inventors have developed a technology to conduct complete screens of all of a pathogen's encoded proteins in an unbiased manner to identify the factors in the pathogen that should be included in a vaccine. The critical issues are to reduce the protective pools of the genes identified through the process, such as ELI, to individual genes or portions thereof, and if so, to identify what is protective.

In order to identify sub-unit vaccines, an ELI library is first constructed. Such a library of genetic immunization plasmids may be created by physically shearing and cloning the identified protective conferring libraries into a genetic immunization vector that drives transcription, such as the vector pCMVi-U B, a strong mammalian CMV promoter. The library is subsequently divided into pools, as described above, and injected into the animal challenge models, such as mice. The injected animal challenge models are boosted, then challenged. After a proper inoculation period, the animal models can be sacrificed for investigation to complete the first round of screening. In one preferred embodiment, the library represents more than six genomic expression equivalents, defined as the redundancy of authentic open reading frames ligated in-frame with ubiquitin. The library should be searched to make sure that it contains all regions of the genes that are candidates for a vaccine. The library is divided into a number of separate pools, each of the pools preferably containing approximately 2,400 to 3,400 plasmids.

The pools are then tested for protection against an infectious agent. One method for such protection testing is to use an intranasal mouse challenge model as described by U.S. Pat. No. 7,041,466, incorporated herein by reference. A relative protection score for the various pools may then be calculated to determine which pools confer the highest and lowest protection. When an animal challenge model is used, such as intranasal mouse challenge model, tissue may be isolated and real time quantitative PCR analysis may be performed on the tissue.

An important aspect of ELI screening and sub-unit identification approach is that the direct read-out for protection is disease, not immune correlates. The investigator may score directly for disease, and its prevention, using a quantifiable disease-dependent parameter. For example, it is known that in an intranasal mouse challenge model for *Chlamydia*-psittaci disease is proportional to lung weight. In this manner, pools that confer protection can be differentiated from the original number of sub-library pools. The identified sub-library pools that confer protection may then be selected and organized into a two dimensional array to derive subsequent sub-library DNA inocula for a second round of screening. For example, 24 rows and columns may be used and plasmid DNA may be prepared therefrom. In this example, each row and column represents a sub-library of approximately 1,700 sub-library of approximately 1,700 colonies and each matrix intersection would contain 96 colonies. In the second round of screening, each row and column DNA is used to vaccinate a group of challenged animals, as described above for Round 1. The rows and columns are scored as protection positive sub-libraries and intersections of the rows and columns that are protection positive are identified. The protection positive colonies are then re-arrayed into a second two dimensional grid, for the third round of testing. Again, DNA is prepared from the colonies comprising each row and column and an animal model is challenged. After inoculation of the DNA, and subsequent challenge with the pathogen, rows and columns are scored as positive if protective. The intersection of these rows and columns are identified as particularly protective, and the plasmids at such intersections are sequenced in order to eliminate those not likely to encode protective antigens. Only ubiquitin-fused gene fragments that encode peptides longer than a certain number of amino acids, preferably 50, but as few as nine, are tested as single clones for a fourth round of challenge on an animal model. The fourth round of protection ensures that the selected plasmids confer the desired protection.

One of the advantages of this protocol is that it can differentiate parts of the same gene that have opposite effects on protection. For example, some portions of a gene confer protection, while other portions of a gene are found to enhance disease. Thus, libraries based on fragmentation of genes may reveal antigens that would not have been evident from using whole genes. In fact, it is known that gene fragments are capable of conferring as much protection as the gold standard, a live vaccine.

Thus, expression library immunization enables comprehensive genomic analysis of protective genes and gene fragments. The process described above is readily applicable to any pathogen for which a suitable model exists. The major limitation is the size of the library made of randomly sheared DNA. However, now that the genomes of many pathogens have been sequenced, the ELI process is process is greatly facilitated. Using the genome sequence to PCR or to synthesize open reading frames reduces the complexity of the library approximately twenty-fold. Moreover, the development of linear expression element (LEE) technology now obviates the need for cloning, making the creation of libraries much faster. ELI can be done directly PCR-amplifying or chemically synthesizing all the genes of a pathogen, adding mammalian promoter and terminator and coding DNA fragments to create LEEs, and directly administering them in pools to test animals via genetic immunization.

Accordingly, the approach discussed above provides an unbiased functional genomic search for bacterial vaccine candidates in vivo and produces vaccine candidates that would not have been predicted by contemporary knowledge based approaches, such as bioinformatics. Particularly, with the current improvements in the protocol, ELI should be applicable to any pathogen. Specific experiments and results of this approach are further detailed in Examples 1-6, herein.

D. Gene Delivery

In certain embodiments of the invention, an expression construct comprising a *Chlamydia* gene or other polynucleotide segment under the control of heterologus promoter operable in eukaryotic cells is provided. For example, the delivery of *Chlamydia psittaci*, antigen-encoding expression constructs can be provided in this manner. The general approach in certain aspects of the present invention is to provide a cell with an expression construct encoding a specific protein, polypeptide or peptide fragment, thereby permitting the antigenic expression of the protein, polypeptide or peptide fragment to take effect in the cell. Following delivery of the expression construct, the protein, polypeptide or peptide fragment encoded by the expression construct is synthesized by the transcriptional and translational machinery of the cell, as well as any that may be provided by the expression construct.

Viral and non-viral vector systems are the two predominate categories for the delivery of an expression construct encoding a therapeutic protein, polypeptide, polypeptide fragment. Both vector systems are described in the following sections. There also are two primary approaches utilized in the delivery of an expression construct for the purposes of gene therapy; either indirect, ex vivo methods, or direct, in vivo methods. Ex vivo gene transfer comprises vector modification of (host) cells in culture and the administration or transplantation of the vector modified cells to a gene therapy recipient. In vivo gene transfer comprises direct introduction of the vector (e.g., injection, inhalation) into the target source or therapeutic gene recipient.

In certain embodiments of the invention, the nucleic acid encoding the gene or polynucleotide may be stably integrated into the genome of the cell. In yet further embodiments, the nucleic acid may be stably or transiently maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and/or where in the cell the nucleic acid remains dependent on the type of vector employed. The following gene delivery methods provide the framework for choosing and developing the most appropriate gene delivery system for a preferred application.

1. Non-Viral Polynucleotide Delivery

In one embodiment of the invention, a polynucleotide expression construct consists of naked recombinant DNA or plasmids. In preferred embodiments of the invention, an expression construct comprising for example, a *Chlamydia psittaci* polynucleotide is administered to a subject via injection and/or particle bombardment (e.g., a gene gun). Thus, in one preferred embodiment, polynucleotide expression constructs are transferred into cells by accelerating DNA-coated microprojectiles to a high velocity, allowing the DNA-coated microprojectiles to pierce cell membranes microprojectiles to pierce cell membranes and enter cells. In another preferred embodiment, polynucleotide expression construct ma be given by intramuscular, intravenous, subcutaneous, or intraperitoneal injection, as long as the polynucleotide expression construct can effectively be delivered to a desired target.

a. Particle Bombardment

Particle Bombardment depends on the ability to accelerate DNA-coated microprojectiles to a high velocity allowing them to pierce cell membranes and enter cells without killing them (Klein et al., 1987). Several devices for accelerating small particles have been developed. The most commonly used forms rely on high-pressure helium gas (Sanford et al., 1991), of which one of the present inventors is a co-inventor. The microprojectiles used have consisted of biologically inert substances such as tungsten or gold beads.

For microprojectile bombardment transformation using the constructs of the instant invention, both physical and biological parameters may be optimized. Physical factors are those that involve manipulating the DNA/microprojectile precipitate or those that affect the flight and velocity of either the macro- or microprojectiles. Biological factors include all steps involved in manipulation of cells before and immediately after bombardment, such as the osmotic adjustment of target cells to help alleviate the trauma associated with bombardment, the orientation of an immature embryo or other target tissue relative to the particle trajectory, and also the nature of the transforming DNA, such as linearized DNA or intact supercoiled plasmids.

Accordingly, it is contemplated that one way to wish to adjust various bombardment parameters in small scale studies to fully optimize the conditions. One may particularly wish to adjust physical parameters such as DNA concentration, gap distance, flight distance, tissue distance, and helium pressure. It is further contemplated that the grade of helium may effect transformation efficiency. One also may optimize the trauma reduction factors (TRFs) by modifying conditions which which influence the physiological state of the recipient cells and which may therefore influence transformation and integration efficiencies. For example, the osmotic state, tissue hydration and the subculture stage or cell cycle of the recipient cells may be adjusted for optimum transformation.

Other physical factors include those that involve manipulating the DNA/microprojectile precipitate or those that affect flight and velocity of either the macro- or microprojectiles. Biological factors include all steps involved in manipulation of cells immediately before and after bombardment. The pre-bombardment culturing conditions, such as osmotic environment, the bombardment parameters, and the plasmid configuration have been adjusted to yield the maximum numbers of stable transformants.

For microprojectile bombardment, one will attach (i.e., "coat") DNA to the microprojectiles such that it is delivered to recipient cells in a form suitable for transformation thereof. In this respect, at least some of the transforming DNA must be available to the target cell for transformation to occur, while that the same time during delivery the DNA must be attached to the microprojectile. Therefore, availability of the transforming DNA from the microprojectile may comprise the physical reversal of interactions between transforming DNA and the microprojectile following delivery of the microprojectile to the target cell. This need not be the case, however, as availability to a target cell may occur as a result of breakage of unbound segments of DNA or of other molecules which comprise the physical attachment to the microprojectile. Availability may further occur as a result of breakage of bonds between the transforming DNA and other molecules, which are either directly or indirectly attached to the microprojectile. It is further contemplated that transformation of a target cell may occur by way of direct illegitimate or homology-dependent recombination between the transforming DNA and the genomic DNA of the recipient cell. Therefore, as used herein, a "coated" microprojectile will be one which is capable of being used to transform a target cell, in that the transforming DNA will be delivered to the target cell, yet will be accessible to the target cell such that transformation may target cell such that transformation may occur.

Any technique for coating microprojectiles which allows for delivery of transforming DNA to the target cells may be used. Methods for coating microprojectiles which have been demonstrated to work well with the current invention have been specifically disclosed herein. DNA may be bound to microprojectile particles using alternative techniques, however. For example, particles may be coated with streptavidin and DNA end labled with long chain thiol cleavable biotinylated nucleotide chains. The DNA adheres to the particles due to the streptavidin-biotin interaction, but is released in the cell by reduction of the thiol linkage through reducing agents present in the cell.

Alternatively, particles may be prepared by functionalizing the surface of a gold oxide particle, providing free amine groups. DNA, having a strong negative charge, binds to the functionalized particles. Furthermore, charged particles may be deposited in controlled arrays on the surface of mylar flyer disks used in the PDS-1000 Biolistics device, thereby facilitating controlled distribution of particles to target tissue.

b. Other Non-Viral Methods of Polynucleotide Delivery

Transfer of a cloned expression construct in the present invention also may be performed by any of the methods which physically or chemically permabilize the cell membrane (e.g. calcium phosphate precipitation, DEAE-dextran, electroporation, direct microinjection, DNA-loaded liposomes and lipofectamine-DNA complexes, cell sonication, gene bombardment using high velocity microprojectiles and receptor-mediated transfection.

In certain embodiments, the use of lipid formulations and/or nanocapsules is contemplated for the introduction of a *Chlamydia psittaci* polynucleotide or polypeptide, or a gene therapy vector into host cells.

Nanocapsules can generally entrap compounds in a stable and/or reproducible way. To avoid side effects due to intracellular polymeric overloading, overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and/or such particles may be easily made.

In a preferred embodiment of the invention, the polynucleotide or polypeptide may be associated with a lipid. The polynucleotide or polypeptide associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. The lipid or lipid/polynucleotide or polypeptide associated compositions of the present invention are not limited to any particular structure in solution. For example, they may be present in a bilayer structure, as micelles, or with a "collapsed" structure. They may also simply be interspersed in a solution, possibly forming aggregates which are not uniform in either size or shape.

Lipids suitable for use according to the present invention can be obtained from commercial sources. For example, dimyristyl phosphatidylcholine ("DMPC") can be obtained from Sigma Chemical Co., dicetyl phosphate ("DCP") is obtained from K & K Laboratories (Plainview, N.Y.); cholesterol ("Chol") is obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Preferably, chloroform is used as the only solvent since it is more readily evaporated than methanol.

"Liposome" is a generic term encompassing a variety of single and multilamellar lipid vehicles formed by the generation of enclosed lipid bilayers or aggregates. Liposomes may be characterized as having vesicular structures with a a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). However, the present invention also encompasses compositions that have different structures in solution than the normal vesicular structure. For example, the lipids may assume a micellar structure or merely exist as non-uniform aggregates of lipid molecules. Also contemplated are lipofectamine-nucleic aid complexes.

Liposomes within the scope of the present invention can be prepared in accordance with know laboratory procedures, for example, the method of Bangham et al. (1965), the contents of which are incorporated herein by reference; the method of Gregoriadis, as described in *DRUG CARRIERS IN BIOLOGY AND MEDICINE*, G. Gregoriadis ed. (1979) pp. 287-341, the contents of which are incorporated herein by reference; the method of Deamer and Uster (1983), the contents of which are incorporated by reference; and the reverse-phase evaporation method as described by Szoka and Papahadjopoulos (1978).

Other vector delivery systems which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialganglioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumer endothelial cells, by any number of receptor-ligand systems with or without liposomes. For example, the human prostate-specific antigen (Watt et al., 1986) may be used as the receptor for mediated delivery of a nucleic acid in prostate tissue.

In another embodiment of the invention, the expression construct may simply consist of naked recombinant DNA or plasmids. Transfer of the construct may be performed by any of the methods mentioned above which physically or chemically permeabilize the cell membrane. This is applicable particularly for transfer in vitro, however it may be applied for in vivo use as well. Dubensky et al. (1984) successfully injected polyomavirus DNA in the form of $CaPO_4$ precipitates into liver and spleen of adult and newborn mice demonstrating active viral replication and acute infection. Benvenisty and Neshif (1986) also demonstrated that direct intraperitoneal injection of $CaPO_4$ precipitated plasmids results in expression of the transfected genes. It is envisioned that DNA encoding a *Chlamydia psittaci* gene or polynucleotide of interest may also be transferred in a similar manner in vivo and express the gene or polynucleotide product.

2. Viral Vectors

In certain embodiments, it is comtemplated that a *Chlamydia psittaci* gene or other polynucleotide that confers immune resistance to infection pursuant to the invention may be delivered by a viral vector. The capacity of certain viral vectors to efficiently infect or enter cells, to integrate into a host cell genome and stably express viral genes, have led to the development and application of a number of different viral vector systems (Robbins et al., 1998). Viral systems are currently being developed for use as vectors for ex vivo and in vivo gene transfer. For example, adenovirus, herpes-simple virus, retrovirus and adeno-associated virus vectors are being evaluated currently for treatment of diseases such as cancer, cystic fibrosis, Gaucher disease, renal disease and arthritis (Robbins and Ghivizzani, 1998; Imai et al., 1998; U.S. Pat. No. 5,670,488). The various viral vectors described below, present specific advantages and disadvantages, depending on the particular gene-therapeutic application.

a. Adenoviral Vectors

In particular embodiments, an adenoviral expression vector is contemplated for the delivery of expression constructs. "Adenovirus expression vector" is meant to include those constructs containing adenovirus sequences to (a) support packaging of the construct and (b) to ultimately express a tissue or cell-specific construct that has been cloned therein.

Adenoviruses comprise linear double stranded DNA, with a genome ranging from 30 to 35 kb in size (Reddy et al., 1998; Morrison et al., 1997; Chillon et al, 1999). An adenovirus expression vector according to the present invention comprises a genetically engineered form of the adenovirus. Advantages of adenoviral gene transfer include the ability to infect a wide variety of cell types, including non-dividing cells, a mid-sized genome, ease of manipulation, high infectivity and they can be grown to high titers (Wilson, 1996). Further, adenoviral infection of host cells does not result in chromosomal integration because the adenoviral DNA can replicate in an episomal manner, without potential genotoxicity associated with other viral vectors. Adenoviruses also are structurally stable (Marienfield et al., 1999) and no genome rearrangement has been detected after after extensive amplification (Parks et al., 1997; Bett et al., 1993).

Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al, 1999; Robbins et al., 1998; Graham and Prevec, 1995). The early genes E1, E2, E3 and E4 are expressed from the virus after infection and encode polypeptides that regulate viral gene expression, cellular gene expression, viral replication, inhibition of cellular apoptosis. Further on during viral infection, the MLP is activated, resulting in the expression of the late (L) genes, encodes components of the adenviral capsid. Adenoviral inverted terminal repeats (ITRs; 100-200 bp in length), are cis elements, function as origins of replication and are necessary for viral DNA replication. The v sequence is required for the packaging of the adenoviral genome.

A common approach for generating an adenoviruses for use as a gene transfer vector is the deletion of the E1 gene (E1), which is involved in the induction of E2, E3 and E4 promoters (Graham and Prevac, 1995). Subsequently, a therapeutic gene or genes can be inserted recombinantly in place of the E1 gene, wherein expression of the therapeutic gene(s) is driven by the E1 promoter or a heterologous promoter. The E1 polypeptides in trans (e.g., the human embryonic kidney cell line 293). Thus, in the present invention it may be convenient to introduce the transforming construct at the position from which the E1-coding sequences have been removed. However, the position of insertion of the construct within the adenovirus sequences is not critical to the invention. Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210, each specifically incorporated herein by reference).

Although adenovirus based vectors offer several unique advantages over other vector systems, they often are limited by vector immunogenicity, size constraints for insertion of recombinant genes and low levels of replication. The preparation of a recombinant adenovirus vector deleted of all open reading frames, comprising a full length dystrophin gene and the terminal repeats required for replication (Haecker et al., 1997) offers some potentially promising advantages to the above mentioned adenoviral shortcomings. The vector was grown to a high titer with a helper virus in 293 cells and was capable of efficiently transducing dystrophin in mdx mice, in myotubes in vitro and muscle fibers in vivo. Helper-dependent viral vectors are discussed below.

A major concern in using adenoviral vectors is the generation of a replication-competent virus during vector production in a packaging cell line or during gene therapy treatment of an individual. The generation of a replication-competent virus could pose a serious threat of an unintended viral infection and pathological consequences for the patient. Armentano et al., describe the preparation of a replication-defective adenovirus vector, claimed to eliminate the potential for the inadvertent generation of replication-competent adenovirus (U.S. Pat. No. 5,824,544, specifically incorporated herein by reference). The replication-defective adenovirus method comprises a deleted E1 region and a relocated protein IX gene, wherein the vector expresses a heterologous, mammalian gene.

Other than the requirement that the adenovirus vector be replication defective, or at least conditionally defective, the nature of the adenovirus vector is not believed to be crucial to the successful practice of the invention. The adenovirus may be of any of the 42 different know serotypes and/or subgroups A-F. Adenovirus type 5 of subgroup C is the preferred stating material in order to obtain the conditional replication-defective adenovirus vector for use in the present invention. This is because adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Smith, 1998; Hermens and Verhaggen, 1998), coronary diseases (Feldman et al., 1996), muscular diseases Petrof, 1998), gastrointestinal diseases (Wu, 1998) and various cancers such as colorectal (Fujiwara and Tanaka, 1998; Dorai et al., 1999), pancreatic (Carrion et al., 1999), bladder (Irie et al., 1999), head and neck (Blackwell et al., 1999), breast (Stewart et al., 1999), lung (Batra et al., 1999) and ovarian (Vanderkwaak et al., 1999).

b. Retroviral Vectors

In certain embodiments of the invention, the use of retroviruses for gene delivery are contemplated. Retroviruses are RNA viruses comprising an RNA genome. When a host cell is infected by a retrovirus, the genomic RNA is reverse transcribed into a DNA intermediate which is integrated into the chromosomal DNA of infected cells. This integrated DNA intermediate is referred to as a provirus. A particular advantage of retroviruses is that they can stably infect dividing cells with a gene of interest (e.g., a therapeutic gene) by integrating into the host DNA, without expressing immunogenic viral proteins. Theoretically, the integrated retroviral vector will be maintained for the life of the infected host cell, expressing the gene of interest.

The retroviral genome and the proviral DNA have three genes: gag, pol, and env, which are flanked by two long terminal repeat (LTR) sequences. The gag gene encodes the internal structural (matrix, capsid, and nucleocapsid) proteins; the pol gene encodes the RNA-directed DNA polymerase (reverse transcriptase) and the env gene encodes viral envelope glycoproteins. The 5' and 3' LTRs serve to promote transcription and polyadenylation of the virion RNAs. The LTR contains all other cis-acting sequences necessary for viral replication.

A recombinant retrovirus of the present invention may be genetically modified in such a way that some of the structural, infectious genes of the native virus have been removed and replaced instead with a nucleic acid sequence to be delivered to a target cell (U.S. Pat. No. 5,858,744; U.S. Pat. No. 5,739,018, each incorporated herein by reference). After infection of a cell by the virus, the virus injects its nucleic acid into the cell and the retrovirus genetic material can integrate into the host cell genome. The transferred retrovirus genetic material is then transcribed and translated into proteins within the host cell. As with other viral vector systems, the generation of a replication-competent retrovirus during vector production or during therapy is a major concern. Retroviral vectors suitable for use in the present invention are generally defective retroviral vectors that are capable of infecting the target cell, reverse transcribing their RNA genomes, and integrating the reverse transcribed DNA into the target cell genome, but are incapable of replicating within the target cell to produce infectious retroviral particles (e.g., the retroviral genome transferred into the target cell is defective in gag, encoding virion structural proteins, and/or in pol, the gene encoding reverse transcriptase). Thus, transcription of the provirus and assembly into infectious virus occurs in the presence of an appropriate helper virus or in a cell line containing appropriate sequences enabling encapsidation without coincident production of a contaminating helper virus.

The growth and maintenance of retroviruses is known in the art (U.S. Pat. No. 5,955,331; U.S. Pat. No. 5,888,502, each specifically incorporated herein by reference). Nolan et al. describe the production of stable high titre, helper-free retrovirus comprising a heterlogous gene (U.S. Pat. No. 5,830,725, specifically incorporated herein by reference). Methods for constructing packaging cell lines useful for the generation of helper-free recombinant retroviruses with amphoteric or ecotrophic host ranges, as well as methods of using the recombinant retroviruses to introduce a gene of interest into eukaryotic cells in vivo and in vitro are contemplated in the present invention (U.S. Pat. No. 5,955,331).

Currently, the majority of all clinical trials for vector mediated gene delivery use murine leukemia virus (MLV)-based retroviral vector gene delivery (Robbins et al., 1998; Miller et al., 1993). Disadvantages of retroviral gene delivery includes a requirement for ongoing cell division for stable infection and a coding capacity that prevents the delivery of large genes. However, recent development of vectors such as lentivirus (e.g., HIV) simian immunodeficiency virus (SIV) and equine infectious-anemia virus (EIAV), which can infect certain non-dividing cells, potentially allow the in vivo use of retroviral vectors for gene therapy applications (Amado and Chen, 1999; Klimatcheva et al., 1999), islets (Leibowitz et al., 1999) and muscle cells (Johnston et al., 1999). The therapeutic delivery of genes via retroviruses are currently being assess for the treatment of various disorders such as inflammatory disease (Moldawer et al., 1999), AIDS (Amado et al., 1999; Engel and Kohn, 1999), cancer (Clay et al., 1999), cerebrovascular disease (Weihl et al., 1999) and hemophilia (Kay, 1998).

c. Herpes-Simplex Viral Vectors

Herpes simplex virus (HSV) type I and type II contain a double-stranded, linear DNA genome of approximately 150 kb, encoding 70-80 genes. Wild type HSV are able to infect cells lytically and to establish latency in certain cell types (e.g., neurons). Similar to adenovirus, HSV also can infect a variety of cells types include muscle (Yeung et al., 1999), ear (Derby et al., 1999), eye (Kaufman et al., 1999), tumors (Yoon et al., 1999; Howard et al., 1999), lung (Kohut et al., 1998), neuronal (Gamido et al., 1999; Lachmann and Efstathiou, 1999), liver (Miytake et al., 1999; Kooby et al., 1999) and pancreatic islets (Rabinovitch et al., 1999).

HSV viral genes are transcribed by cellular RNA polymerase II and are temporally regulated, resulting in the transcription and subsequent synthesis of gene products in roughly three discernable phases or kinetic classes. These phases of genes are referred to as the Immediate Early (IE) or alpha genes, Early (E) or beta genes and Late (L) or gamma genes. Immediately following the arrival of the genome of a virus in the nucleus of a newly infected cell, the IE genes are transcribed. The efficient expression of these genes do not require prior viral protein synthesis. The products of IE genes are required to activate transcription and regulate the remainder of the viral genome.

For use in therapeutic gene delivery, HSV must be rendered replication-defective. Protocols for generating replication-defective HSV helper virus-free cell lines have been described (U.S. Pat. No. 5,879,934; U.S. Pat. No. 5,851,826, each specifically incorporated herein by reference in its entirety). One IE protein, Infected Cell Polypeptide 4 (ICP4), also known as alpha 4 or Vmw175, is absolutely required for both virus infectivity and the transition from IE to later transcription. Thus, due to its complex, multifunctional nature and central role in the regulation of HSV gene expression, ICP4 has typically been the target of HSV genetic studies.

Phenotypic studies of HSV viruses deleted of ICP4 indicate that such viruses will be potentially useful for gene transfer purposes (Krisky et al., 1998a). One property of viruses deleted for ICP4 that makes them desirable for gene transfer is that they only express the five other IE genes: ICP0, ICP6, ICP27, ICP22, and ICP47 (DeLuca et al., 1985), without the expression of viral genes encoding proteins that direct viral DNA synthesis, as well as the structural proteins of the virus. This property is desirable for minimizing possible deleterious effects on host cell metabolism or an immune response following gene transfer. Further deletion of IE genes ICP22 and ICP27, in addition to ICP4, substantially improve reduction of HSV reduction of HSV cytotoxicity and prevented early and late viral gene expression (Krisky et al., 1998b).

The therapeutic potential of HSV in gene transfer has been demonstrated in various in vitro model systems and in vivo for diseases such as Parkinson's (Yamada et al., 1999), retinoblastoma (Hayashi et al., 1999), intracerebral and intradermal tumors (Moriuchi et al., 1998), B cell malignancies (Suzuki et al., 1998), ovarian cancer (Wang et al., 1998) and Duchenne muscular dystrophy (Huard et al., 1997).

c. Adeno-Associated Viral Vectors

Adeno-associated virus (AAV), a member of the parvovirus family, is a human virus that is increasingly being used for gene delivery therapeutics. AAV has several advantageous features not found in other viral systems. First, AAV can infect a wide range of host cells, including non-dividing cells. Second, AAV can infect cells from different species. Third, AAV has not been associated with any human or animal disease and does not appear to alter the biological properties of the host cell upon integration. For example, it is estimated that 80-85% of the human population has been exposed to AAV. Finally, AAV is stable at a wide range of physical and chemical conditions which lends itself to production, storage and transportation requirements.

The AAV genome is a linear, single-stranded DNA molecule containing 4681 nucleotides. The AAV genome generally comprises an internal non-repeating genome flanked on each end by inverted terminal repeats (ITRs) of approximately 145 bp in length. The ITRs have multiple functions, including origins of DNA replication, and as packaging signals for the viral genome. The internal non-repeated portion of the genome includes two large open reading frames, known as the AAV replication (rep) and capsid (cap) genes. The rep and cap genes code for viral proteins that allow the virus to replicate and package the viral genome into a virion. A family of at least four viral proteins are expressed form the AAV rep region, Rep 78, 78, Rep 68, Rep 52, and Rep 40, named according to their apparent molecular weight. The AAV cap region encodes at least three proteins, VP1, VP2, and VP3.

AAV is a helper-dependent virus requiring co-infection with a helper virus (e.g., adenovirus, herpesvirus or vaccinia) in order to form AAV virions. In the absence of co-infection with a helper virus, AAV establishes a latent state in which the viral genome inserts into a host cell chromosome, but infectious virions are not produced. Subsequent infection by a helper virus "rescues" the integrated genome, allowing it to replicate and package its genome into infectious AAV virions. Although AAV can infect cells from different species, the helper virus must be of the same species as the host cell (e.g., human AAV will replicate in canine cells co-infected with a canine adenovirus).

AAV has been engineered to deliver genes of interest by deleting the internal non-repeating portion of the AAV genome and inserting a heterologous gene between the ITRs. The heterologous gene may be functionally linked to a heterologous promoter (constitutive, cell-specific, or inducible) capable of driving gene expression in target cells. To produce infectious recombinant AAV (rAAV) containing a heterologous gene, a suitable producer cell line is transfected with a rAAV vector containing a heterologous gene. The producer cell is concurrently transfected with a second plasmid harboring the AAV rep and cap genes under the control of their respective endogenous promoters or heterologous promoters. Finally, the producer cell is infected with a helper virus.

Once these factors come together, the heterologous gene is replicated and packaged as though it were a wild-type AAV genome. When target cells are infected with the resulting rAAV virions, the heterologous gene enters and is expressed in the target cells. Because the target cells lack the rep and cap genes and the adenovirus helper genes, the rAAV cannot further replicate, package or form wild-type AAV.

The use of helper virus, however, presents a number of probles. First, the use of adenovirus in a rAAV production system causes the host cells to produce both rAAV and infectious adenovirus. The contaminating infectious adenovirus can be inactivated by heat treatment (56.degree. C. for 1 hour). Heat treatment however, results in approximately a 50% drop in the titer of functional rAAV virions. Second, varying amounts of adenovirus proteins are present in these preparations. For example, approximately 50% or greater of the total protein obtained in such rAAV virion preparations is free adenovirus fiber protein. If not completely removed, these adenovirus proteins have the potential of eliciting an immune response from the patient. Third, AAV vector production methods which employ a helper virus, which presents a number of health and safety concerns, particularly in regard to the use of a herpesvirus. Fourth, concomitant production of helper virus particles in rAAV virion producing cells diverts large amounts of host cellular resources away from rAAV virion production, potentially resulting in lower rAAV virion yields.

e. Other Viral Vectors

The development and utility of viral vectors for gene delivery is constantly improving and evolving. Other viral vectors such as poxvirus; e.g. vaccinia virus (Gnant et al., 1999; Gnant et al., 1999), alpha virus; e.g., sindbis virus, Semliki forest virus (Lundstrom, 1999), reovirus (Coffey et al., 1998)

and influenza A virus (Neumann et al., 1999) are contemplated for use in the present invention and may be selected according to the requisite properties of the target system.

In certain embodiments, vaccinia viral vectors are contemplated for use in the present invention. Vaccinia virus is a particularly useful eukaryotic viral vector system for expressing heterologous genes. For example, when recombinant vaccinia virus is properly engineered, the proteins are synthesized, processed and transported to the plasma membrane. Vaccinia viruses as gene delivery vectors have recently been demonstrated to transfer genes to human tumor cells, e.g., EMAP-II (Gnant et al., 1999), inner ear (Derby et al., 1999), glioma cells, e.g., p53 (Timiryasova et al., 1999) and various mammalian cells e.g., P-450 (U.S. cells e.g., P-450 (U.S. Pat. No. 5,506,138). The preparation, growth and manipulation of vaccinia viruses are described in U.S. Pat. No. 5,849,304 and U.S. Pat. No. 5,506,138 (each specifically incorporated herein by reference).

In other embodiments, sindis viral vectors are contemplated for use in gene delivery. Sindbis virus is a species of the alphavirus genus (Garoff and Li, 1998) which includes such important pathogens as Venezuelan, Western and Eastern equine encephalitis viruses (Sawai et al., 1999; Mastrangelo et al., 1999). In vitro, sindbis virus infects a variety of avian, mammalian, reptilian, and amphibian cells. The genome of sindbis virus consists of a single molecule of a single-stranded RNA, 11,703 nucleotides in length. The genomic RNA is infectious, is capped at the 5' terminus and polyadenylated at the 3' terminus, and serves as mRNA. Translation of a vaccinia virus 26S mRNA produces a polyprotein that is cleaved co- and post-translationally by a combination of viral and presumably host-encoded proteases to give the three virus structural proteins, a capsid protein (C) and the two envelope glycoproteins (E1 and PE2, precursors of the virion E2).

Three features of sindbis virus suggest that it would be a useful vector for the expression of heterologous genes. First, its wide host range, both in nature and in the laboratory. Second, gene expression occurs in the cytoplasm of the host cell and is rapid and efficient. Third, temperature-sensitive mutations in RNA synthesis are available that may be used to modulate the expression of heterologous coding sequences by simply shifting cultures to the non-permissive temperature at various time after infection. The growth and maintenance of sindbis virus is known in the art (U.S. Pat. No. 5,217,879 specifically incorporated herein by reference).

f. Chimeric Viral Vectors

Chimeric or hybrid viral vectors are being developed for use in therapeutic gene delivery and are contemplated for use in the present invention. Chimeric poxyiral/retroviral vectors (Holzer et al., 1999), adenoviral/retroviral vectors (Feng et al. 1997; Bilbao et al., 1997; Caplen et al., 1999) and adenoviral/adeno-associated viral vectors (Fisher et al., 1996; U.S. Pat. No. 5,871,982) have been described.

These "chimeric" viral gene transfer systems can exploit the favorable features of two or more parent viral species. For example, Wilson et al., provide a chimeric vector construct which comprises a portion of anadenovirus, AAV 5' and 3' ITR sequences and a selected transgene, described below (U.S. Pat. No. 5,871,983, specifically incorporate herein by reference).

The adenovirus/AAV chimeric virus uses adenovirus nucleic acid sequences as a shuttle to deliver a recombinant AAV/transgene genome to a target cell. The adenovirus nucleic acid sequences employed in the hybrid vector can range from a minimum sequence amount, which requires the use of a helper virus to produce the hybrid virus particle, to only selected deletions of adenovirus genes, which deleted gene products can be supplied in the hybrid viral production process by a selected packaging cell. At a minimum, the adenovirus nucleic acid sequences employed in the pAdA shuttle vector are adenovirus genomic sequences from which all viral genes are deleted and which contain only those adenovirus sequences required for packaging adenoviral genomic DNA into a performed capsid head. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. The adenovirus sequences may be modified to contain desired deletions, substitutions, or mutations, provided that the desired function is not eliminated.

The AAV sequences useful in the above chimeric vector are viral sequences from which the rep and cap polypeptide encoding sequences are deleted. More specifically, the AAV sequences employed are the cis-acting 5' and 3' 3' inverted terminal repeat (ITR) sequences. These chimeras are characterized by high titer transgene delivery to a host cell and the ability to stably integrate the transgene into the host cell chromosome (U.S. Pat. No. 5,871,983, specifically incorporate herein by reference). In the hybrid vector construct, the AAV sequences are flanked by the selected adenovirus sequences discussed above. The 5' and 3' AAV ITR sequences themselves flank a selected transgene sequence and associated regulatory elements, described below. Thus, the sequence formed by the transgene and flanking 5' and 3' AAV sequences may be inserted at any deletion site in the adenovirus sequences of the vector. For example, the AAV sequences are desirably inserted at the site of the deleted E1a/E1b genes of the adenovirus. Alternatively, the AAV sequences may be inserted at an E3 deletion, and so on. Alternatively, the AAV sequences may be inserted at an E3 deletion, E2a delection, and so on. If only the adenovirus 5' ITR/packaging sequences and 3' ITR sequences are used in the hybrid virus, the AAV sequences are inserted between them.

The transgene sequence of the vector and recombinant virus can be a gene, a nucleic acid sequence or reverse transcript thereof, heterologous to the adenovirus sequence, which encodes a protein, polypeptide or peptide fragment of interest. The transgene is operatively linked to regulatory components in a manner which permits transgene transcription. The composition of the transgene sequence will depend upon the use to which the resulting hybrid vector will be put. For example, one type of transgene sequence includes a therapeutic gene which expresses a desired gene product in a host dcell. These therapeutic genes or nucleic acid sequences typically encode products for administration and expression in a patient in vivo or ex vivo to replace or correct an inherited or non-inherited genetic defect or treat an epigenetic disorder or disease.

E. *Chlamydia* Antibodies

In another aspect, the present invention provides antibody compositions that are immunoreactive with a *Chlamydia* polypeptide of the present invention, or any portion thereof.

An antibody can be a polyclonal or a monoclonal antibody. An antibody may also be monovalent or bivalent. A prototype antibody is an immunoglobulin composed by four polypeptide chains, two heavy and two light chains, held together by disulfide bonds. Each pair of heavy and light chains forms an antigen biding site, also defined as complementarity-determining region (CDR). Therefore, the prototype antibody has two CDRs, can bind two antigens, and because of this feature is defined bivalent. The prototype antibody can be split by variety of biological or chemical means. Each half of the antibody can only bind one antigen, and, therefore, is defined monovalent. Means for preparing and characterizing antibodies are well known n the art (see, e.g., Howell and Lane, 1988).

Peptides corresponding to one or more antigenic determinants of a *Chlamydia* polypeptide of the present invention also can be prepared. Such peptides should generally be at least five or six amino acid residues in length, will preferably be about 10, 15, 20, 25 or about 30 amino acid residues in length, and may contain up to about 35-50 residues or so. Synthetic peptides will generally be about 35 residues long, which is the approximate upper length limit of automated peptide synthesis machines, such as those available from Applied Biosystems (Foster City, Calif.). Longer peptides also may be prepared, e.g., by recombinant means.

The identification and preparation of epitopes from primary amino acid sequences on the basis of hydrophilicity is taught in U.S. Pat. No. 4,554,101 (Hopp), incorporated herein by reference. Through the methods disclosed in Hopp, one of skill in the art would be able to identify epitopes from within an amino acid sequence such as a *Chlamydia* polypeptide sequence.

Numerous scientific publications have also been devoted to the prediction of secondary structure, and to the identification of epitopes, from analyses of amino acid sequence (Chou & Fasman, 1974a; Chou & Fasman, 1974b; Chou & Fasman, 1978a; Chou & Fasman, 1978b; Chou & Fasman, 1979). Any of these may be used if desired, to supplement the teachings of Hopp in U.S. Pat. No. 4,554,101.

Moreover, computer programs are currently available to assist with predicting antigenic portions and epitopic core regions of proteins. Examples include those programs based upon the Jameson-Wolf analysis (Jameson & Wolf, 1988; Wolf et al., 1988), the program PEPPLOT® (Brutlag et al., 1990; Weinberger et al., 1985), and other new programs for protein tertiary structure prediction (Fetrow & Bryant, 1993). Another commercially available software program capable of carrying out such analyses is MACVECTOR (IBI, New Haven, Conn.).

In further embodiments, major antigenic determinants of a *Chlamydia* polypeptide may be identified by an empirical approach in which portions of the gene encoding the polypeptide are expressed in a recombinant host, and the resulting proteins tested for their ability to elicit an immune response. For example, PCR can be used to prepare a range of peptides lacking successively longer fragments of the C-terminus of the protein. The immunoactivity of each of these peptides is determined to identify those fragments or domains of the polypeptide that are immunodominant. Further studies in which only a small number of amino acids are removed at each iteration then allows the location of the antigenic determinants of the polypeptide to be more precisely determined.

Another method for determining the major antigenic determinants of a polypeptide is the SPOTS system (Genosys Biotechnologies, Inc., The Woodlands, Tex.). In this method, overlapping peptides are synthesized on a cellulose membrane, which following synthesis and deprotection, is screened usig a polyclonal or monoclonal antibody. The antigenic determinants of the peptides which are initially identified can further localized by performing subsequent of smaller peptides with larger overlaps, and by eventually replacing individual amino acids at each position along the immunoreactive peptide.

Once one or more such analyses are completed, polypeptides are prepared that contain at least the essential features of one or more antigenic determinants. The peptides are then employed in the generation of antisera against the polypeptide. Minigenes or gene fusions encoding these determinants also can be be constructed and inserted into expression vectors by standard methods, for example, using PCR cloning methodology.

The use of such small peptides for antibody generation or vaccination typically requires conjugation of the peptide to an immunogenic carrier protein, such as hepatitis B surface antigen, keyhole limpet hemocyanin or bovine serum albumin. Methods for performing this conjugation are well know in the art.

1. Anti-Chlamydia Antibody Generation

The present invention provides monoclonal antibody compositions that are immunoreactive with a *Chlamydia* polypeptide. As detailed above, in addition to antibodies generated against a full length *Chlamydia* polypeptide, antibodies also may be generated in response to smaller constructs comprising epitopic core regions, including wild-type and mutant epitopes. In other embodiments of the invention, the use of anti-*Chlamydia* single chain antibodies, chimeric antibodies, diabodies, and the like are contemplated.

As used herein, the term "antibody" is intended to refer broadly to any immunologic binding agent such as IgG, IgM, IgA, IgD and IgE. Generally, IgG and/or IgM are preferred because they are the most common antibodies in the physiological situation and because they are most easily made in a laboratory setting.

Monoclonal antibodies (mAbs) are recognized to have certain advantages, e.g., reproducibility and large-scale production, and their use is generally preferred.

However, "humanized" *Chlamydia* antibodies also are contemplated, as are chimeric antibodies form mouse, rate, goat and other species, fusion proteins, single chain antibodies, diabodies, bispecific antibodies, and other engineered antibodies and fragments thereof. As defined herein a "humanized" antibody comprises constant regions from a human antibody gene and variable regions form a non-human antibody gene. A 'chimeric antibody, comprises constant constant and variable regions from two genetically distinct individuals. An anti-*Chlamydia* humanized or chimeric antibody can be genetically engineered to comprise a *Chlamydia* antigen binding site of a given of molecular weight and biological lifetime, as long as the antibody retains its *Chlamydia* antigen binding site.

The term "antibody" is used to refer to any antibody-like molecule that has an antigen binding region, and includes antibody fragments such as Fab', Fab, $F(ab')_2$, single domain antibodies (DABs), Fv, scFv, (single chain Fv), chimeras and the like. Methods and techniques of producing the above antibody-based constructs and fragments are well known in the art (U.S. Pat. No. 5,889,157; U.S. Pat. No. 5,821,333; U.S. Pat. No. 5,888,773, each specifically incorporated herein by reference).

U.S. Pat. No. 5,889,157 describes a humanized B3 scFv antibody preparation. The B3 scFv is encoded from a recombinant, fused DNA molecule, that comprises a DNA sequence encoding humanized Fv heavy and light chain regions of a B3 antibody and a DNA sequence that encodes an effector molecule. The effector molecule can be any agent having a particular biological activity which is to be directed to a particular target cell or molecule. Described in U.S. Pat. No. 5,888,773, is the preparation of scFv antibodies produced in eukaryotic cells, wherein the scFv antibodies are secreted from the eukaryotic cells into the cell culture medium and retain their biological activity. It is contemplated that similar methods for preparing multi-functional anti-*Chlamydia* fusion proteins, as described above, may be utilized in the present invention.

Means for preparing and characterizing antibodies also are well known in the art (See, e.g., Antibodies: A Laboratory Manual, Cold Spring Harbor Laboratory, 1988; incorporated herein by reference). The methods for generating monoclonal antibodies (mAbs) generally begin along the same lines as those preparing for polyclonal antibodies. Briefly, a polyclonal antibody is prepared by immunizing an animal with an immunogenic *Chlamydia* polypeptide composition in composition in accordance with the present invention and collecting antisera from that immunized animal.

A wide range of animal species can be used for the production of antisera. Typically the animal used for production of antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin also can be used as carriers. Means for conjugating a polypeptide to a carrier protein are well known in the art and include glutaraldehyde, m-maleimido-benzoyl-N-hydroxysuccinimide ester, carbodiimide and bis-biazotized benzidine.

As also well known in the art, the immunogenicity of a particular immunogen composition can be enhanced by the use of non-specific stimulators of the immune response, known as adjuvants. Suitable molecule adjuvants include all acceptable immunostimulatory compounds, such as cytokines, toxins, or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion also is comtemplated. MHC antigens may even be used. Exemplary, often preferred adjuvants include complete Freund's adjuvant (a non-specific stimulator of the immune response containing killed *Mycobacterium tuberculosis*), incomplete Freund's adjuvants and aluminum aluminum hydroxide adjuvant.

In addition to adjuvants, it may be desirable to coadminister biologic response modifiers (BRM), which have been shown to upregulate T cell immunity or downregulate suppressor cell activity. Such BRMs include, but are not limited to, Cimetidine (CIM; 1200 mg/d) (SmithKline Beecham, PA); low-dose Cyclophosphamide (CYP; 300 mg/m$^2$) (Johnson/Mead, NJ), cytokines such as γ-interferon, IL-2 or IL-12 or genes encoding proteins involved in immune helper functions, such as B-7.

The amount of immunogen composition used in the production of polyclonal antibodies varies upon the nature of immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and tittering is repeated until a suitable titer is achieved. When a desired level of immunogenicity is obtained, the immunized animal can be bled and the serum isolated and stored, and/or the animal can be used to generate mAbs.

For production of rabbit polyclonal antibodies, the animal can be bled through an ear vein or alternatively by cardiac puncture. The removed blood s allowed to coagulate and then centrifuged to separate serum components from the whole cells and blood clots. The serum may be used as is for various applications or else the desired antibody fraction may be purified by well-known methods, such as affinity chromatography using another antibody, a peptide bound to a solid matrix, or by using, e.g., protein A or protein G chromatography.

mAbs may be readily prepared through use of well-know techniques, such as those exemplified in U.S. Pat. No. 4,196,265, incorporated herein by reference. Typically, this technique involved immunizing a suitable animal with a selected immunogen composition, e.g., a purified or partially purified *Chlamydia* polypeptide, peptide or domain, be it a wild-type or mutant composition. The immunizing composition is administered in a manner effective to stimulate antibody producing cells.

The methods for generating monoclonal antibodies (mAbs) generally begin along the same lines as those for preparing polyclonal antibodies. Rodents such as mice and rats are preferred animals, however, the use of rabbit, sheep or frog cells also is possible. The use of rates may provide certain advantages (Goding, 1986, pp. 60-61), but mice are preferred with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals, or the gene encoding the protein of interest can be directly injected.

Following immunization somatic cells with the potential for producing antibodies, specifically B lymphocytes (B cells), are selected for use in the mAb generating protocol. These cells may be obtained from biopsied spleens, tonsils or lymph nodes, or from peripheral blood sample. Spleen cells and peripheral blood cells are preferred, the former because they are a rich source of antibody-producing cells that are in the dividing plasmablast stage, and the latter because peripheral blood is easily accessible.

Often, a panel of animals will have been immunized and the spleen of an animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are know to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag-4-1), which is readily available from the NIGMS Human Genetic Mutant Cell Respository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, through the proportion may vary form about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electricity induced fusion method also is appropriate (Goding pp. 71-74, 1986).

Fusion procedures usually produce viable hybrids at low frequencies, about $1 \times 10^{-6}$ to $1 \times 10^{-8}$. However, this does not pose a problem, as the the viable, fused hybrids are differentiated from the parental, unfused cells (particularly the unfused myeloma cell that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. HAT medium, a growth medium containing hypoxanthine, aminopterin and thymidine, is well known in the art as a medium for selection of hybrid cells. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used the media is supplemented with hypoxanthine.

The preferred selection medium is HAT. Only cells capable of operating nucleotide salvage pathways are able to survive HAT medium. The myeloma cells are defective in key enzymes of the salvage pathway, e.g. hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population a of hybridomas from which specific hybridomas are selected. Typically, selection hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas then would be serially diluted and cloned into individual antibody-producing cell lines, which clones can the be propagated indefinitely to provide mAbs. The cell lines may be exploited for mAb production in two basic ways. First, a sample of the hybridoma can be injected (often into the peritoneal cavity) into a histocompatabile animal of the type that was used to provide the somatic and myeloma cells for the original fusion (e.g., a syngeneic mouse). Optionally, the animals are primed with a hydrocarbon, especially oils such as pristine (tetramethylpentadecane) prior injection. The injected animal develops tumors secreting the specific monoclonal antibody produced by the fused cell hybrid. The body fluids of the animal, such as serum or ascites fluid, can then be tapped to provide mAbs in high concentration. Second, the individual cell lines could be cultured in vitro, where the mAbs are naturally secreted into the culture medium from which they can be readily obtained in high concentrations.

mAbs produced by either means may be further purified, if desired, using filtration, centrifugation and various chromatographic methods such as HPLC or affinity chromatography. Fragments of the monoclonal antibodies of the invention can be obtained from the monoclonal antibodies so produced by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It is also contemplated that a molecular cloning approach may be used to generate monoclonals. For this, combinatorial immunoglobin phagemid libraries are prepared from RNA isolated from the spleen of the immunized animal, and phagemids expressing appropriate antibodies are selected by panning using cells expressing the antigen and control cells. The advantages of this approach over conventional hybridoma techniques that are approximately $10^4$ times as many antibodies can be produced and screened in a single round, and that new specificities are generated by H and L chain combination which further increases the chance of finding appropriate antibodies.

Alternatively, monoclonal antibody fragments encompassed by the present invention can be synthesized using an automated peptide synthesizer, or by expression of full-length gene or of gene fragments in, for example, *E. coli*.

F. Pharmaceutical Compositions

Aqueous compositions of the present invention comprise an effective amount of a purified *Chlamydia* polynucleotide and/or a purified *Chlamydia* a protein, polypeptide, peptide, epitopic core region, and the like, dissolved and/or dispersed in a pharmaceutically acceptable carrier and/or aqueous medium. Aqueous compositions of gene therapy vectors expressing any of the foregoing are also contemplated.

The phases "pharmaceutically and/or pharmacologically acceptable" refer to molecular entities and/or compositions that do not produce an adverse, allergic and/or other untoward reaction when administered to an animal.

As herein, "pharmaceutically acceptable carrier" includes any and/or all solvents, dispersion media, coatings, antibacterial and/or antifungal agents, isotonic and/or absorption delaying agents and the like. The use of such media and/or agents for pharmaceutical active substances is well know in the art. Except insofar as any conventional media and/or agent is incompatible with the active ingredient, its use in the therapeutic compositions is contemplated. Supplementary active ingredients can also be incorporated into the compositions. For animal and more particularly human administration preparations should meet sterility, pyrogenicity, general safety and/or purity standards are required by FDA Office of Biologics standards.

The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular sub-cutaneous, intralesional, and/or even intraperitoneal routes, or formulated for oral or inhaled delivery. The preparation of an aqueous compositions that contain an effective amount of purified *Chlamydia* polynucleotide or polynucleotide or polypeptide agent as an active component and/or ingredient will be known to those of skill in the art in light of the present disclosure. Typically, such compositions can be prepared as injectables, either as liquid solutions and/or suspensions; solid forms suitable for using to prepare solutions and/or suspensions upon the addition of a liquid prior to injection can also be prepared; and/or the preparation can also be emulsified.

The pharmaceutical forms suitable for injectable use include sterile aqueous solutions and/or dispersions; formulations including sesame oil, peanut oil and/or aqueous propylene glycol; and/or sterile powders for the extemporaneous preparation of sterile injectable solutions and/or dispersions. In all cases the form must be sterile and/or must be fluid to the extent that easy syringability exists. It must be stable under the conditions of manufacture and/or storage and/or must be preserved against the contaminating action of microoganisms, such as bacteria and/or fungi.

Solutions of the active compounds as free base and/or pharmacologically acceptable salts can be prepared in water suitably mixed with surfactant, such as hydroxypropylcellulose. Dispersions can also be prepared in glycerol, liquid polyethylene glycols, and/or mixtures thereof and/or in oils. Under ordinary conditions of storage and/or use, these preparations contain a preservative to prevent the growth of microorganisms.

A *Chlamydia* polynucleotide or polypeptide of the present invention can be formulated into a composition in a neutral and/or salt form. Pharmaceutically acceptable salts, include the acid addition sales (formed with the free amino groups of the protein) and/or which are formed with inorganic acids such as, for example, hydrochloric and/or phosphoric acids, and/or such organic acids as acetic, oxalic, tartaric, mandelic, and/or the like. Salts formed with the free carboxyl groups can also be derived from inorganic bases such as, for example, sodium, potassium, ammonium, calcium, and/or ferric hydroxides, and/or such organic bases as isopropylamine, trimethylamine, histidine, procaine, and/or the like. In terms of using using peptide therapeutics as active ingredients, the technology of U.S. Pat. Nos. 4,608,251; 4,601,903; 4,599,231; 4,599,230; 4,596,792; and/or 4,578,770 each incorporated herein by reference, may be used.

The carrier can also be solvent and/or dispersion medium containing for example, water, ethanol, polyol (for example, glycerol propylene glycol, and/or liquid polyethylene glycol, and/or the like), suitable mixtures thereof, and/or vegetable oils.

The proper fluidity can be maintained, for example, by the use of a coating such as lecithin, by the maintenance of the required particle size in the case of dispersion and/or by the use of surfactants. The prevention of the action of microorganisms can be brought about by various antibacterial and/or antifungal agents, for example, parabens, chlorobutanol, phenol, sorbic acid, thimerosal, and/or the like. In many cases, it will be preferable to include isotonic agents, for example, sugars and/or sodium chloride. Prolonged absorption of the injectable compositions can be brought about by the use in the compositions of agents delaying absorption, for example, aluminum monostearate and/or gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the required other ingredients from those enumerated above. In the case of sterile powders for the preparation of sterile injectable solutions, the preferred methods of preparation are vacuum-drying and/or freeze-drying techniques which yield a powder of the active ingredient plus any additional desired ingredient from a previously sterile-filtered solution thereof. The preparation of more, and/or highly, concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and/or in such amount as is therapeutically effective. The formulations are easily administered in a variety of dosage forms, such as the type of injectable solutions described above, but drug release capsules and/or the like can also be employed.

For parenteral administration in an aqueous solution, for example, the solution should be suitably buffered if necessary and/or the liquid diluent first rendered isotonic with sufficient saline and/or glucose. These particular aqueous solutions are especially suitable for intravenous, intramuscular, subcutaneous and/or intraperitoneal administration. In this connection, sterile aqueous media which can be employed will be known to those of skill in the art in light of the present disclosure. For example, one dosage could be dissolved in 1 ml of isotonic NaCl solution and/or either added to 1000 ml of hypodermoclysis fluid and/or injected at the proposed site of infusion, (see for example, "Remington's Pharmaceutical Sciences" $15^{th}$ Edition, pages 1035-1038 and/or 1570-1580). Some variation in dosage will necessarily occur depending on the condition of the subject being treated. The person responsible for administration will, in any event, determine the appropriate does for the individual subject.

A *Chlamydia* polynucleotide or protein-derived peptides and/or agents may be formulated within a therapeutic mixture to comprise about 0.0001 to 1.0 milligrams, and/or about 0.001 to 0.1 milligrams, and/or about 0.1 to 1.0 and/or even about 10 milligrams per dose and/or so. Multiple does can also be administered.

In addition to the compounds formulated for parenteral administration, such as intravenous and/or intramuscular injection, other pharmaceutically acceptable forms include, e.g., tablets and/or other solids for oral administration; liposomal formulations; time release capsules; and/or any other form currently used, including crèmes.

One may also use nasal solutions and/or sprays aerosols and/or inhalants in the present invention. Nasal solutions are usually aqueous solutions designed to be administered to the nasal passages in drops and/or sprays. Nasal solutions are prepared so that they are similar in many respects to nasal secretions, so that normal ciliary action is maintained. Thus, the aqueous nasal solutions usually are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Various commercial nasal preparations are known and/or include, for example, antibiotics and/or antihistamines and/or are used for asthma prophylaxis.

Additional formulations which are suitable for other modes of administration include vaginal suppositories and/or pessaries. A rectal pessary and/or suppository may also be used. Suppositories are solid dosage forms of various weights and/or shapes, usually medicated, for insertion into the rectum, vagina and/or the urethra. After insertion, suppositories soften, melt and/or dissolve in the cavity fluids. In general, for suppositories, traditional binders and/or carriers may include, for example, polyakylene glycols and/or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soft shell gelatin capsule, and/or they may be compressed into tablets, and/or they may be incorporated directly with the food or the diet. For oral therapeutic administration, the active compounds may be incorporated with excipients and/or used in the form of ingestible tablets, buccal tables, troches, capsules, elixirs, suspensions, syrups, wafers and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

G. Kits

Therapeutic kits of the present invention are kits comprising a *Chlamydia* polynucleotide or polypeptide or an antibody to the polypeptide. Such kits will generally contain, in a suitable container, a pharmaceutically acceptable formulation f a *Chlamydia* polynucleotide or polypeptide, or an antibody to the polypeptide, or vector expressing any of the foregoing in a pharmaceutically acceptable formulation. The kit may have a single container, and/or it may have a distinct container for each compound.

When the components of the kit are provided in one and/or more liquid solutions, the liquid solution is an aqueous solution, with a sterile aqueous solution being particularly preferred. The *Chlamydia* polynucleotide or polypeptide, or antibody compositions may also be formulated into a syringeable composition. In which case, the container may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container.

The container will generally include at least one vial, test tube, flask, bottle, or syringe and/or other container, into which the *Chlamydia* polynucleotide or polypeptide, or antibody formulation are placed, preferably, suitably allocated. The kits may also comprise a second container for containing a sterile, pharmaceutically acceptable buffer and/or other diluent.

The kits of the present invention will also typically include a means for containing the vials in close confinement for commercial sale, such as, e.g., injection and/or blow-molded plastic containers into which the desired vials are retained.

Irrespective of the number and/or type of containers, the kits of the invention may also comprise, and/or be packaged with, an instrument for assisting with the injection/administration and/or placement of the ultimate *Chlamydia* polynucleotide or polypeptide, or an antibody to the polypeptide within the body of an animal. Such an instrument may be a syringe, pipette, forceps, and/or any such medically approved delivery vehicle.

H. Examples

The following examples are included to demonstrate preferred embodiments of the invention. It should be appreciated by those of skill in the art that the techniques disclosed in the examples which follow represent techniques discovered by the invention to function well in the practice of the invention, and thus can be considered to constitute preferred modes for its practice. However, those of skill in the skill in the art should, in light of the present disclosure, appreciate that many changes can be made in the specific embodiments which are disclosed and still obtain a like or similar result without departing from the spirit and scope of the invention.

Example 1

Exemplary ELI Protocol

The following sections outline general methodology that one might use to prepare, screen and utilize ELI according to the present invention. Of course the following methods are merely general guidelines and should not limit one of skill in the art form modifying the present invention to accomplish a desired goal using ELI.

1. Library Construction

The present invention provides expression library constructs of genus *Chlamydia psittaci*. An expression library of *Chlamydia psittaci* can be produced by first physically shearing genomic DNA of *Chlamydia psittaci* (e.g., *Chlamydia psittaci* strain B577) and size-selecting fragments of 300-800 base pairs. The protocol used by the present inventions to produce a *Chlamydia psittaci* library is similar to that described in Sykes and Johnston (1999). Adaptors were added and the DNA fragments ligated into a genetic immunization vector (FIG. 2) designed to link fragments to the mouse ubiquitin gene. However, the fragments can be blunt-end cloned.

This vector is known to enhance NMC class I-restricted immune responses (Sykes and Johnston, 1999), while sterilizing immunity against *Chlamydia* is thought to be MHC class II-dependent (Morrison et al., 1995). However, any genetic immunization procedure, by the mechanism of intracellular expression of the inserted genes, will target towards class I antigen presentation. Nevertheless, both MHC class I- and class II-restricted immune responses to the expressed antigens are well documented (Barry et al., 1995; Sykes and Johnston, 1999). The inventors observed, for instance, pronounced delayed-type hypersensitivity responses, mediated by MHC II-restricted CD4$^+$ Th1 cells, against protective *Chlamydia psittaci* B577 antigens, antigens, which were expressed from the ubiquitin fusion vector. In addition to the fact that MHC II-restricted immunity is generated by the ubiquitin fusion vector, NMC I-restricted immunity appears to mediate protection in the early phase of chlamydial infection (Morrision et al., 1995; Rottenberg et al., 1999). This duality of the cellular immune response generated by the ubiquitin fusion vector might explain the efficacy of this vector for genetic immunization against intracellular bacteria.

A library of approximately 82,000 individual members was created and tested as 27 sub-libraries each with 2,400-3,400 plasmid clones. The average insert frequency was approximately 67% and the average insert size was 660 base pairs. Nitrocellulose replica filters were made of each original colony plating of a sub-library pool for subsequent retrieval of positive clones. This generated a library with approximately six-fold expression-equivalent redundancy. One expression equivalent is defined as the number of in-frame fragments necessary to completely represent all authentic open reading frames. Since the genome size of *Chlamydia psittaci* is approximately $1\times10^6$ base pairs and only one-sixth of the actual open-reading frames will be cloned in the right orientation and frame, it requires at least six genomic equivalent to encode one expression equivalent. Each sub-library was propagated on plates and harvested to prepare DNA. DNA representing each sub-library was used for genetic immunization of mice in the following section.

2. Vaccination and Challenge

For the first round of testing, outbread, 6-week old, female NIH-Swiss Webster mice are inoculated with the purified DNA of each sub-library using both intra-muscular (i.m.) and epidermal injection. The epidermal injection was effected with a gene gun (Sanford et al., 1991). Each mouse was given 50 μg DNA by gene gun. It has been argued that the gene gun immunization favors a Th2 and the i.m. injection a Th1 type response (Feltquate et al., 1997), therefore both types of injection were given to each group. In the first round of testing, the prime inoculation was followed by a boost 9 weeks later, before intranasal challenge with $3\times10^6$ inclusion forming units (IFU) of *Chlamydia psittaci* strain B577 13 weeks after prime inoculation. The animals were sacrificed 12 days after the challenge, and lungs were weighed.

3. Library Deconvolution

Figure 3:
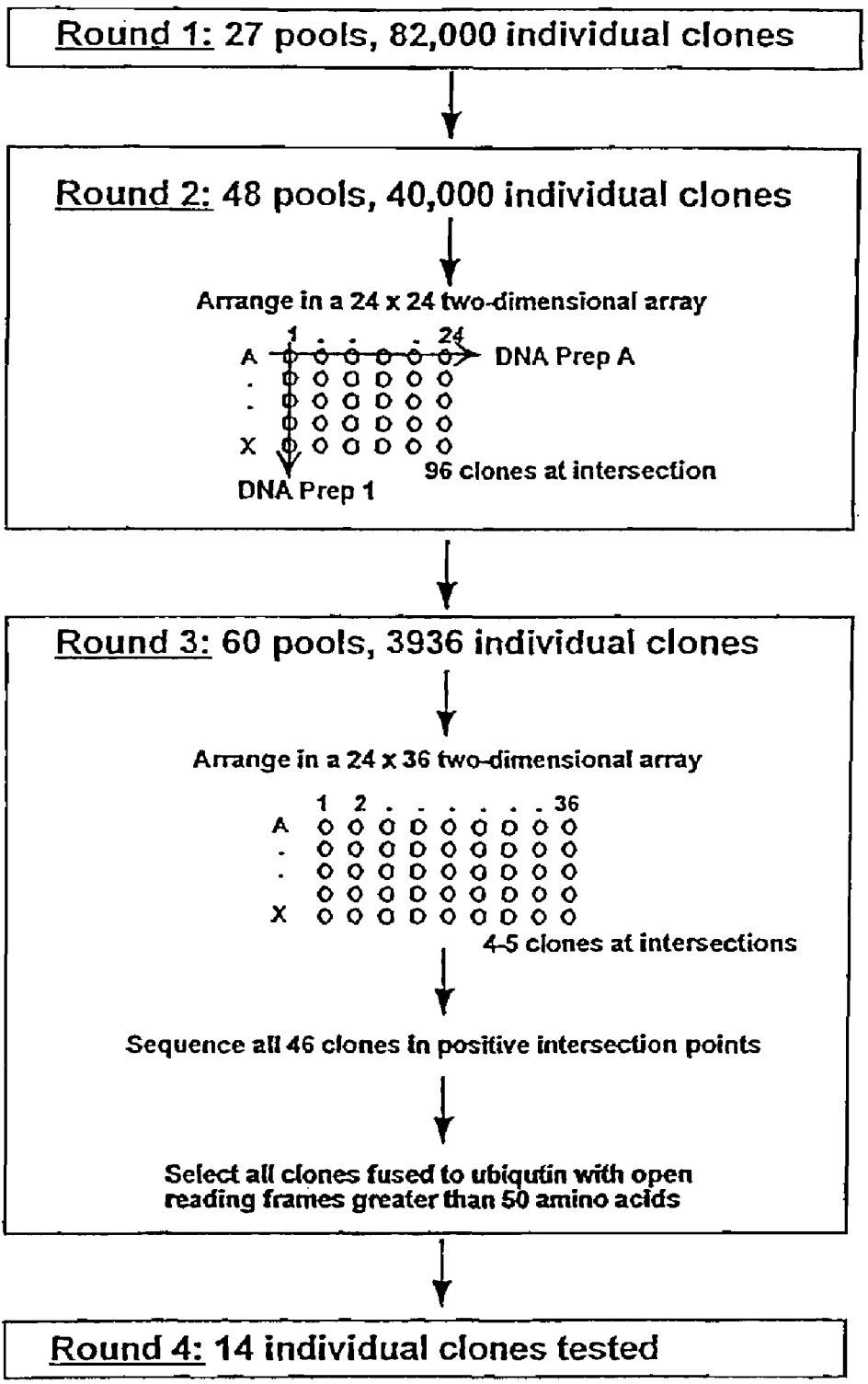
FIG. 3. Flowchart depicting the process for deconvolution of the libraries. Each round consists of preparation of DNA samples, vaccination of mice, challenge and determination of the relative protection in each group.

The basic scheme for handling the reduction of the libraries is depicted in FIG. 3. Fourteen groups out of the first round looked promising, so the individual clones form these groups out of the first round looked promising, so the individual clones from these groups were picked and grown in 96 well microtiter plates. This gave approximately 40,000 wells in microtiter plates, therefore about 40,000 clones. The second round was reduced using a two dimensional array format. As depicted in FIG. 3, the DNA was prepared from colonies pooled form rows and columns of the array. The rationale was that if a row and column conferred protection, the colonies at the intersection would be responsible. This scheme is premised on largely additive effects of the protective clones. This 24×24 array yielded pools of ~1,700 clones with each intercession having ~96 clones. Currently the inventors deconvolute the second round with a 3-dimensional array.

Since the lung weight was highly variable in the outbred NIH-Swiss mice with variable MHC background, the inventors decided to use inbred BALB/c mice in subsequent rounds. The 48 DNA pools for round two were i.m. injected into BALB/c mice at 50 μg DNA/animal, and the animals were boosed at seven weeks by both gene gun inoculation and i.m. injection. The mice were given a higher *Chlamydia psittaci* challenge, $1.6\times10^6$ IFU *Chlamydia psittaci* B577, at approximately 12 weeks, again to further differentiate the groups. Animals were sacrificed and results evaluated as in round one.

Figure 5:
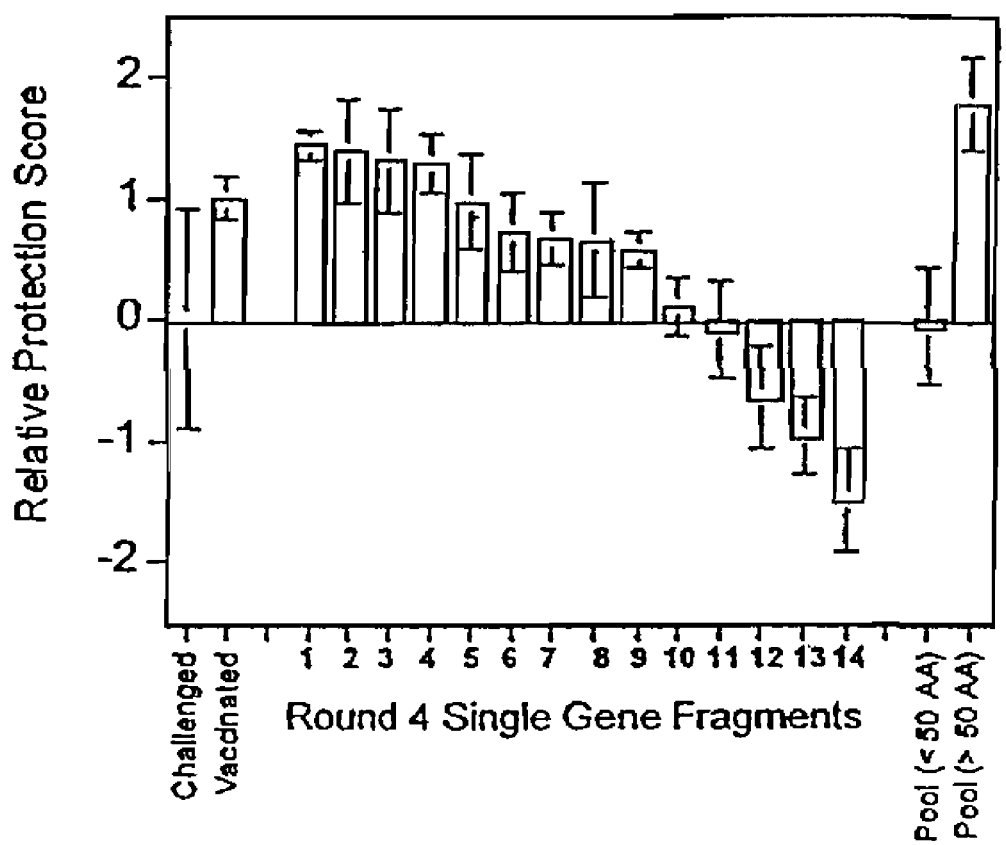
FIG. 5. Results of protection assays of testing individual gene fragments in Round 4. Protection was scored as lung weight relative to the average of the vaccinated, maximum protection, positive control (Vaccinated=1) and the non- the non-vaccinated, challenged, maximum disease, negative control (Challenged=0). The Pool<50 AA is the DNA consisting of the pool of the 32 plasmids from Round 3 having predicted open-reading frames less than 50 amino acids long. Pool>50 AA is the DNA consisting of all the 14 plasmids containing *Chlamydia psittaci* inserts encoding in-frame proteins more than 50 amino acids long. The numbers each individual gene fragment tested correspond to the numbers in FIG. 4. The error bars represent one standard deviation of the mean.

In the fourth round, the animals received two boosts rather than one, and the challenge inoculum was increased to $3\times10^6$ IFU *Chlamydia psittaci* B577 to increase the selectivity of protection scoring. Furthermore, because too much DNA may lead to a decrease in cellular immune response, the amount of each individual close was reduced by half, with the difference made up with pUC118 DNA, so each mouse received a total 50 μg DNA for i.m. immunization, but only 25 μg/ear of the μg/ear of the specific clone and 1.25 μg pUC118. Mice were boosted i.m. at both four and nine weeks after prime inoculation, and were challenged. The results of this final round are depicted in FIG. 5.

The experiment of FIG. 5 was designed as follows. First, groups of mice (1-14) were genetically immunized with constructs that contained *C. psittaci* DNA inserts that coded for open reading frames of more than 50 amino acids, that had been identified in previous rounds of the screen as described, above, and were considered potential vaccine candidates. The inventors made the reasonable assumption that the inserts were in the correct coding frame because they coded for peptides that were longer than 50 amino acids. It is highly unlikely that incorrect open reading frames would code for such long peptides, because open reading frames of random, incorrect inserts would be terminated much earlier, i.e. before 50 amino acids (AA), by a random stop codon.

The control groups for the genetic immunization were designed to imitate, as closely as possible, the assumedly correct inserts. To that end, all vaccine plasmids from the previous round that contained presumably correct coding inserts of more than 50 amino acids were pooled and considered the positive control for genetic immunization [pool (>50 AA)]. All vaccine plasmids with inserts coding for peptides of less than 50 amino acids were considered random irrelevant clones and pooled into another control group and considered the negative control for genetic immunization [pool (<50 AA)].

Two other groups of control mice did not receive any genetic immunization and were considered calibration controls that allowed determining the amount of immune protection achievable under conditions of natural infection without vaccination. The first group was labeled "Vaccinated," and contained mice that received a low-dose intranasal inoculation with *C. psittaci* 4 weeks prior to the high-dose challenge. This low-dose inoculation did not cause disease but elicited strong specific immunity against *C. psittaci*. The effect of this low-dose challenge was that these mice showed immunity equivalent to previous natural infection and infection and were highly protected against the high-dose challenge with *C. psittaci* 4 weeks later. The immune protection of this group from the high-dose challenge infection was considered the highest possible protective immunity and arbitrarily set at a protection score of 1 (100% protection).

To calibrate the range of protection, a second group of mice designated as "Challenged" was used. These mice received a shaminoculum 4 weeks prior to the high-dose *C. psittaci* challenge, and thus were completely un-exposed to *C. psittaci* (immunologically naïve) prior to high-dose challenge, and were considered non-protected from the challenge infection. The immune protection of this group from the high-dose challenge infection was considered the lowest possible protective immunity and arbitrarily set at a protection score of 0 (0% protection).

The interpretation of the results demonstrated in FIG. 5 indicates that i) genetic immunization constructs 1-5 of more than 50 AA coding inserts achieved protection from *C. psittaci* better than that achievable with previous low-dose natural infection; that ii) the positive genetic immunization control pool (>50 AA) of all assumed correctly coding genetic immunization constructs also protected better than protection naturally achievable; and, importantly, that iii) the negative genetic immunization control pool (<50 AA) of all incorrect coding constructs did not protect the mice.

4. Analysis of Sequences

Figure 6:
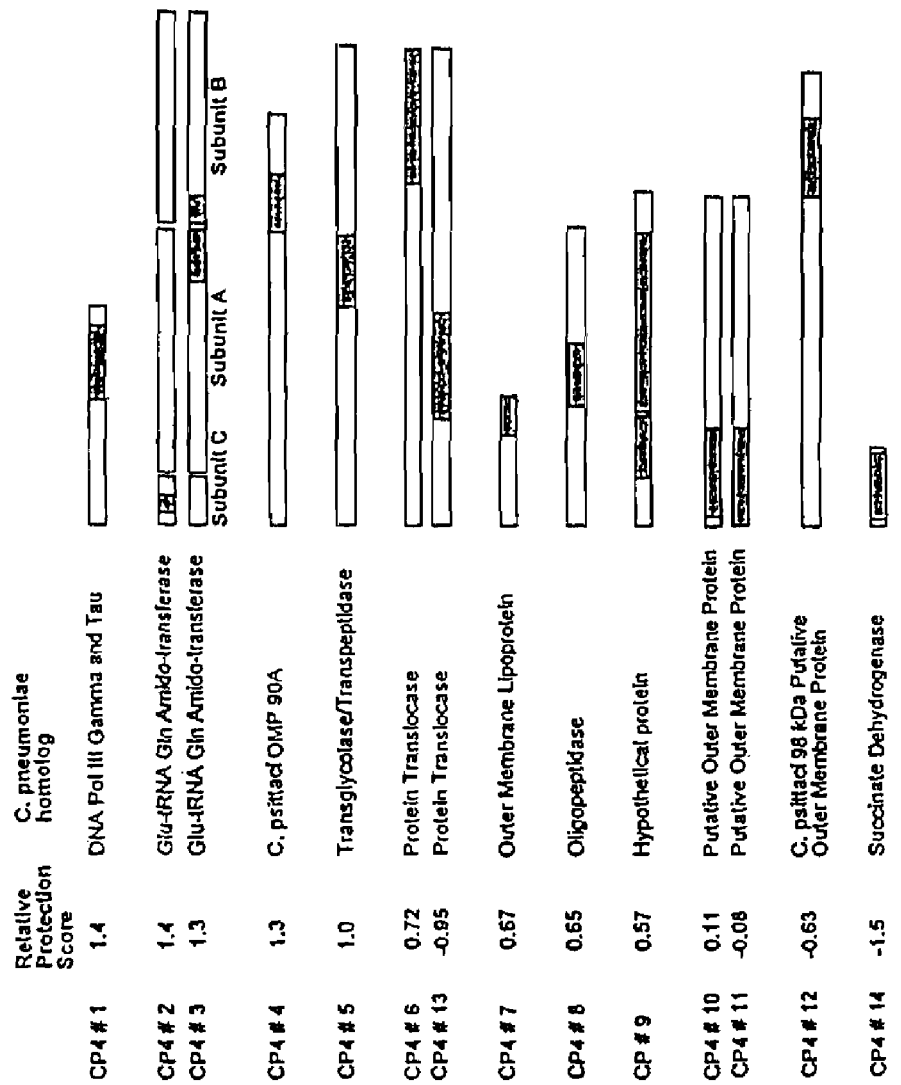
FIG. 6 Summary of characterization of the single gene fragments of Round 4. The Relative Protection score of each *Chlamydia psittaci* (CP) gene fragment is provided along with the designation of the gene in *Chlamydia pneumonia* that has the highest similarity (Chlamydia pneumonia homologue). In two cases, gene fragment CP #4 and CP #12, the *Chlamydia psittaci* gene could also be identified. On the right is a linear map showing the location in each gene of the fragment that conferred protection (shaded).

The clones conferring protection were re-sequenced and then compared by BLAST search to Genbank and particularly to the recently completed *Chlamydia pneumoniae* (Kalman et al., 1999) genome sequences (FIG. 6). Of the 14 single genes identified in this study, ten are internal fragments and three contain the C-terminus of the protein. Of the five most protective clones, one was from a putative outer membrane protein and one was from a cell surface protein. The other three were from cytosolic proteins.

Four of the 14 clones have sequence similarity to a class of proteins known as putaive outer membrane proteins (POMPs) in *Chlamydia psittaci* and *Chlamydia pneumoniae*. Many of the "putative" outer membrane proteins are known to be localized to the outer membrane and to be highly immunogenic (Longbottom et al., 1996; Tan et al., 1990).

5. Mixing Experiment

Figure 7:
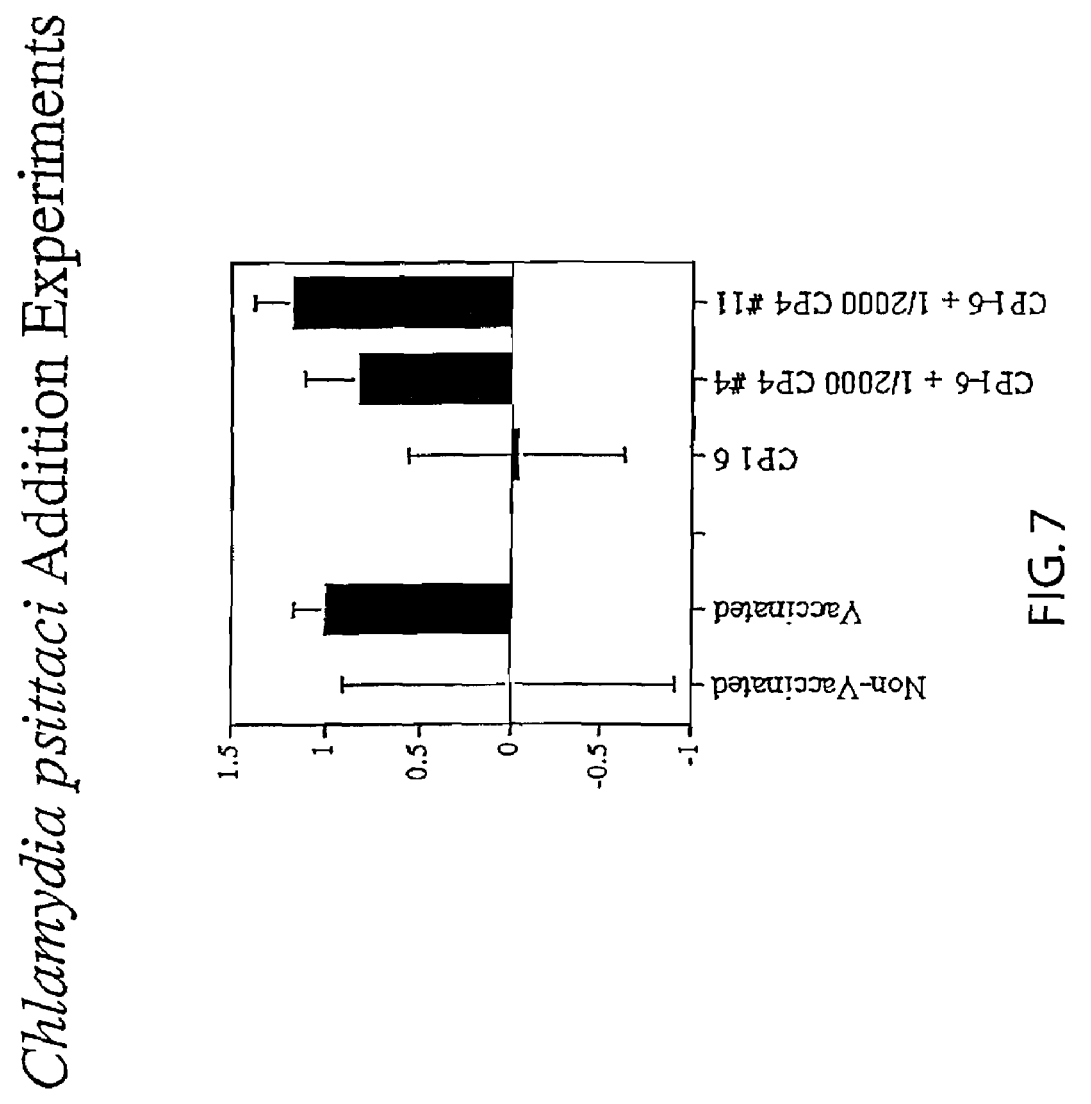

The two dimensional approach used to find protective gene fragments assumes that the protection is due to a single highly protective gene within a pool. To verify that such genes would be found, 25 ng (i.e. ½₀₀₀) of either of the two most protective genes was added to a pool that scored negative (pool 6 round 1). As depicted in FIG. 7, spiking with either clone converted the negative library to a positive.

Example 2

Materials and Methods

Library construction. *Chlamydia psittaci* strain B577 (ATCC VR-656) was grown in BGMK cells and elementary bodies (EB) were purified by renograff gradient centrifugation as described (Huang et al., 1999). Genomic DNA was isolated from EB by proteinase K and RNase digestion followed by cetyl-trimethyl ammonium bromide (Kaltenbock et al., 1997).

Genomic DNA was physically sheared using a nebulizer (Glas Col, Terra Haute, Ind.), then size fractioned on a 1.5% TBE agarose gel. Agarose with fragments between 300-700 base pairs was excised and the DNA was electroeluted. Adaptors (top strand 5': GATCTGGATCCCGAT (SEQ ID NO:2) ATCGGGCTCCA (SEQ ID NO:3) onto the fragments, then the fragments were cloned into pCMVi-UBs at the Bgl II site (See FIG. 6 and Sykes and Johnston, 1999 for more details). The ligations were transformed into DH 5 alpha electrocompetent cells and plated onto 150 mm diameter YT-Ampicillin (75 µg/mL final concentration) plates. The resulting plates had between 2400-3400 individual clones per plate. After plates were incubated overnight at 37° C., the colonies from were lifted using nitrocellulose filters soaked in L-Broth with 8% DMSO, and these filters were stored at −80° C. The original agar plates at −80° C. The original agar plates were then incubated at 37° C. for an additional six hours. Ten mL of L Broth was added to each plate, the *E. coli* was scraped into 150 mL of L-Broth and grown at 37° C. for 30 minutes. Ampicillin was then added to a final concentration of 50 µg/mL, and the cultures were grown overnight at 37° C. Cells were pelleted and the DNA was purified using Qiagen tip 500 columns.

Inoculation of DNA. Round One: DNA from the pools was injected into 6-week old female NIH-Swiss mice. All mice received 50 µg total DNA by i.m. injections, evenly distributed between the quadriceps and tibialis anterior muscles. Eighteen of the groups also received gene gun inoculations (wand), with 2.5 µg DNA inoculated into each ear. The animals were boosted once at nice weeks in the same manner as the primary inoculation—all mice received i.m. injections, but only the same 18 groups received gene gun injections—then intranasally challenged with $5.5 \times 10^5$ IFU of *Chlamydia psittaci* strain B577 at 13 weeks. The mice were sacrificed 11 days after the challenge, and lungs were weighed.

Figure 2:
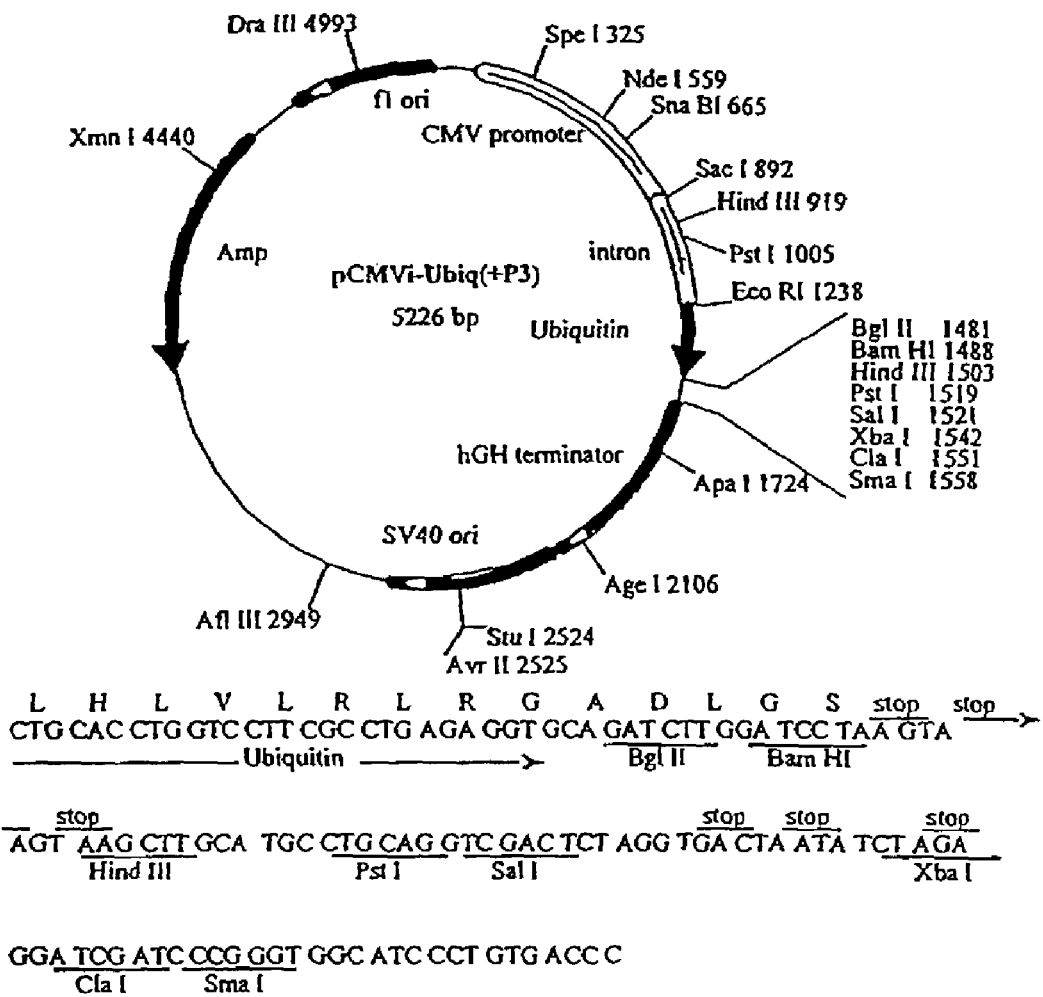
FIG. 2. Production of the *Chlamydia psittaci* Library. The *Chlamydia psittaci* library was produced by first physically shearing the genomic DNA, strain BGM/B577, and size selecting fragments of 300-800 base pairs. The fragments were ligated into the Bgl II site of pCMVi-Ubs(+P3); see Sykes and Johnson, 1999 for details. The nucleotide sequence shown in this figure is given as SEQ ID NO:1.

Round Two: Nitrocellulose filters from the positive pools were placed on L-Broth Bio-Assay plates were supplemented with 75 µg/mL ampicillin and 2% agar. The filters were incubated on the plates for approximately 15 minutes, then the nitrocellulose was discarded. The colonies were hand-picked. The microtiter plates were designated by their original pool number and by the order in which they were picked. Hence, plate 5.10 was from original pool 5 and was the tenth plate picked. The colonies were subdivided into groups as is indicated in FIG. 2. All of the microtiter plates comprising a pool were stamped onto on L-Broth Bio-Assay plates supplemented with 75 µg/mL ampicillin and were grown overnight at 37° C. The cells from these plates were harvested by adding L-Broth to the plates and scraping off the cells. The cells were pelleted by centrifugation then resuspended in Qiagen buffer P1. The remainder of the DNA prep proceeded according to manufacture's instructions.

These 48 DNA pools were i.m. injected into 6-week old BALB/c mice at 50 µg DNA/animal. For the initial inoculation, the mice did not receive gene receive gene gun inoculations. At seven weeks, the mice were boosted with 50 µg DNA/animal. In addition to the i.m. injections, the first 31 groups received gene gun (Rumsey-Loomis) inoculations at 2.5 µg DNA/ear; however, the gene gun failed at group 32, and the last 17 groups received only i.m. injections. The mice were given a higher challenge, $1.6 \times 10^6$ IFU *Chlamydia psittaci* B577, at 12 weeks. Animals were sacrificed as in round one Round Two: Nitrocellulose filters from the positive pools were placed on L-Broth Bio-Assay plates supplemental with 75 µg/mL ampillin and 2% agar. The filters were incubated on the plates for approximately 15 minutes, then the nictrocellulose was discarded. The colonies were grown at 30° C. for 12 hours. The majority of the colonies were picked into 96 well microtiter plates containing HYT media (1.6% Bacto-tryptone, 1.0% Bacto-yeast extract, 85.5 mM NaCl, 36 mM $K_2HPO_4$, 1.7 mM Sodium citrate, 0.4 mM MgSO4, 6.8 mM ammonium sulfate, 4.4% wt/vol glycerol) supplemented with 75 μg/mL ampicillin, using a Hybaid colony picker; the plates were then visually inspected and the remainder of the colonies were handpicked. The microtiter plates were designated by their original pool number and by the order in which they were picked. Hence, plate 5.10 was from original pool 5 and was the tenth plate picked. The colonies were subdivided into groups as is indicated in FIG. 2. All of the microtiter plates comprising a pool were stamped onto on L-Broth Bio-Assay plates supplemented with 75 μg/mL ampicillin and were grown overnight at 37° C. for 12 hours. The cells from these plates were harvested by adding L-Broth to the plates and scraping off the cells. The cells were pelleted by centrifugation then resuspended in Qiagen buffer P1. The remainder of the DNA prep proceeded according to manufacture's instructions.

These 48 DNA pools were i.m. injected into 6-week old BALB/c mice at 50 μg DNA/animal. For the initial inoculation, the mice did not receive gene gun inoculations. At seven weeks the mice were boosted with 50 μg DNA/animal. In addition to the i.m. injections, the first 31 groups received gene gun (Rumsey-Loomis) inoculations at 2.5 μg DNA/ear; however the gene gun failed at group 32, and the last group 32, and the last 17 groups received only i.m. injections. The mice were given a higher challenge, $1.6 \times 10^6$ IFU Chlamydia psittaci B577, at 12 weeks. Animals were sacrificed as in round one.

Round Three. Colonies from the microtiter plates that were judged to be positive were arrayed as in FIG. 2. For each pool, new microtiter plates with HYT media supplemented with 75 μg/mL ampicillin were constructed from all the colonies which comprise the. Colonies were grown and DNA prepared as in round two.

The mice received both gene gun (wand) and i.m. inoculations at the dosage indicated above. At six weeks, the mice were boosted with 50 μg DNA/animal, but only by i.m. injections. The challenge schedule was the same as in Round Two.

Round Four: E. coli from wells at either full by full protection or full by partial protection was streaked out onto YT-plates supplemented with 75 μg/mL ampicillin. Six colonies from each of the plates were tested by PCR colony screening, using the primers FS-UB 5': CCGCACCCTCTCGATTAC (SEQ ID NO: 4) CTGGAGTGGCAAGTTCC. (SEQ ID NO: 5) Colonies with different sizes, hence different inserts, were sequenced using ABI Big Dye terminator and the FS-UB primer. Samples were purified on G-50 spin columns, and run on an ABI 377 Sequencer. The generated sequences were analyzed for open reading frames using a program designed by Simon Raynor, Ph.D.

Example 3

Vaccination and Challenge

Figure 4:
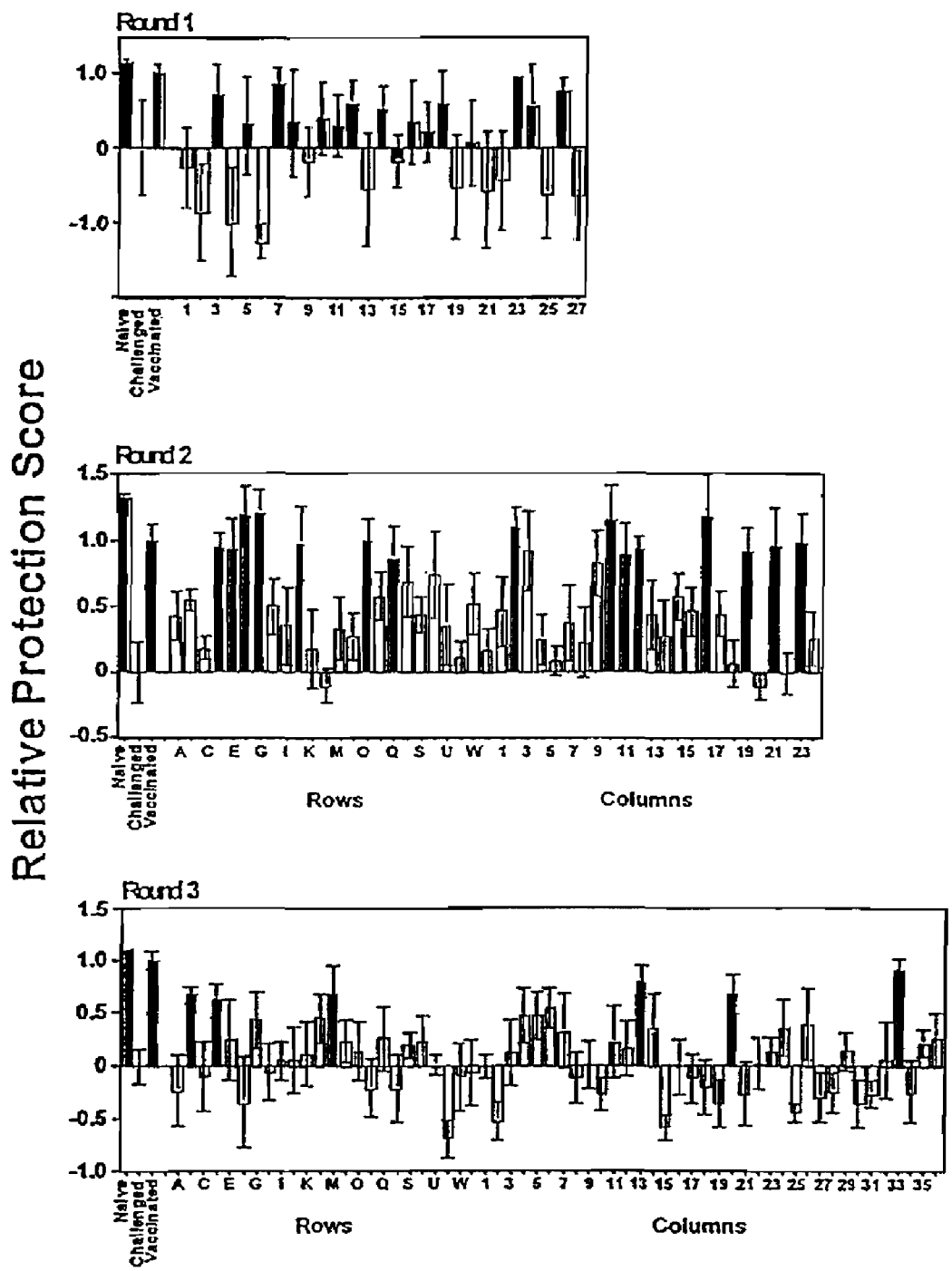
FIG. 4. Results of protection assays in Rounds 1, 2 and 3. Protection was scored as lung weight relative to average of the vaccinated, maximum protection, positive control and the non-vaccinated, challenged, maximum disease, negative control. The relative protection score was calculated by assigning the score 1 to animals with lung weight equal to the vaccinated control and the score 0 to animals with lung weights equal to the challenged, non-vaccinated control. These points define a line; animals with lower lung weight, hence better protection, have a higher relative protection score. Animals that have worse disease than challenged, non-vaccinated controls, i.e., heavier lungs, will have a negative relative protection score. The unchallenged Naïve group consistently had lung weights slightly lower than maximum protection, positive controls (Vaccinated) due to the peribronchiolar accumulation of lymphatic cells. In Rounds 2 and 3 the pools of plasmids from columns in the two-dimensional arrays are assigned numbers and the rows assigned letters. The solid bars indicate pools that were designated as protective and entered into the subsequent round. The error bars represent one standard deviation on either side of the mean.

It was established that the weight increase of the infected lung over the lung weight of naïve uninfected controls (~120 mg) correlated strongly with disease intensity. Maximum disease in this module resulted in approximately 250% lung weight increase, while further lung weight increases were lethal. The lung disease on day 12 after inoculation was characterized by areas of gross lung tissue consolidation and the presence of mononuclear interstitial infiltrates in consolidated tissue. Chlamydial inclusions were observed by immunohistochemistry in may macrophages, but rarely in other cells. Controls for complete protection were established by low level intranasal infection of naïve mice with $3 \times 10^4$ IFU Chlamydia psittaci strain B577 4 weeks prior to challenge. These mice were completely protected from disease after challenge infection and had lung weight increases of 10-30% compared to naïve animals. Lungs of completely protected mice did not show gross lung lesions, and pathohistological examination revealed no interstitial infiltrates, but prominent peribronchiolar lymphocytic cuffs, interpreted as sign of protective immune stimulation. The chlamydial lung burden on day 11 after challenge was typically $1-3 \times 10^6$ IFU per 100 mg lung tissue in protected, and $2-6 \times 10^6$ IFU per 100 mg lung in diseased animals. Since the lowest chlamydial burden was, however, not consistently associated with lowest disease, the inventors used the disease-dependent parameter lung weight rather than chlamydial burden as readout for evaluation of protection. The lung weights were transformed to relative protection scores in a linear equation that assumed the high average lung weight of severely ill, naïve, challenged mice as 0 and that of fully protected controls as 1 (FIG. 4).

Example 4

Deconvolution of the Libraries

Since the lung weight was highly variable in the outbred NIH-Swiss mice with variable MHC background, the inventors decided to use inbread BALB/c mice in subsequent rounds. The 48 DNA pools for round two were i.m. injected into BALB/c mice at 50 μg DNA/animal, and the animals were boosted at seven weeks by both gene gun inoculation and i.m. injection. The mice were given a higher Chlamydia psittaci challenge, $1.6 \times 10^6$ IFU Chlamydia psittaci B577, at approximately 12 weeks, again to further differentiate the groups. Animals were sacrificed and results evaluated as in round one.

The results of the Round two challenge are depicted in FIG. 4. Of the 48 groups from round two, 15 were judged to be positive, giving a total of 3936 wells. These wells were again arrayed as in round two, but the array had 112 colonies per column and 156 per row with 4-5 colonies per intersection (See FIG. 3). The mice received both gene gun and i.m. injections at the dosage indicated above. At six weeks, the mice were boosted. Both the challenge and the sacrifice were performed as in Round two.

The positive 46 colonies from the intersection wells from Round three were sequenced, and those clones with open reading frames greater than 50 amino acids long were prepared individually and shot into mice as single genes and as a pool. Fourteen clones met these criteria. The disease scoring on each pool in rounds 1-3 are depicted in FIG. 4.

In the fourth round, the animals received two boosts rather than one, and the challenge inoculum was increased to $3 \times 10^6$ IFU Chlamydia psittaci B577 to increase the selectivity of protection scoring. Furthermore, because too much DNA may lead to a decrease in cellular immune response, the amount of each individual clone was reduced by half but made up the difference with pUC118 DNA, and each mouse received a total 50 μg DNA for i.m. immunization, but only 25 μg of the specific clone. The inventors also decreased the gene gun DNA in the same manner: 1.25 μg of the specific clone. The inventors also decreased the gene gun DNA in the same manner: 1.25 μg/ear of the specific clone and 1.25 μg pUC118. Mice were boosted i.m. at both four and nine weeks after prime inoculation, and were challenged. The results of this final round are depicted in FIG. 5.

Example 5

Comparison of Clones

Based on the hypothesis that sequences from genes conferring a high level of protection might be selected more than once in the ELI process, the clone were compared against each other for overlaps. Interestingly, one of the clones, CP4 CP4 #10, did overlap with another gene, CP4 #11. The gene from which these two clones arise had been partially sequenced (Longbottom et al., 1998).

Two of the genes, CP4 #5 and CP #9, had an overlapping region, but they were fused to ubiquitin in opposite orientations. CP4 #5, is composed of two different *Chlamydia psittaci* DNA fragments, fused in opposite orientations. The first gene is fused to ubiquitin in the correct orientation and the correct reading frame. Interestingly, the second gene, which is in the opposite orientation to the ubiquitin gene, has an overlapping sequence to CP4 #5. It is doubtful that the protein from the second gene is produced in the mouse.

Example 6

Analysis of Sequences

The clones conferring protections were re-sequenced and then compared by BLAST search to Genbank and particularly to the recently completed *Chlamydia pneumoniae* (Kalman et al., 1999) genome sequences (FIG. 6). The full-length *Chlamydia psittaci* genes were next isolated and sequences. Upon analysis, all nucleic acid sequences, except #4, #10, #11, and #12, were previously undisclosed in any context. Further, only portions of the sequences encoding #10 and #11 were previously disclosed.

Since most protective genes would not have been predicted by any bioinformatics or information-based approach, it is likely that one will need to apply an unbiased, global approach such as ELI to define vaccine candidates.

Table 2, lists a comparison of the *Chlamydia psittaci* genes with homologues from *Chlamydia trachomatis* and *Chlamydia pneumoniae*.

TABLE 2

| | *Chlamydia ps* | *Chlamydia trachomatis* | Identity/ Similarity | *Chlamydia pneumoniae* | Indentity/ Similarity |
|---|---|---|---|---|---|
| CP4 #1 | | DNA Pol III Gamma and Tau | 62/73 | DNA Pol III Gamma and Tau | 66/76 |
| CP4 #2 | | Glu-tRNA Gln Amido-transferase (C subunit) | 49/70 | Glu-tRNA Gln Amido-transferase (C subunit) | 48/63 |
| CP4 #3 | | Glu-tRNA Gln Amido-transferase (A subunit) | 71/85 | Glu-tRNA Gln Amido-transferase (A subunit) | 71/84 |
| CP4 #4 | OMP 90A | Outer Membrane Protein 5 | 30/45 | Outer Membrane Protein G Family | 40/54 |
| CP4 #5 | | Transglycolase/transpeptidase | 67/80 | Transglycolase/transpeptides | 67/77 |
| CP4 #6 | | Protein Translocase | 80/89 | Protein Translocase | 84/92 |
| CP4 #7 | | | | Outer Membrane Lipoprotein | 60/79 |
| CP4 #8 | | Oligopeptidase | 60/75 | Oligopeptidase | 61/74 |
| CP4 #9 | | Hypothetical protein | 62/76 | Hypothetical protein | 62/77 |
| CP4 #10 | | Outer Membrane Protein 4 | 27/42 | Outer Membrane Protein G family | 33/51 |
| CP4 #11 | | Outer Membrane Protein 4 | 27/42 | Outer Membrane Protein G family | 33/51 |
| CP4 #12 | OMP 98 kDa | Outer Membrane Protein 5 | 30/43 | Outer membrane Protein G family | 44/58 |
| CP4 #13 | | Protein Translocase | 80/89 | Protein Translocase | 84/92 |
| CP4 #14 | | Succinate Dehydrogenase | 60/76 | Succinate Dehydrogenase | 61/77 |

Table 3 lists all of the cloned fragments, their corresponding full length nucleotide sequences, and the amino acid sequences encoded by both the fragments and the full length sequences. Table 2 further describes the fragments.

TABLE 3

| SEQUENCE LISTING INDEX | | |
|---|---|---|
| SEQ ID NO | CP4 NO | Description |
| SEQ ID NO: 6 | CP4 #1 | (fragment) homolog to *Chlamydia pneumoniae* DNA Pol III Gamma and Tau subunits (dnaX2 gene) |
| SEQ ID NO: 7 | CP4 #1 | Polypeptide translation corresponding to SEQ ID NO. 6, homolog to *Chlamydia pneumoniae* DNA Pol III Gamma and Tau subunits (dnaX2 gene) |
| SEQ ID NO: 8 | CP4 #1 | (full length) homolog to *Chlamydia pneumoniae* DNA Pol III Gamma and Tau subunits (dnaX2 gene) |
| SEQ ID NO: 9 | CP4 #1 | Polypeptide translation corresponding to SEQ ID NO. 8, homolog to *Chlamydia pneumoniae* DNA Pol III Gamma and Tau subunits (dnaX2 gene) |
| SEQ ID NO: 10 | CP4 #2 | (fragment) homolog to *Chlamydia pneumoniae* Glu-tRNA Gln Amido-transferase (C subunit) (gatC gene) |
| SEQ ID NO: 11 | CP4 #2 | Polypeptide translation corresponding to SEQ ID NO. 10, homolog to *Chlamydia pneumoniae* Glu-tRNA Gln Amido-transferase (C subunit) (gatC gene) |

TABLE 3-continued

| SEQUENCE LISTING INDEX | | |
|---|---|---|
| SEQ ID NO | CP4 NO | Description |
| SEQ ID NO: 12 | CP4 #2 | (full length) homolog to *Chlamydia pneumoniae* Glu-tRNA Gln Amido-transferase (C subunit) (gatC gene) |
| SEQ ID NO: 13 | CP4 #2 | Polypeptide translation corresponding to SEQ ID NO. 12, homolog to *Chlamydia pneumoniae* Glu-tRNA Gln Amido-transferase (C subunit) (gatC gene) |
| SEQ ID NO: 14 | CP4 #3 | (fragment) homolog to *Chlamydia pneumoniae* Glu-tRNA Gln Amido-transferase (A subunit) (gatA gene) |
| SEQ ID NO: 15 | CP4 #3 | Polypeptide translation corresponding to SEQ ID NO. 14, homolog to *Chlamydia pneumoniae* Glu-tRNA Gln Amido-transferase (A subunit) (gatA gene) |
| SEQ ID NO: 16 | CP4 #3 | (full length) homolog to *Chlamydia pneumoniae* Glu-tRNA Gln Amido-transferase (A subunit) (gatA gene) |
| SEQ ID NO: 17 | CP4 #3 | Polypeptide translation corresponding to SEQ ID NO. 16, homolog to *Chlamydia pneumoniae* Glu-tRNA Gln Amido-transferase (A subunit) (gatA gene) |
| SEQ ID NO: 18 | CP4 #3 | (full length) homolog to *Chlamydia pneumoniae* Glu-tRNA Gln Amido-transferase (B subunit) (gatB gene) |
| SEQ ID NO: 19 | CP4 #3 | Polypeptide translation corresponding to SEQ ID NO. 18, homolog to *Chlamydia pneumoniae* Glu-tRNA Gln Amido-transferase (B subunit) (gatB gene) |
| SEQ ID NO: 20 | CP4 #4 | (fragment) homolog to *Chlamydia psittaci* 90 kDa outer membrane protein (OMP90A gene) (Previously sequenced by Longbottom et al.); homolog to *Chlamydia pneumoniae* Outer membrane Protein G/I (pmp 9) and Outer Membrane Protein G (pmp 5) |
| SEQ ID NO: 21 | CP4 #4 | Polypeptide translation corresponding to SEQ ID NO. 20, *Chlamydia psittaci* 90 kDa outer membrane protein (OMP90A gene); homolog to *Chlamydia pneumoniae* Outer Outer membrane Protein G/I (pmp 9) and Outer Membrane Protein G (pmp 5) |
| SEQ ID NO: 22 | CP4 #4 | (full length) *Chlamydia psittaci* 90 kDa outer membrane protein (OMP90A gene); homolog to *Chlamydia pneumoniae* Outer membrane Protein G/I (pmp 9) and Outer Membrane Protein G (pmp 5) |
| SEQ ID NO: 23 | CP4 #4 | Polypeptide translation corresponding to SEQ ID NO. 22, *Chlamydia psittaci* 90 kDa outer membrane protein (OMP90A gene); homolog to *Chlamydia pneumoniae* Outer membrane Protein G/I (pmp 9) and Outer Membrane Protein G (pmp 5) |
| SEQ ID NO: 24 | CP4 #5 | (fragment) homolog to *Chlamydia pneumoniae* transglycolase/transpeptidase (pbp3 gene) |
| SEQ ID NO: 25 | CP4 #5 | Polypeptide translation corresponding to SEQ ID NO. 24, homolog to *Chlamydia pneumoniae* transglycolase/transpeptidase (pbp3 gene) |
| SEQ ID NO: 26 | CP4 #5 | (full length) homolog to *Chlamydia pneumoniae* transglycolase/transpeptidase (pbp3 gene) |
| SEQ ID NO: 27 | CP4 #5 | Polypeptide translation corresponding to SEQ ID NO. 26, homolog to *Chlamydia pneumoniae* transglycolase/transpeptidase (pbp3 gene) |
| SEQ ID NO: 28 | CP4 #6 | (fragment) homolog to *Chlamydia pneumoniae* Protein Translocase (secA2 gene) |
| SEQ ID NO: 29 | CP4 #6 | Polypeptide translation corresponding to SEQ ID NO. 28, homolog to *Chlamydia pneumoniae* Protein Translocase (secA2 gene) |
| SEQ ID NO: 30 | CP4 #13 | (fragment) homolog to *Chlamydia pneumoniae* Protein Translocase (secA2 gene) |
| SEQ ID NO: 31 | CP4 #13 | Polypeptide translation corresponding to SEQ ID NO. 30 homolog to *Chlamydia pneumoniae* Protein Translocase (secA2 gene) |
| SEQ ID NO: 32 | CP4 #6 & 13 | (full length) homolog to *Chlamydia pneumoniae* Protein Translocase (secA2 gene) |
| SEQ ID NO: 33 | CP4 #6 & 13 | Polypeptide translation corresponding to SEQ ID NO. 32, homolog to *Chlamydia pneumoniae* Protein Translocase (secA2 gene) |
| SEQ ID NO: 34 | CP4 #7 | (fragment) homolog to *Chlamydia pneumoniae* Outer Membrane Lipoprotein (Cpn 0278) |
| SEQ ID NO: 35 | CP4 #7 | Polypeptide translation corresponding to SEQ ID NO. 34, homolog to *Chlamydia pneumoniae* Outer Membrane Lipoprotein (Cpn 0278 gene) |
| SEQ ID NO: 36 | CP4 #7 | (full length) homolog to *Chlamydia pneumoniae* Outer Membrane Lipoprotein (Cpn 0278) |
| SEQ ID NO: 37 | CP4 #7 | Polypeptide translation corresponding to SEQ ID NO. 36, homolog to *Chlamydia pneumoniae* Outer Membrane Lipoprotein (Cpn 0278 gene) |
| SEQ ID NO: 38 | CP4 #8 | (fragment) homolog to *Chlamydia pneumoniae* Oligopeptidase (pepF gene) |

TABLE 3-continued

SEQUENCE LISTING INDEX

| SEQ ID NO | CP4 NO | Description |
|---|---|---|
| SEQ ID NO: 39 | CP4 #8 | Polypeptide translation corresponding to SEQ ID NO. 38, homolog to *Chlamydia pneumoniae* Oligopeptidase (pepF gene) |
| SEQ ID NO: 40 | CP4 #8 | (full length) homolog to *Chlamydia pneumoniae* Oligopeptidase (pepF gene) |
| SEQ ID NO: 41 | CP4 #8 | Polypeptide translation corresponding to SEQ ID NO. 40, homolog to *Chlamydia pneumoniae* Oligopeptidase (pepF gene) |
| SEQ ID NO: 42 | CP4 #9 | (fragment) homolog to *Chlamydia pneumoniae* gene of unknown function, co-translationaly coupled to Yop N Flagellar-Type ATPase (Cpn 0708 gene) |
| SEQ ID NO: 43 | CP4 #9 | Polypeptide translation corresponding to SEQ ID NO. 42, homolog to *Chlamydia pneumoniae* gene of unknown function, co-translationally coupled to Yop N Flagellar-Type ATPase (Cpn 0708 gene) |
| SEQ ID NO: 44 | CP4 #9 | (full length) homolog to *Chlamydia pneumoniae* gene of unknown function, co-translationally coupled to Yop N Flagellar-Type ATPase (Cpn 0708 gene) |
| SEQ ID NO: 45 | CP4 #9 | Polypeptide translation corresponding to SEQ ID NO. 44, homolog to *Chlamydia pneumoniae* gene of unknown function, co-translationally coupled to Yop N Flagellar-Type ATPase (Cpn 0708 gene) |
| SEQ ID NO: 46 | CP4 #9 | (full length) homolog to *Chlamydia pneumoniae* Yop N Flagellar-Type ATPase (yscN gene) |
| SEQ ID NO: 47 | CP4 #9 | Polypeptide translation corresponding to SEQ ID NO. 46, homolog to *Chlamydia pneumoniae* Yop N Flagellar-Type ATPase (yscN gene) |
| SEQ ID NO: 48 | CP4 #10 | (fragment) homolog to *Chlamydia pneumoniae* outer membrane protein G (pmp 2 gene) (Nucleotides 1-423 were previously sequenced by Longbottom et al.) |
| SEQ ID NO: 49 | CP4 #10 | Polypeptide translation corresponding to SEQ ID NO. 48, homolog to *Chlamydia pneumoniae* outer membrane protein G (pmp 2 gene) |
| SEQ ID NO: 50 | CP4 #11 | (fragment) homolog to *Chlamydia pneumoniae* outer membrane protein G (pmp 2 gene) (Nucleotides 1-301 were previously sequenced by Longbottom et al.) |
| SEQ ID NO: 51 | CP4 #11 | Polypeptide translation corresponding to SEQ ID NO. 50, homolog to *Chlamydia pneumoniae* outer membrane protein G (pmp 2 gene) |
| SEQ ID NO: 52 | CP4 #10 & 11 | (full length) homolog to *Chlamydia pneumoniae* outer membrane protein G (pmp 2 gene). This gene immediately follows the OMP90A gene on *Chlamydia psittaci*, and nucleotides 1-502 were published by Longbottom et al., although they did not report this as a gene. |
| SEQ ID NO: 53 | CP4 #10 & 11 | Polypeptide translation corresponding to SEQ ID NO. 52, homolog to *Chlamydia pneumoniae* outer membrane protein G (pmp 2 gene) |
| SEQ ID NO: 54 | CP4 #12 | (fragment) *Chlamydia psittaci* 98 kDa outer membrane protein (POMP gene) (Previously sequenced by Longbottom, et al.) |
| SEQ ID NO: 55 | CP4 #12 | Polypeptide translation corresponding to SEQ ID NO. 54, *Chlamydia psittaci* 98 kDa outer membrane protein (POMP gene) |
| SEQ ID NO: 56 | CP4 #12 | (full length) *Chlamydia psittaci* 98 kDa outer membrane protein (POMP gene) (Previously sequenced by Longbottom *et al.*) |
| SEQ ID NO: 57 | CP4 #12 | Polypeptide translation corresponding to SEQ ID NO. 56, *Chlamydia psittaci* 98 kDa outer membrane protein (POMP gene) |
| SEQ ID NO: 58 | CP4 #14 | (fragment) homolog to *Chlamydia pneumoniae* Succinate Dehydrogenase (sdhC) |
| SEQ ID NO: 59 | CP4 #14 | Polypeptide translation corresponding to SEQ ID NO. 58, homolog to *Chlamydia pneumoniae* Succinate Dehydrogenase (sdhC) |
| SEQ ID NO: 60 | CP4 #14 | (full length) homolog to *Chlamydia pneumoniae* Succinate Dehydrogenase (sdhC) |
| SEQ ID NO: 61 | CP4 #14 | Polypeptide translation corresponding to SEQ ID NO. 60, homolog to *Chlamydia pneumoniae* Succinate Dehydrogenase (sdhC gene) |

Of the 14 single genes identified in this study, ten are internal fragments and three contain the C-terminus of the protein. Of the five most protective clones (CP4 #1-5), one was from a putative outer membrane protein (CP4 #4) and one was from a cell surface protein (CP4 #5). The other three were from cytosolic proteins, with CP4 #2 and CP4 #3 deriving independently from genes encoding a particular amidotransferase complex.

Four of the 14 clones have sequence similarity to a class of proteins known as putative outer membrane proteins (POMPs) in *Chlamydia psittaci* and *Chlamydia pneumoniae* (CP4 #4, CP4 #10, CP4 #11 and CP4 #12). Many of the "putative" outer membrane proteins are known to be localized to the outer membrane and to be highly immunogenic (Longbottom et al., 1996; Tan et al., 1990). The clone designated CP4 #4 is an in-frame fragment of POMP90A (Longbottom et al., 1998) and CP4 #12 is an inframe fragment of a 98 kDa POMP which has been completely sequenced (Accession U72499). The clones CP4 #10 and CP4 #11 immediately follow follow CP4 #4 in the geonome and have sequence similarity to POMPs in *Chlamydia psittaci, Chlamydia trachomatis*, and *Chlamydia pneumoniae*. As stated earlier, the clone CP4 #10 overlaps the CP4 #11 clone. Of these clones only CP4 #4 confers significant protection in isolation so clearly the criteria of being an outer membrane protein is not sufficient to predict a protective vaccine.

Example 7

Mixing Experiment

The two dimensional approach used to find protective gene fragments assumes that the protection is due to a single highly protective gene within a pool. to verify that such genes would be found, 25 ng (i.e. 1/2000) of either CP4 #4 or CP4 #11 was added to a pool that scored negative (pool 6 round 1). As depicted in FIG. 7, spiking with either clone converted the negative library to a positive. Of note is that CP4 #11 did not confer protection when tested individually, however, it does protect in combination.

The fact that a CP4 #4 positive library confers protection validates the sensitivity of the system. The fact that a CP4 #11 positive library protects implies that CP4 #11 can be a useful component of a vaccine, but that it may depend upon having other antigens present. A likely explanation is that CP4 #11 is a good vaccine antigen, but requires immunological help.

Example 8

Vaccination in Cattle

An important question is whether the genes identified in this manner in a mouse model are clinically relevant. Of course, this concern is not peculiar to genetic vaccines or ELI, but any system that uses models to identify vaccine candidates. In this case the clinically relevant situation is protection of cattle. In a preliminary experiment, the inventors evaluated the pool of 14 individual clones in the original host in a fertility challenge model. All fourteen clones were used as the the individual test data on each clone in mice was not available by the time it was necessary to initiate the cow trial.

TABLE 4

*Chlamydia psittaci* Vaccine in Cows

|  | Percent Pregnant | Pregnant | Not Pregnant |
|---|---|---|---|
| Not Challenged | 75 | 3 | 1 |
| Challenged, Not Vaccinated | 0 | 0 | 4 |
| EB Vaccine | 25 | 1 | 3 |
| Genetic Vaccine (14 gene pool) | 33 | 2 | 4 |

*Chlamydia psittaci* is normally introduced by the fecal-oral and respiratory routes in cattle, and disseminates to other tissues including reproductive organs. *Chlamydia psittaci* infection of the uterine mucosa reduces fertility, the basis of the economic interest in a *Chlamydia psittaci* vaccine. Four groups of heifers were used. One group was the naïve unchallenged control, another the naïve, challenged control, a third received the same pool of fourteen gene fragments that were tested in mice, and the fourth group was vaccinated with an experimental, inactivated vaccine of elementary bodies (EB) and also challenged. This EB vaccine had shown great promise in field trials but is too expensive to produce. After a prime and one boost, the heifers were estrus synchronized by prostaglandin injection, were in heat 2-3 days later, and were artificially inseminated, simultaneously receiving an intracervical chlamydial challenge of $3 \times 10^7$ inclusion forming units. The heifers were palpated for pregnancy at six weeks after insemination. This challenge was very high in order to maximize the difference between positive and negative control animals. This was necessary because only a small number of cows could be justified for this high-risk experiment.

Although the animal numbers are small, the results are quite encouraging. As is seen in Table 4, three out of four animals became pregnant in the positive control (non-challenged) group, 0/4 in the negative control (non-vaccinated, challenged) group, 2/6 in the genetic immunization group, and 1/4 in the elementary body vaccine group. The genetic immunization group, and 1/4 in the elementary body vaccine group. The genetic vaccine of the pooled genes performed at least as well as the EB vaccine. Also relative to the inventor's interest in therapeutic vaccines, these cows were not sterile with respect to *Chlamydia psittaci* at the time of the prime inoculation. The vaccination was in the face of previous exposure and low level *Chlamydia psittaci* infection, as determined by the high titers of preinoculation antichlamydial antibodies, and occasional positivity of *Chlamydia* omp1 PCRs from vaginal scrapings.

The next phase in developing a cow vaccine will be to experimentally verify the effectiveness of particular groups of the protective genes and then convert the codon usage of the *Chlamydia psittaci* genes to that of a mammal. This should increase the expression of the antigen I cows and increase the effectiveness of the vaccine. The inventors will test different combinations of those genes which have been found to be individually protective, as well as combinations with CP4 #11. Both original fragments and their full-length versions can be tested, both as nucleic acid segments and proteins. Once the combinations have been verified in mice or other small mammals, those combinations showing the most promise will be tested in cows. After immunization, the cows will be challenged with *Chlamydia psittaci*, either by direct challenge at insemination or infection by herd-mates. Direct challenge at insemination is a very severe and unnatural form of challenge. Therefore, even if protection is not demonstrated in the wake of such challenge, this does not necessarily mean that no protection has been conferred upon the cows.

Example 9

Fertility at 42 Days Post Breeding in Heifers Vaccinated with the Pool of the 5 Best Mouse-Protective Genes of *Chlamydia psittaci*

Because it is known that bacterial genes are not expressed efficiently in mammalian cells, the five most protective genes were chemically resynthesized to give an optimal mammalian codon bias. In addition, the full-length genes corresponding to the fragments isolated nt eh screen were used.

One group of five heifers was vaccinated with this pool. Another group of six heifers was vaccinated with an Alum-Quil A based vaccine containing per dose 100 μg each of the affinity-purified protein fragments expressed in *E. coli* from these genes. The control group of twelve heifers was vaccinated with a plasmid expressing an unrelated bacterial gene. Six weeks after the initial immunization all groups received booster vaccinations. Eight weeks later all heifers, including cohort of 27 non-vaccinated heifers, were estrus-synchronized by prostaglandin injection. After coming into heat two to three days later, the non-vaccinated cohort heifers were infected with an intrauterine chlamydial inoculum of $10^8$ IFUs *C. psittaci* B577. The function of this group was to shed chlamydiae, and thus to challenge through natural infection routes the vaccinated animals at the time of breeding. Eleven days later, the vaccinated animals were re-synchronized, and inseminated at estrus. The heifers were rectally palpated for pregnancy determination at six weeks after insemination.

The Genetic Vaccine group was vaccinated with DNA comprised of the pool of 5 full length, mammalian genes, the Protein Vaccine group with the 5 full-length proteins, and the control group with DNA of an unrelated gene from *Salmonella typhimurium*. During the 3-week period prior to *C. psittaci* infection, heifers of all groups, including the non-vaccinated challenge cohort, shed low levels of *C. psittaci* (0.5±0.2 genomes/swab) as determined by qPCR of weekly collected vaginal cytobrush swabs. To challenge the vaccinated animals via natural transmission transmission at the time of breeding, a cohort of 27 non-vaccinated animals was intracervically infected with *C. psittaci*. Eleven days later, all vaccinated groups were estrus-synchronized and inseminated. During the 4 weeks following the infection, the infected cohort animals shed high levels of chlamydiae (3826±2052 genomes per swab), and then returned to low baseline shedding (24.2±10.9 genomes per swab) for the remaining 5-week observation period. All vaccinated heifers were exposed to the natural challenge infection, as evident in their 7-fold increased post-breeding shedding of chlamydiae (3.6±1.2 genomes/swab; p<0.05) compared to pre-breeding shedding of all heifers. No difference in chlamydial shedding before or after breeding was found between the *C. psittaci* vaccinated and the control vaccinated groups.

TABLE 5

Fertility in cows vaccinated with a pool of the 5 best mouse protective *Chlamydia psittaci* genes.

| Group | Percent Pregnant | Pregnant | Not Pregnant |
| --- | --- | --- | --- |
| Control Group | 50 | 6 | 6 |
| Genetic Group | 80 | 4 | 1 |
| Protein Vaccine | 83 | 5 | 1 |

As is seen in Table 5, six out of twelve animals (50% fertility) became pregnant in the control group, 4/5 or (80% fertility in the genetic vaccine group, and five out of six (83% fertility) in the protein vaccine group. Thus, 9/11 animals in both vaccine groups were pregnant. The genetic vaccine of the pooled genes performed as well as the protein vaccine. These fertility data correspond very well with typical data of bovine herds with and without fertility problems. When both vaccine groups combined are compared to the controls, the 1-tailed Fisher's exact test indicates with a p=0.122 that vaccination is effective to improve *Chlamydia*-induced reduction of fertility. The odds ratio for improvement of fertility by vaccination is 4.5 (0.67-30.23, 95% confidence interval). These data are important in view of the fact that all heifers in the experiment had been previously exposed to chlamydiae and experienced low-level herd infection with *C. psittaci*, as determined by positive *C. psittaci* B577 MOMP-peptide ELISA and sporadic detection by quantitative PCR of low levels of *C. psittaci* in pre-challenge vaginal cytobrush swabs.

Example 10

Creation and Testing of Vaccines Using *Chlamydia psittaci* Nucleic Acid and Amino Acid Sequences to Protect Non-Bovine Species The *Chlamydia psittaci* sequences and antigens disclosed in this application are envisioned to be used in vaccines for *Chlamydia psittaci* in commercially important animals such as dairy cattle. Field trials in cattle are being conducted, as described above. However, these *Chlamydia psittaci* sequence may be used to create vaccines for other species as well, including other species of *Chlamydia* and other bacterial pathogens.

For example, one may use the information gained concerning *Chlamydia psittaci* to identify a sequence in another bacterial pathogen that had substantial homology to the *Chlamydia psittaci* sequences. In many cases, this homology would be expected to be more than 30% amino acid sequence identity or similarity and could be for only part of a protein, egg 30 amino acids, in the other species. The gene encoding such identity/similarity may be isolated and tested as a vaccine candidate in the appropriate model system either as a protein or nucleic acid. Alternatively, the *Chlamydia psittaci* homologs may be tested directly in an animal species of interest since having so few genes to screen (10 or less) and given that the genes had been demonstrated to be protective in another species the probability of success would be high. Alternatively, proteins or peptides corresponding to the homologs to the *Chlamydia psittaci* genes may be used to assay in animals or humans for immune responses in people or animals infected with the relevant pathogen. If such immune responses are detected, particularly if they correlated with protection, then the genes, proteins, or peptides corresponding to the homologs may be tested directly in animals or humans as vaccines.

Example 11

Creation and Testing of Commercial Vaccines Using *Chlamydia psittaci* Nucleic Acid and Amino Acid Sequences The genes identified and claimed as vaccine candidates can be developed into commercial vaccines in the following manner. The genes identified can be converted to optimized mammalian expression sequences by changing the codons. This is a straightforward procedure, which can be easily do by one of skill in the art, and has been done for the *Chlamydia psittaci* sequences. The genes can then be tested in the relevant host, for example, cattle, for the relevant protection, for example, fertility. Genetic immunization affords a simple method to test vaccine candidate for efficacy and this form of delivery has been used in a wide variety of animals including humans. Alternatively, the genes may be transferred to another vector, for example, a vaccinia vector, to be tested in the relevant host in this form. Alternatively, the corresponding protein, with or without adjuvants may be tested. These tests may be done on a relatively small number of animals. Once conducted, a decision can be made as to how many of the protective antigens to include in a larger test. Only a subset may be chosen based on the economics of production. A large field trial may be conducted using the formulation arrived at. Based on the results of the field trial, possibly done more than once at different locations, a commercial vaccine would go into production.

Example 12

Creation and Testing of Vaccines Against Other Pathogens Using *Chlamydia* Nucleic Acid and Amino Acid Sequences Since *Chlamydia pneumonia* has a similar pathobiology as *Chlamydia psittaci*, the inventors take advantage of the screening already accomplished on the *Chlamydia psittaci* genome to test *Chlamydia pneumoniae* for homologs corresponding to the ones from *Chlamydia psittaci* as vaccine candidates. Those of ordinary skill may expect that, as one moved evolutionary away from *Chlamydia Chlamydia psittaci*, the likelihood that the homologs would protect would presumably decline. However, researchers would be likely to test the homologs identified form even disparate species for protective ability in regard to relevant diseases, as this could reduce the search of a genome for vaccine candidates ~200-1,000 fold. Once the homologs have been identified and isolated, they maybe tested in the appropriate animal model system for efficacy as a vaccine. For example, the *Chlamydia* pneumonia homologs as genes or proteins can be tested in a mouse pneumonia model or in a mouse or rabbit atherosclerosis model.

In an example, showing the applicability of the use of homology to determine protective antigens in differing genera, it has been shown that hsp65, the *Mycobacterium tuberculosis* homolog of the *Chlamydia pneumonia* hsp60 gene, is protective against *Mycobacterium tuberculosis*, just as hsp60 is protective against *Chlamydia pneumonia*. This validates that homologous genes from two different pathogens can result in protective genetic vaccines against those pathogens. Therefore, there is a strong impetus to use the *Chlamydia* gene sequences that may be determined by the methods disclosed herein, to search for protective sequences of other species.

Figure 8:
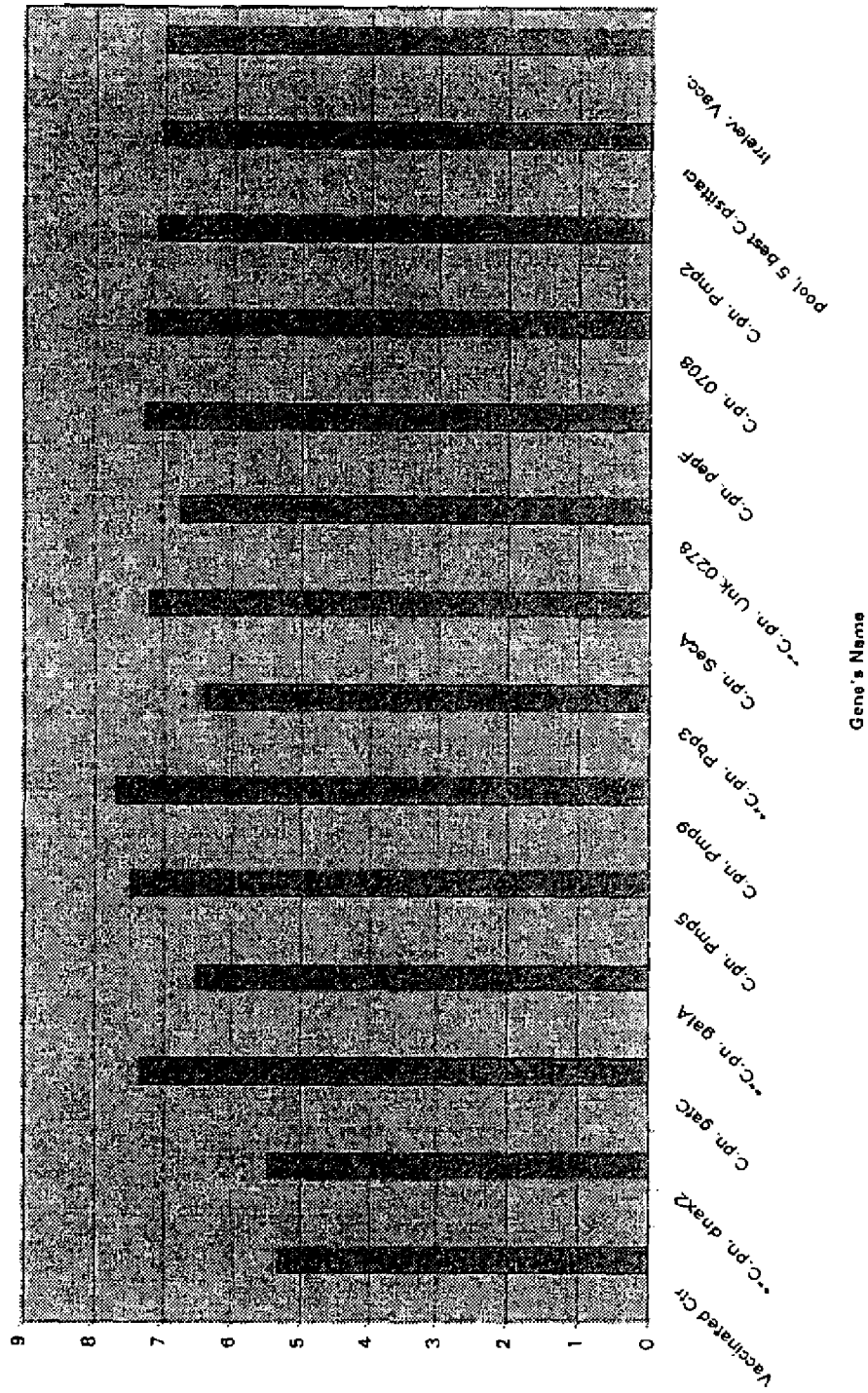
FIG. 8. Protection against *Chlamydia pneumoniae* challenge by various homologs of *Chlamydia pneumoniae* from ELI-selected *Chlamydia psittaci* (CP) gene.

To prove this concept, full length gene of *Chlamydia pneumonia* homolog of *Chlamydia psittaci* underwent PCR and the animals were challenged with *Chlamydia pneumonia*. As demonstrated in FIG. 8, and Table 6, the genes of *Chlamydia pneumonia* dnaX2 (SEQ. ID NO 62), gata (SEQ. ID NO 64); pbp3 (SEQ. ID NO 66); and the unknown gene 0278 (SEQ. ID NO 68) and their respective amino acid sequences (SEQ. ID NO 63, SEQ. ID NO 65, SEQ. ID NO 67, and SEQ. ID NO 69), conferred protection against *Chlamydia pneumonia*.

TABLE 6

Protection (log of colonies in lung) against *Chlamydia pneumoniae*

| Name of gene | Protection |
| --- | --- |
| Vaccinated Ctr | 5.3 |
| **C.pn dnax2 | 5.4 |
| C.pn gatC | 7.3 |
| **C.pn gatA | 6.5 |
| C.pn Pmp5 | 7.4 |
| C.pn Pmp9 | 7.6 |
| **C.pn Pbp3 | 6.4 |

TABLE 6-continued

Protection (log of colonies in lung) against *Chlamydia pneumoniae*

| Name of gene | Protection |
| --- | --- |
| C.pn SecA | 7.2 |
| **C.pn Unk.0278 | 6.7 |
| C.pn. pepF | 7.2 |
| C.pn. 0708 | 7.2 |
| C.pn. Pmp2 | 7.0 |
| pool, 5 best *C. psittaci* | 7.0 |
| Irrelev. Vacc. | 6.9 |

**genes conferred protection

The above study indicates that, once one of ordinary skill has access to the *Chlamydia* sequences disclosed in this specification, or to additional sequences determined to be protective using any of the methods disclosed in this specification, it is easy to run a computer-based search of relevant genetic databases in order to determine homologous sequences in other pathogens. For example, these searches can be run in the BLAST database in GenBank.

Once a sequence which is homologous to a protective sequence is determined, it is possible to obtain the homologous sequence using any of a number of methods known to those of skill. For example, it is easy to PCR amplify the pathogen homolog genes from genomic DNA and clone the genes into an appropriate genetic immunization vector, such as those used for ELI. These homolog genes can then be tested in an animal model appropriate for the pathogen for which protection is sought, to determine whether homologs of the *Chlamydia* genes will protect a host from challenge with that pathogen.

For example, the dnaX2 gene from *Chlamydia psittaci* is homologous to the dnaX2 gene from *Helicobacter pylori*. Therefore, one can will amplify the dnaX2 gene from *Helicobacter pylori* genomic DNA and clone it into a genetic immunization vector. The clone could then be tested for protection by inoculating animals with the *Helicobacter pylori* dnaX2 clone, then challenging the inoculated animals with *Helicobacter pylori* bacteria.

Of course, it is possible for one of ordinary skill to use the *Chlamydia* genes that are disclosed as protective herein, or determined to be protective using the methods disclosed as protective herein, or determined to be protective using the methods disclosed herein, to obtain protective sequences from a first non-Chlamydia organism to search for homologous sequences in a second non-Chlamydia or *Chlamydia* organism. So long as protective *Chlamydia* sequence is used as the starting point for determining at least one homology in such a chain of searches and testing, such methods are within the scope of this invention.

Example 13

Efficacy in Treating Ongoing Infection

The inventors have identified that the use of vaccinations comprising nucleic acid and/or polypeptide sequences of *Chlamydia* influence highly prevalent, ongoing infections of *Chlamydia* in cattle. Such infections are associated with bovine mastitis. Mastitis, or inflammation of the mammary gland, is the most prevalent production disease in dairy cows and is among the livestock diseases that causes the greatest economic loss in animal agriculture. In the United States alone, mastitis is estimated to cause an annual loss approaching $2 billion. Losses are mainly due to reduction in milk quantity, and to a lesser extent, a reduction in quality. Acute infections with *Chlamydia* have been associated with numerous distinct clinical disease entities in cattle, most predominantly, abortion and fertility disorders, sporadic encephalomyelitis, kerato-conjunctivitis, pneumonia, enteritis, mastitis and polyarthritis. However, the vast majority of *Chlamydia* infections in cattle, particularly on-going, low level infections, are not associated with obvious clinical disease. This ubiquitous on-going infection of cattle has an unknown health impact cattle has an unknown health impact in the overall cattle population.

*Chlamydia psittaci* infection is known to produce acute mastitis of bovine mammary glands, accompanied by fever and anorexia. However, the disease appears to be self-limiting, leading to a state of reduced milk production and mammary gland atrophy. Frequent detection of *Chlamydia* in the milk of mammary glands without acute disease leads to the suspicion that such chronic infections are frequent and influence milk production. Therefore, modification of an on-going immune response in such cows, to improve the health of the *Chlamydia*-infected mammary gland, would be highly desirable. Moreover, studies of the effect of *Chlamydia* vaccines are important not only for cattle, but also for human chronic inflammatory diseases such as pelvic inflammatory disease and reactive arthritis, or coronary heart disease, disease for which strong associations with *Chlamydia* strain infections have been found. The ability to treat an ongoing infection with a *Chlamydia* vaccine is, therefore, of distinct importance.

Materials and Methods

A herd of 147 Holstein cows were studied. The cows had a mean age of 4.8 years and 2.4 lactations. The somatic cell count in milk (SCC) was used as a parameter for monitoring udder health. Milk from a healthy mammary bovine gland contains less than 100,000 somatic cells per milliliter, and there is consensus that more than $10^5$ SCC per milliliter bovine milk indicate inflammation of the mammary gland. Milk with 200,000 or more cells per milliliter is of reduced value because manufacturing properties are compromised. Accordingly, milk somatic cell counts of individual dairy cows are routinely monitored as one of several determinants of raw milk quality cost. Initially, the herd of 147 Holsteins were measured for somatic cell count and 42% of the cows after first delivery had milk SCC higher than one times $10^5$ per milliliter and 31% of all cows had milk SCC above four times $10^5$ per milliliter. *Staphylococcus aureus* mastitis, a common cause of bovine mastitis herd problems was not observed in the herd.

A total of 140 cows were enrolled in the study, with 70 cows, each randomly assigned to a *Chlamydia* vaccine group or a mock control vaccine group. The cows were immunized on days 0 and 35 of the study by subcutaneous administration of a 2 milliliter vaccine dose. In addition, all animals received an intramuscular dose of an infectious bovine rhinotracheitis-bovine respiratory syncytial virus-parainfluenza 3 virus combination live attenuated vaccine on days 104 and 133, and on days 104 inactivated bovine virus diarrhea virus vaccine followed by live attenuated bovine virus diarrhea virus vaccine on day 140. Combined quarter milk samples for SCC determination were obtained from all cows during determination of milk yield on days 0, 12, 44 and subsequently in monthly intervals. Day 0 corresponds to the day of first vaccination. Additional quarter milk samples for *Chlamydia* PCR assays were collected from random sub-sets of *Chlamydia* and mock vaccinated cows on days 0, 1, 4, 7, 10, 94, and 109. All statistical analyses were performed with the Statistica 7.0 software package, available from StatSoft, Inc. (Tulsa, Okla.).

Results

At the initiation of the study, the *Chlamydia* infection status of all cows was determined by PCR of vaginal and conjunctival swab specimens obtained on day 0, and by anti-Chlamydia serum IgG1 antibody enzyme amino assay. All cows had anti-Chlamydia serum antibodies, and 49% of all cows were positive in at least one of the day 0 *Chlamydia* PCRs. Further analysis revealed that all positive PCRs for milk specimens amplified *Chlamydia psittaci* DNA fragments. The cows were stratified into positive and negative animals on day 0, and animals with high and low anti-Chlamydia antibody levels. Milk somatic cell counts of these groups were analyzed by factorial repeated measures of analysis variance (ANOVA), and cows with bacterial culture positive, i.e., non-Chlamydia, clinical mastitis were excluded from the analysis. Cows infected with *Chlamydia* on day 0 had consistently and significantly higher ($p=0.027$) SCCs than non-infected cows on days 0 or 12. Cows with low anti-Chlamydia antibody levels had significantly higher SCCs than cows with high antibody levels ($p \leqq 0.036$).

To examine the influence of *Chlamydia* infection on the inflammatory status of the bovine mammary gland, the anti-Chlamydia immune response of the herd was modified by vaccination with the *Chlamydia* vaccine or with a control vaccine without Chlamydial antigen. Experimental cows were vaccinated on days 0 and 35 with either a *Chlamydia* vaccine or a mock vaccine, and the differences between the animals with perturbed and unmodified anti-Chlamydial immunity were monitored. This is demonstrated in FIG. 9*a*, where *Chlamydia* vaccination elicited a strong, specific immune response resulting in significantly increased *Chlamydia* antibody levels as compared to mock vaccinated cows. The effect of *Chlamydia* vaccination on milk somatic cell count is also shown in FIG. 9*b*. *Chlamydia* vaccinated cows had a significantly decreased somatic cell count with an average of 123,000 cells per milliliter of milk at all timed points after vaccination. In comparison, mock vaccinated cows had an average of 230,000 cells per milliliter of milk. Peak reduction was observed on day 76 from 230,000 in mock vaccinated cows to 83,000 cells per milliliter in *Chlamydia* vaccinated cows.

Accordingly, the experiment described above demonstrates that nearly every cow is continuously exposed to the *Chlamydia* bacteria. Cows likely cycle through periods of relative resistance after an infection episode, indicated by increased anti-Chlamydia antibody levels. This was followed by relative susceptibility to *Chlamydia* bacteria associated with lower antibody levels. More importantly, vaccine mediated immune stimulation resulted in dramatically decreased milk somatic cells in *Chlamydia* vaccinated cows when compared to mock vaccinated animals. Furthermore, it is probable that the somatic cell count reduction will correlate with higher milk production, consistent with information known in the art. While the modified anti-Chlamydia immune response elicited by therapeutic vaccination of infected animals does not completely eliminate the presence of *Chlamydia* bacteria, it may well be that *Chlamydia* vaccine-induced immune response reduces Chlamydial loads, but does not completely eliminate the organisms. organisms. Thus, such a vaccine would be useful to influence ongoing infection. The disease protective effect of the *Chlamydia* vaccine makes therapeutic vaccination for reduction of bovine somatic milk cells an attractive choice for livestock industries as compared to the use of antibiotics or other drugs for this purpose.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods in the steps or in the sequence of steps of the method described herein without departing from the concept, spirit and scope of the invention. More specifically, it will be apparent that certain agents described herein while the same or similar results would be achieved. All such similar substitutes and modifications apparent to those skilled in the art are deemed to be within the spirit, scope and concept of the invention as defined by the appended claims.

What is claimed is:

1. A method of immunizing an animal comprising administering to the animal a *Chlamydia psittaci* antigen having the sequence of SEQ ID NO:21 in an amount effective to induce an immune response against *Chlamydia psittaci*.

2. The method of claim 1 wherein the method further comprises preparing a pharmaceutical composition of the *Chlamydia psittaci* antigen.

3. The method of claim 1 wherein the method further comprises administering to the animal a second *Chlamydia psittaci* antigen.

4. The method of claim 3, where in the second *Chlamydia psittaci* antigen is on at least nine amino acid fragment of SEQ ID NO:23.

5. The method of claim 1 wherein the animal is a bovine.

6. The method of claim 1 wherein the animal is a human.

7. The method of claim 3 wherein the animal is a bovine.

8. The method of claim 3 wherein the animal is a human.

9. The method of claim 1, wherein the *Chlamydia psittaci* antigen comprises an amino acid sequence as set forth as SEQ ID NO:23.

10. The method of claim 3, wherein the second *Chlamydia psittaci* antigen comprises an amino acid sequence as set forth as SEQ ID NO: 7, 9, 11, 13, or 17.

11. The method of claim 1 wherein the animal is a mammal.

12. The method of claim 3 wherein the animal is a mammal.

13. The method of claim 3 wherein the step of administering the second *Chlamydia psittaci* antigen comprises administering the second antigen simultaneously with the administration of the first antigen.

14. The method of claim 3 wherein the step of administering the second *Chlamydia psittaci* antigen comprises administering the second antigen subsequent to the administration of the first antigen.

15. The method of claim 3 wherein the step of administering the second *Chlamydia psittaci* antigen comprises administering the second antigen prior to administration of the first antigen.

* * * * *

SEQUENCE LISTING

```
<160> NUMBER OF SEQ ID NOS: 69

<210> SEQ ID NO 1
<211> LENGTH: 127
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 1
ctgcacctgg tccttcgcct gagaggtgca gatcttggat cctaagtaag taagcttgca      60
tgcctgcagg tcgactctag gtgactaata tctagaggat cgatcccggg tggcatccct     120
gtgaccc                                                                127

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 2
gatctggatc ccgat                                                        15

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 3
atcgggctcc a                                                            11

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
    Primer

<400> SEQUENCE: 4
ccgcaccctc tctgattac                                                    19

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
    Primer
```

-continued

<400> SEQUENCE: 5
ctggagtggc aacttcc                                                          17

<210> SEQ ID NO 6
<211> LENGTH: 449
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
gaatgtattc gcacgcaaaa atacgctgaa gctttgcttc ctgtcacgac agcgatcaat       60
tctggagtcg cgcctatcac cttcctccat gacctcactg ttttttatcg cgatgtactg      120
ctaaacaaag atcagggaaa ttctcctcta tcggccatcg ccatgcacta ttccagtgaa      180
tgtttattag aaatcattga tttccttggt gaagcggcca acatctaca acaaactatt       240 tttgaaaaaa cattttaga aacagtcatc atccatctta ttcggatatg ccaacgtccc       300
tctttagaaa ctctgttttc tcaactgaaa acatccacgt ttgatacagt gagaaacgta      360
ccccagcagc aagaaccctc gaaaccgagt atacaacctg aaaaacacta tcaagatcag      420
agtttcttaa cttcaccttc tcccacgcc                                         449

<210> SEQ ID NO 7
<211> LENGTH: 149
<212> TYPE: PRT
<213> ORGANISM: Chlamydia psittaci

<400> SEQUENCE: 7

Glu Cys Ile Arg Thr Gln Lys Tyr Ala Glu Ala Leu Leu Pro Val Thr
1               5                   10                  15

Thr Ala Ile Asn Ser Gly Val Ala Pro Ile Thr Phe Leu His Asp Leu
20 25 30

Thr Val Phe Tyr Arg Asp Val Leu Leu Asn Lys Asp Gln Gly Asn Ser
35 40 45

Pro Leu Ser Ala Ile Ala Met His Tyr Ser Ser Glu Cys Leu Leu Glu
50 55 60

Ile Ile Asp Phe Leu Gly Glu Ala Ala Lys His Leu Gln Gln Thr Ile
65 70 75 80

Phe Glu Lys Thr Phe Leu Glu Thr Val Ile Ile His Leu Ile Arg Ile
85 90 95

Cys Gln Arg Pro Ser Leu Glu Thr Leu Phe Ser Gln Leu Lys Thr Ser
100 105 110

Thr Phe Asp Thr Val Arg Asn Val Pro Gln Gln Gln Glu Pro Ser Lys
115 120 125

Pro Ser Ile Gln Pro Glu Lys His Tyr Gln Asp Gln Ser Phe Leu Thr
130 135 140

Ser Pro Ser Pro Thr
145

<210> SEQ ID NO 8
<211> LENGTH: 1332
<212> TYPE: DNA
<213> ORGANISM: Chlamydia psittaci

<400> SEQUENCE: 8
atgacatcag caacatacca agtttcttct agaaaatacc gccctcaaac atttgccgaa 60

-continued

```
atgctggggc aagatgccgt ggtcactgtt ttaaaaaatg ctttgcagtt tcaacgtgtc    120
gcgcatgcgt atttattttc agggattcgc ggaacaggaa aaacaacttt agcaagaatc    180
tttgcaaaag ccttaaactg taaagagctg actcctgaac atgaaccatg caaccagtgt    240
tgtgtttgta aagaaatctc ttcaggaacc tccttagacg tgatcgaaat cgatggtgcc    300
tcgcaccgag gtattgaaga tatccgtcaa atcaatgaaa ccgtgctctt tactcctgcc    360
aaatcacaat ataaaatcta tatcatagat gaagtccata tgctgactaa ggaggcgttt    420
aattccttac tcaaaacttt agaagagcct ccgagccatg taaaattctt cttagcgact    480
acagaaaatt ataaaatacc cagcaccatt ttaagtcgtt gtcaaaaaat gcacctaaag    540
agaattcctg agacaatgat tgtagataag ctagcatcca tatctcaagc aggtgggata    600
gaaacctctc gagaagctct tcttcctatt gctagagcag cacagggaag cttacgcgat    660
gctgaatctc tttatgatta tgtcataggg ttattcccta catctttatc cccagagttg    720
gttgcagacg cattaggttt attatctcaa gacaccttag ctacattatc agaatgtatt    780
cgcacgcaaa aatacgctga agctttgctt cctgtcacga cagcgatcaa ttctggagtc    840
gcgcctatca ccttcctcca tgacctcact gtttttatc gcgatgtact gctaaacaaa     900
gatcagggaa attctcctct atcggccatc gccatgcact attccagtga atgtttatta    960
gaaatcattg atttccttgg tgaagcggcc aaacatctac aacaaactat tttgaaaaa    1020 acatttttag aaacagtcat catccatctt attcggatat gccaacgtcc ctctttagaa   1080
actctgtttt ctcaactgaa aacatccacg tttgatacag tgagaaacgt accccagcag   1140
caagaaccct cgaaaccgag tatacaacct gaaaaacact atcaagatca gagtttctta   1200
acttcacctt ctcccacgcc aaaagttcag catcaaaaag aagcttcccc ttctttagtg   1260
ggatcagcta ctatagatac gcttttacaa tttgctgttg ttgagttttc cggaatttta   1320
accaaggagt aa                                                        1332
```

```
<210> SEQ ID NO 9
<211> LENGTH: 443
<212> TYPE: PRT
<213> ORGANISM: Chlamydia psittaci

<400> SEQUENCE: 9

Met Thr Ser Ala Thr Tyr Gln Val Ser Ser Arg Lys Tyr Arg Pro Gln
1               5                   10                  15

Thr Phe Ala Glu Met Leu Gly Gln Asp Ala Val Val Thr Val Leu Lys
            20                  25                  30

Asn Ala Leu Gln Phe Gln Arg Val Ala His Ala Tyr Leu Phe Ser Gly
        35                  40                  45

Ile Arg Gly Thr Gly Lys Thr Thr Leu Ala Arg Ile Phe Ala Lys Ala
    50                  55                  60

Leu Asn Cys Lys Glu Leu Thr Pro Glu His Glu Pro Cys Asn Gln Cys
65                  70                  75                  80

Cys Val Cys Lys Glu Ile Ser Ser Gly Thr Ser Leu Asp Val Ile Glu
                85                  90                  95

Ile Asp Gly Ala Ser His Arg Gly Ile Glu Asp Ile Arg Gln Ile Asn
            100                 105                 110

Glu Thr Val Leu Phe Thr Pro Ala Lys Ser Gln Tyr Lys Ile Tyr Ile
        115                 120                 125

Ile Asp Glu Val His Met Leu Thr Lys Glu Ala Phe Asn Ser Leu Leu
    130                 135                 140

Lys Thr Leu Glu Glu Pro Pro Ser His Val Lys Phe Phe Leu Ala Thr
```

|   |   |   |   |   | 145 |   |   |   |   | 150 |   |   |   |   | 155 |   |   |   |   | 160 |
|---|---|---|---|---|-----|---|---|---|---|-----|---|---|---|---|-----|---|---|---|---|-----|

Thr Glu Asn Tyr Lys Ile Pro Ser Thr Ile Leu Ser Arg Cys Gln Lys
               165                170               175

Met His Leu Lys Arg Ile Pro Glu Thr Met Ile Val Asp Lys Leu Ala
         180                  185               190

Ser Ile Ser Gln Ala Gly Gly Ile Glu Thr Ser Arg Glu Ala Leu Leu
      195               200               205

Pro Ile Ala Arg Ala Ala Gln Gly Ser Leu Arg Asp Ala Glu Ser Leu
210                 215               220

Tyr Asp Tyr Val Ile Gly Leu Phe Pro Thr Ser Leu Ser Pro Glu Leu
225               230               235              240

Val Ala Asp Ala Leu Gly Leu Leu Ser Gln Asp Thr Leu Ala Thr Leu
            245               250              255

Ser Glu Cys Ile Arg Thr Gln Lys Tyr Ala Glu Ala Leu Leu Pro Val
        260               265              270

Thr Thr Ala Ile Asn Ser Gly Val Ala Pro Ile Thr Phe Leu His Asp
      275               280               285

Leu Thr Val Phe Tyr Arg Asp Val Leu Leu Asn Lys Asp Gln Gly Asn
   290                295              300

Ser Pro Leu Ser Ala Ile Ala Met His Tyr Ser Ser Glu Cys Leu Leu
305                 310               315              320

Glu Ile Ile Asp Phe Leu Gly Glu Ala Ala Lys His Leu Gln Gln Thr
        325               330              335

Ile Phe Glu Lys Thr Phe Leu Gly Thr Val Ile Ile His Leu Ile Arg
         340                345              350

Ile Cys Gln Arg Pro Ser Leu Glu Thr Leu Phe Ser Gln Leu Lys Thr
      355               360              365

Ser Thr Phe Asp Thr Val Arg Asn Val Pro Gln Gln Gln Glu Pro Ser
370                 375               380

Lys Pro Ser Ile Gln Pro Glu Lys His Tyr Gln Asp Gln Ser Phe Leu
385                 390               395              400

Thr Ser Pro Ser Pro Thr Pro Lys Val Gln His Gln Lys Glu Ala Ser
            405               410              415

Pro Ser Leu Val Gly Ser Ala Thr Ile Asp Thr Leu Leu Gln Phe Ala
         420                425              430

Val Val Glu Phe Ser Gly Ile Leu Thr Lys Glu
      435               440

<210> SEQ ID NO 10
<211> LENGTH: 123
<212> TYPE: DNA
<213> ORGANISM: Chlamydia psittaci

<400> SEQUENCE: 10
gagtttattc aagagtatga aagttcttta aatgaagtca ttaaaactat ggcagcatcc   60
atcgctatgg atgtaaccga cgtggttatt gaggttggtt tatcccatgt gatcagtccc  120
gaa  123

<210> SEQ ID NO 11
<211> LENGTH: 41
<212> TYPE: PRT
<213> ORGANISM: Chlamydia psittaci

<400> SEQUENCE: 11

Glu Phe Ile Gln Glu Tyr Glu Ser Ser Leu Asn Glu Val Ile Lys Thr
1               5                10               15

Met Ala Ala Ser Ile Ala Met Asp Val Thr Asp Val Val Ile Glu Val
            20                  25                  30

Gly Leu Ser His Val Ile Ser Pro Glu
        35                  40

<210> SEQ ID NO 12
<211> LENGTH: 303
<212> TYPE: DNA
<213> ORGANISM: Chlamydia psittaci

<400> SEQUENCE: 12
atgacacaac cctatgtaac tagagaagac attatacttc tggcgaagag ttcagctctg    60
gaattaagcg aagagtttat tcaagagtat gaaagttctt taaatgaagt cattaaaact   120
atggcagcat ccatcgctat ggatgtaacc gacgtggtta ttgaggttgg tttatcccat   180
gtgatcagtc ccgaagattt acgagaagat atcgttgcct caagtttctc tcgtgaggag   240
tttctaacta atgtccctga atccttaggg ggattagtaa agtacccac agtcattaag    300 tag                                                                  303

<210> SEQ ID NO 13
<211> LENGTH: 100
<212> TYPE: PRT
<213> ORGANISM: Chlamydia psittaci

<400> SEQUENCE: 13

Met Thr Gln Pro Tyr Val Thr Arg Glu Asp Ile Ile Leu Leu Ala Lys
1               5                   10                  15

Ser Ser Ala Leu Glu Leu Ser Glu Glu Phe Ile Gln Glu Tyr Glu Ser
            20                  25                  30

Ser Leu Asn Glu Val Ile Lys Thr Met Ala Ala Ser Ile Ala Met Asp
        35                  40                  45

Val Thr Asp Val Val Ile Glu Val Gly Leu Ser His Val Ile Ser Pro
    50                  55                  60

Glu Asp Leu Arg Glu Asp Ile Val Ala Ser Ser Phe Ser Arg Glu Glu
65                  70                  75                  80

Phe Leu Thr Asn Val Pro Glu Ser Leu Gly Gly Leu Val Lys Val Pro
                85                  90                  95

Thr Val Ile Lys
            100

<210> SEQ ID NO 14
<211> LENGTH: 514
<212> TYPE: DNA
<213> ORGANISM: Chlamydia psittaci

<400> SEQUENCE: 14
gaaaagtgtg atgtgattgc gatgcctgta tgctcatgcc cagcattcgc cgatggcgaa    60
atccttgatc ctacctctct atatctccag gatatctata ccgtggctat gaatttagcc   120
tacctcccag ctatcgccgt tccttcaggg ttttctcgag aagggctgcc tctaggattc   180
caggtgattg acaaaagggt aaagatcaa caggtgtgcc aggtaggcta tagcttccaa    240
gaacattcag gaattaagaa tttatacccct aaaggatgta acaaacttgt tgatggagag   300
gtgaaataat gagcgacgtt tatgctgatt gggaatccgt cataggtctt gaagtccacg   360
tagaattaaa cacaaaatct aaattgttca gttgtgcacg caaccgtttt ggagacgaac   420
ctaatacaaa catctctcct gtatgcaccg gcatgccggg gtcactgcca gtactgaata   480

-continued aagaagcagt gagaaaggct gttttatttg gttg 514

<210> SEQ ID NO 15
<211> LENGTH: 102
<212> TYPE: PRT
<213> ORGANISM: Chlamydia psittaci

<400> SEQUENCE: 15

```
Glu Lys Cys Asp Val Ile Ala Met Pro Val Cys Ser Cys Pro Ala Phe
1               5                   10                  15

Ala Asp Gly Glu Ile Leu Asp Pro Thr Ser Leu Tyr Leu Gln Asp Ile
            20                  25                  30

Tyr Thr Val Ala Met Asn Leu Ala Tyr Leu Pro Ala Ile Ala Val Pro
        35                  40                  45

Ser Gly Phe Ser Arg Glu Gly Leu Pro Leu Gly Phe Gln Val Ile Gly
    50                  55                  60

Gln Lys Gly Lys Asp Gln Gln Val Cys Gln Val Gly Tyr Ser Phe Gln
65                  70                  75                  80

Glu His Ser Gly Ile Lys Asn Leu Tyr Pro Lys Gly Cys Asn Lys Leu
                85                  90                  95

Val Asp Gly Glu Val Lys
            100
```

<210> SEQ ID NO 16
<211> LENGTH: 1476
<212> TYPE: DNA
<213> ORGANISM: Chlamydia psittaci

<400> SEQUENCE: 16

```
atgtatcaga agagtgcctt agagttaaga aatgccgtag tgagtggaga gtcttcagct     60
acagcaatag caaagtattt ttataataga ataaaaacag aagacaatca gataggagct    120
tttctttctc tttgtgaaga aagagcttat gagaaagcag ctatcataga tgcgaaagtg    180
gcgcgaggag aacctttggg gaaactcgca ggtgtcccca tcgggataaa agataatatt    240
catattcggg gtttgcgcac cacttgtgct tctaaaatgt tagaaaatta tatagcgcct    300
tttgatgcta cagtcgtcga acggatagaa gctgaagatg ggtcattttt aggcaaactc    360
aatatggatg agtttgctat gggatcgaca acgcagtatt ctgctttcca tcctacgaaa    420
aatccttggg gtttatcctg tgtgccagga ggatcttcag gggatccgc cgccgcagtt    480
tctgcaagat tttgtcctat agcgttaggt tcggataccg gtggatctat acgtcagcca    540
gcagcatttt gtggagttgt ggggtttaag ccctcctatg gagccgtctc ccgttacggt    600
ttagtcgctt ttgggtcttc attagatcag ataggccctt taacaacagt tgtcgaagat    660
gtcgccttag ctatggatgt attcgcaggt aaggatgata gagatgcaac ttctcagaag    720
ttttttacag gatctttcca agaggccttg tctttagacg ttccgagttt gatcggcgtg    780
cctatgggat ttttagacgg tttacgtgat gatgttaaag agaatttctt tgcctcttta    840
agtattttgg aacgtcaggg tagccgcatt gttgaagtgg atcttaacat cttagatcac    900
gctgtctctg tttactacat tgtcgcttct gcagaagccg caacaaatct tgcaagattt    960
gatggtattc gttacggcta tcgttctcca gaagcgcata gtatagaaga tatttatacg   1020
atctcccgcg tacaaggctt cggtaaggaa gtcatgcgta ggattctttt aggtaactat   1080
gtgttatcca ctgagcgcca aaatgtctat tataagaaag gctccgcaat tcgagcaaaa   1140
atcattcaag cttttcaaaa agcttatgaa aagtgtgatg tgattgcgat gcctgtatgc   1200
tcatgcccag cattcgccga tggcgaaatc cttgatccta cctctctata tctccaggat   1260
```

```
atctataccg tggctatgaa tttagcctac ctcccagcta tcgccgttcc ttcagggttt    1320
tctcgagaag ggctgcctct aggattccag gtgattggac aaaagggtaa agatcaacag    1380
gtgtgccagg taggctatag cttccaagaa cattcaggaa ttaagaattt atatccctaaa   1440 ggatgtaaca aacttgttga tggagaggtg aaataa                              1476
```

<210> SEQ ID NO 17
<211> LENGTH: 491
<212> TYPE: PRT
<213> ORGANISM: Chlamydia psittaci

<400> SEQUENCE: 17

```
Met Tyr Gln Lys Ser Ala Leu Glu Leu Arg Asn Ala Val Val Ser Gly
1               5                   10                  15

Glu Ser Ser Ala Thr Ala Ile Ala Lys Tyr Phe Tyr Asn Arg Ile Lys
            20                  25                  30

Thr Glu Asp Asn Gln Ile Gly Ala Phe Leu Ser Leu Cys Glu Glu Arg
        35                  40                  45

Ala Tyr Glu Lys Ala Ala Ile Ile Asp Ala Lys Val Ala Arg Gly Glu
    50                  55                  60

Pro Leu Gly Lys Leu Ala Gly Val Pro Ile Gly Ile Lys Asp Asn Ile
65                  70                  75                  80

His Ile Arg Gly Leu Arg Thr Thr Cys Ala Ser Lys Met Leu Glu Asn
                85                  90                  95

Tyr Ile Ala Pro Phe Asp Ala Thr Val Val Glu Arg Ile Glu Ala Glu
            100                 105                 110

Asp Gly Val Ile Leu Gly Lys Leu Asn Met Asp Glu Phe Ala Met Gly
        115                 120                 125

Ser Thr Thr Gln Tyr Ser Ala Phe His Pro Thr Lys Asn Pro Trp Gly
    130                 135                 140

Leu Ser Cys Val Pro Gly Gly Ser Gly Ser Ala Ala Ala Val
145                 150                 155                 160

Ser Ala Arg Phe Cys Pro Ile Ala Leu Gly Ser Asp Thr Gly Gly Ser
                165                 170                 175

Ile Arg Gln Pro Ala Ala Phe Cys Gly Val Val Gly Phe Lys Pro Ser
            180                 185                 190

Tyr Gly Ala Val Ser Arg Tyr Gly Leu Val Ala Phe Gly Ser Ser Leu
        195                 200                 205

Asp Gln Ile Gly Pro Leu Thr Thr Val Val Glu Asp Val Ala Leu Ala
    210                 215                 220

Met Asp Val Phe Ala Gly Lys Asp Asp Arg Asp Ala Thr Ser Gln Lys
225                 230                 235                 240

Phe Phe Thr Gly Ser Phe Gln Glu Ala Leu Ser Leu Asp Val Pro Ser
                245                 250                 255

Leu Ile Gly Val Pro Met Gly Phe Leu Asp Gly Leu Arg Asp Asp Val
            260                 265                 270

Lys Glu Asn Phe Phe Ala Ser Leu Ser Ile Leu Glu Arg Gln Gly Ser
        275                 280                 285

Arg Ile Val Glu Val Asp Leu Asn Ile Leu Asp His Ala Val Ser Val
    290                 295                 300

Tyr Tyr Ile Val Ala Ser Ala Glu Ala Ala Thr Asn Leu Ala Arg Phe
305                 310                 315                 320

Asp Gly Ile Arg Tyr Gly Tyr Arg Ser Pro Glu Ala His Ser Ile Glu
                325                 330                 335
```

```
Asp Ile Tyr Thr Ile Ser Arg Val Gln Gly Phe Gly Lys Glu Val Met
                340                 345                 350

Arg Arg Ile Leu Leu Gly Asn Tyr Val Leu Ser Thr Glu Arg Gln Asn
        355                 360                 365

Val Tyr Tyr Lys Lys Gly Ser Ala Ile Arg Ala Lys Ile Ile Gln Ala
    370                 375                 380

Phe Gln Lys Ala Tyr Glu Lys Cys Asp Val Ile Ala Met Pro Val Cys
385                 390                 395                 400

Ser Cys Pro Ala Phe Ala Asp Gly Glu Ile Leu Asp Pro Thr Ser Leu
                405                 410                 415

Tyr Leu Gln Asp Ile Tyr Thr Val Ala Met Asn Leu Ala Tyr Leu Pro
            420                 425                 430

Ala Ile Ala Val Pro Ser Gly Phe Ser Arg Glu Gly Leu Pro Leu Gly
        435                 440                 445

Phe Gln Val Ile Gly Gln Lys Gly Lys Asp Gln Gln Val Cys Gln Val
    450                 455                 460

Gly Tyr Ser Phe Gln Glu His Ser Gly Ile Lys Asn Leu Tyr Pro Lys
465                 470                 475                 480

Gly Cys Asn Lys Leu Val Asp Gly Glu Val Lys
                485                 490

<210> SEQ ID NO 18
<211> LENGTH: 1464
<212> TYPE: DNA
<213> ORGANISM: Chlamydia psittaci

<400> SEQUENCE: 18
atgagcgacg tttatgctga ttgggaatcc gtcataggtc ttgaagtcca cgtagaatta      60
aacacaaaat ctaaattgtt cagttgtgca cgcaaccgtt tggagacga acctaataca     120 aacatctctc ctgtatgcac cggcatgccg gggtcactgc cagtactgaa taaagaagca     180
gtgagaaagg ctgttttatt tggttgtgct gttgaaggcg aagtagcttt gctcagccgt     240
tttgatagaa gtcctatttt tatcccgat agcccaagga attttcaaat taccaattc      300 gaacatccta ttgtgcgagg aggacatata aaagctatcg ttcacggtga ggaacgtcat     360
tttgaactgg ctcaagcgca tatcgaagat gatgccggta tgctaaaaca tttcggagaa     420
tttgctggag tagattataa ccgcgctggt gtacctttaa tagagattgt gtctaagccg     480
tgcatgtttt gtgctgatga tgctgttgct tatgccacag ctttggtatc cttattagac     540
tacataggca tttctgactg taatatggaa gaaggctcgg tacgctttga tgtaaacata     600
tccgtacgtc ctaaaggtag cgaagaacta cgcaataaag tagaaattaa aaatatgaac     660
tcctttgctt ttatggccca agctctagaa gccgagcgtt gtcgtcagat cgatgcatat     720
ttagacaatc caaatgcaga ccccaaaact gttattccag gagcgacata ccgttgggat     780
cctgaaaaga aaaaaacagt gttgatgcgt cttaaggaac gagctgaaga ttacaagtat     840
ttcatagagc ctgatctccc agtattgcaa ttaacagaag catatattga tgaaattcgt     900
catacgcttc ccgagctccc tttcaacaaa taccaaggt attttgcacga atatgctctt     960 gccgaagaca tcgctgccat tttaattagc gataagcata gtgcgcactt ctttgaatta    1020
gccgctcagg aatgtaaaaa ctacagagcc ctttctaatt ggttaactgt tgagtttgcc    1080
ggacgttgta aactcaaggg taagaatctc gctttctcag gtatcctgcc cagtagtgta    1140
gctcagcttg tgaattttat tgatcaaggc gtgattaccg aaagatcgc taaggatatc    1200 gcagacatga tgatggaatc tcctgaaaag agtcctgaga ctatcctcaa agaaaatcct    1260
```

```
gaaatgttgc ccatgacaga tgaaagtgcg ttggtggcga tcatttccga ggtgattacc   1320
gcaaatccgc agtctgtcgt agactacaaa agtggtaaga ccaaggcgtt aggattttta   1380
gttgggcaaa ttatgaaacg tacccagggc aaggcccctc caaatagggt aaatgaactt   1440
ttgcttgtgg aattaagtaa ataa                                          1464

<210> SEQ ID NO 19
<211> LENGTH: 487
<212> TYPE: PRT
<213> ORGANISM: Chlamydia psittaci

<400> SEQUENCE: 19

Met Ser Asp Val Tyr Ala Asp Trp Glu Ser Val Ile Gly Leu Glu Val
1               5                   10                  15

His Val Glu Leu Asn Thr Lys Ser Lys Leu Phe Ser Cys Ala Arg Asn
            20                  25                  30

Arg Phe Gly Asp Glu Pro Asn Thr Asn Ile Ser Pro Val Cys Thr Gly
        35                  40                  45

Met Pro Gly Ser Leu Pro Val Leu Asn Lys Glu Ala Val Arg Lys Ala
    50                  55                  60

Val Leu Phe Gly Cys Ala Val Glu Gly Glu Val Ala Leu Leu Ser Arg
65                  70                  75                  80

Phe Asp Arg Lys Ser Tyr Phe Tyr Pro Asp Ser Pro Arg Asn Phe Gln
                85                  90                  95

Ile Thr Gln Phe Glu His Pro Ile Val Arg Gly Gly His Ile Lys Ala
            100                 105                 110

Ile Val His Gly Glu Glu Arg His Phe Glu Leu Ala Gln Ala His Ile
        115                 120                 125

Glu Asp Asp Ala Gly Met Leu Lys His Phe Gly Glu Phe Ala Gly Val
    130                 135                 140

Asp Tyr Asn Arg Ala Gly Val Pro Leu Ile Glu Ile Val Ser Lys Pro
145                 150                 155                 160

Cys Met Phe Cys Ala Asp Asp Ala Val Ala Tyr Ala Thr Ala Leu Val
                165                 170                 175

Ser Leu Leu Asp Tyr Ile Gly Ile Ser Asp Cys Asn Met Glu Glu Gly
            180                 185                 190

Ser Val Arg Phe Asp Val Asn Ile Ser Val Arg Pro Lys Gly Ser Glu
        195                 200                 205

Glu Leu Arg Asn Lys Val Glu Ile Lys Asn Met Asn Ser Phe Ala Phe
    210                 215                 220

Met Ala Gln Ala Leu Glu Ala Glu Arg Cys Arg Gln Ile Asp Ala Tyr
225                 230                 235                 240

Leu Asp Asn Pro Asn Ala Asp Pro Lys Thr Val Ile Pro Gly Ala Thr
                245                 250                 255

Tyr Arg Trp Asp Pro Glu Lys Lys Lys Thr Val Leu Met Arg Leu Lys
            260                 265                 270

Glu Arg Ala Glu Asp Tyr Lys Tyr Phe Ile Glu Pro Asp Leu Pro Val
        275                 280                 285

Leu Gln Leu Thr Glu Ala Tyr Ile Asp Glu Ile Arg His Thr Leu Pro
    290                 295                 300

Glu Leu Pro Phe Asn Lys Tyr Gln Arg Tyr Leu His Glu Tyr Ala Leu
305                 310                 315                 320

Ala Glu Asp Ile Ala Ala Ile Leu Ile Ser Asp Lys His Ser Ala His
                325                 330                 335

Phe Phe Glu Leu Ala Ala Gln Glu Cys Lys Asn Tyr Arg Ala Leu Ser
```

```
                      340               345                350
Asn Trp Leu Thr Val Glu Phe Ala Gly Arg Cys Lys Leu Lys Gly Lys
            355                 360                 365

Asn Leu Ala Phe Ser Gly Ile Leu Pro Ser Val Ala Gln Leu Val
    370                 375                 380

Asn Phe Ile Asp Gln Gly Val Ile Thr Gly Lys Ile Ala Lys Asp Ile
385                 390                 395                 400

Ala Asp Met Met Met Glu Ser Pro Glu Lys Ser Pro Glu Thr Ile Leu
                405                 410                 415

Lys Glu Asn Pro Glu Met Leu Pro Met Thr Asp Glu Ser Ala Leu Val
                420                 425                 430

Ala Ile Ile Ser Glu Val Ile Thr Ala Asn Pro Gln Ser Val Val Asp
            435                 440                 445

Tyr Lys Ser Gly Lys Thr Lys Ala Leu Gly Phe Leu Val Gly Gln Ile
        450                 455                 460

Met Lys Arg Thr Gln Gly Lys Ala Pro Pro Asn Arg Val Asn Glu Leu
465                 470                 475                 480

Leu Leu Val Glu Leu Ser Lys
                485

<210> SEQ ID NO 20
<211> LENGTH: 379
<212> TYPE: DNA
<213> ORGANISM: Chlamydia psittaci

<400> SEQUENCE: 20
tatttagtgt cgaaaacaa cgccaacatt tacgcaggtt ctctctatta tcagcatatc        60
tcctattgga gcgcttggca gaatctgcta caaaacacta tcggtgcaga agctccgtta      120
gtccttaacg cacagttaac ttattgtcat gcttcaaacg acatgaaaac caacatgacg      180
actacttacg ctcctcgtaa aacaacgtat gcagaaatca gggtgattg gggtaacgat       240 tgtttcggag tcgagcttgg tgcaactgtg cctatccaaa cagaatcttc tctcctattc      300
gatatgtact cacctttcct gaagtttcaa cttgtgcata cgcaccaaga tgactttaag      360
gaaaacaata gcgatcagg                                                    379

<210> SEQ ID NO 21
<211> LENGTH: 126
<212> TYPE: PRT
<213> ORGANISM: Chlamydia psittaci

<400> SEQUENCE: 21

Tyr Leu Val Ser Lys Asn Asn Ala Asn Ile Tyr Ala Gly Ser Leu Tyr
1               5                   10                  15

Tyr Gln His Ile Ser Tyr Trp Ser Ala Trp Gln Asn Leu Leu Gln Asn
                20                  25                  30

Thr Ile Gly Ala Glu Ala Pro Leu Val Leu Asn Ala Gln Leu Thr Tyr
            35                  40                  45

Cys His Ala Ser Asn Asp Met Lys Thr Asn Met Thr Thr Thr Tyr Ala
        50                  55                  60

Pro Arg Lys Thr Thr Tyr Ala Glu Ile Lys Gly Asp Trp Gly Asn Asp
65                  70                  75                  80

Cys Phe Gly Val Glu Leu Gly Ala Thr Val Pro Ile Gln Thr Glu Ser
                85                  90                  95

Ser Leu Leu Phe Asp Met Tyr Ser Pro Phe Leu Lys Phe Gln Leu Val
                100                 105                 110
```

His Thr His Gln Asp Asp Phe Lys Glu Asn Asn Ser Asp Gln
    115                 120                 125

<210> SEQ ID NO 22
<211> LENGTH: 2520
<212> TYPE: DNA
<213> ORGANISM: Chlamydia psittaci

<400> SEQUENCE: 22

| | | | | |
|---|---|---|---|---|
| atgaaacatc | cagtctactg | gttcttaata | tcctcgagcc | tatttgcctc gaattctttg | 60 |
| agcttcgcta | acgacgctca | aacagcctta | actccctccg | atagctataa tggaaatgtg | 120 |
| acctctgagg | agttccaggt | aaaagaaact | tcatcaggaa | caacgtatac ttgtgaaggc | 180 |
| aatgtgtgta | tctcctttgc | agggaaagat | tcaggtctaa | agaaaagttg tttctcagct | 240 |
| actgataacc | ttaccttcct | aggaaacggg | tatactcttt | gctttgataa tattactact | 300 |
| acagctagta | accccggagc | cattaatgtt | caaggtcaag | gaaaaacctt aggcatctca | 360 |
| ggatttttctt | tattttcatg | tgcttattgt | cctccaggca | aactggtta cggagctata | 420 |
| cagactaaag | gcaacacaac | tttaaagat | aactctagtc | ttgtcttcca taaaaactgc | 480 |
| tcaacagcag | aaggtggggc | tatccagtgt | aaaggaagca | gtgatgctga attaaaaata | 540 |
| gaaataatc | agaatctggt | tttctcagaa | actcctcca | cttcaaaagg cggggctatt | 600 |
| tatgctgata | aactccaccat | tgtctcaggt | gggcctacat | tattttctaa caactctgta | 660 |
| tccaacggtt | catcccctaa | aggcggagct | attagcataa | agattcaag tggtgaatgt | 720 |
| agcctaaccg | ctgatctcgg | agatattacc | ttcgatggga | caaaatcat caaaactagt | 780 |
| ggtggaagtt | ctacagtaac | aagaaattcc | atagatctcg | gcacagggaa atttacaaag | 840 |
| ctacgtgcta | aagacggctt | cggaattttc | ttctatgacc | ctattactgg gggaggatct | 900 |
| gatgaactaa | acattaataa | aaaagaaact | gttgattata | caggaaagat cgtcttctca | 960 |
| ggtgaaaaat | tatccgatga | agaaaaagca | cgagcggaaa | acctagcttc tactttcaac | 1020 |
| caacccatca | cattatcagc | aggatctctt | gtacttaaag | atggtgtatc tgtaaccgca | 1080 |
| aaacaagtaa | cgcaggaagc | gggatctacc | gttgtcatgg | atctagggac acattacag | 1140 |
| acgccttctt | caggtggaga | accatcacc | ctaactaatc | tagatattaa catcgcctcg | 1200 |
| ttgggggggg | gggggggtac | ctctcctgct | aaactcgcaa | caaatacagc aagtcaagct | 1260 |
| ataactatta | acgctgtcaa | tctagtcgat | gctgatggca | atgcttatga agatcctatt | 1320 |
| cttgctacgt | ctaaaccttt | cacagcaata | gtagctacaa | ctaacgctag tacagtcaca | 1380 |
| cagcctacag | ataatctaac | aaattatgtc | cctcctactc | attacggtta ccaaggaaat | 1440 |
| tggacagtaa | cttgggacac | cgaaacagct | acaaaaacag | ccactctaac ttgggaacaa | 1500 |
| actggctact | cccctaaccc | agaacgtcaa | ggaccttag | tcccgaatac tctttggggt | 1560 |
| gcattctctg | acctcagagc | tatacaaaac | ttaatggata | ttagcgtcaa tggcgctgac | 1620 |
| taccatagag | gttttttggt | atccggtcta | gctaacttct | tacacaaaag tggctctgat | 1680 |
| actaaacgca | agttccgtca | aatagcgcc | ggatacgctt | taggcgtcta cgcaaaaact | 1740 |
| ccttctgatg | atatttttcag | tgcggctttc | tgccaactct | tcggaaagga caaagactat | 1800 |
| ttagtgtcga | aaaacaacgc | caacatttac | gcaggttctc | tctattatca gcatatctcc | 1860 |
| tattggagcg | cttggcagaa | tctgctacaa | aacactatcg | gtgcagaagc tccgttagtc | 1920 |
| cttaacgcac | agttaactta | ttgtcatgct | tcaaacgaca | tgaaaaccaa catgacgact | 1980 |
| acttacgctc | tcgtaaaac | aacgtatgca | gaaatcaagg | gtgattgggg taacgattgt | 2040 |
| ttcggagtcg | agcttggtgc | aactgtgcct | atccaaacag | aatcttctct cctattcgat | 2100 |

```
atgtactcac ctttcctgaa gtttcaactt gtgcatacgc accaagatga ctttaaggaa   2160
aacaatagcg atcagggaag atacttcgaa agcagcaatc tcaccaacct ttctctgcct   2220
atcggcatca agtttgagag atttgctaac aacgatacag cttcttatca tgtcactgct   2280
gcttattctc ctgatatcgt aagaagtaac cctgactgta ctacttctct gttagtaagc   2340
cccgactctg ctgtctgggt aacgaaagcc aacaaccttg cgcgaagcgc cttcatgcta   2400
caagcaggaa actacttgtc tttaagtcac aacatagaaa tcttcagcca gttcggtttc   2460
gagctcaggg gatcttcacg aacctataac gtagatctcg gatcgaagat ccagttctaa   2520
```

<210> SEQ ID NO 23
<211> LENGTH: 839
<212> TYPE: PRT
<213> ORGANISM: Chlamydia psittaci

<400> SEQUENCE: 23

```
Met Lys His Pro Val Tyr Trp Phe Leu Ile Ser Ser Ser Leu Phe Ala
1               5                   10                  15

Ser Asn Ser Leu Ser Phe Ala Asn Asp Ala Gln Thr Ala Leu Thr Pro
            20                  25                  30

Ser Asp Ser Tyr Asn Gly Asn Val Thr Ser Glu Glu Phe Gln Val Lys
        35                  40                  45

Glu Thr Ser Ser Gly Thr Thr Tyr Thr Cys Glu Gly Asn Val Cys Ile
    50                  55                  60

Ser Phe Ala Gly Lys Asp Ser Gly Leu Lys Lys Ser Cys Phe Ser Ala
65                  70                  75                  80

Thr Asp Asn Leu Thr Phe Leu Gly Asn Gly Tyr Thr Leu Cys Phe Asp
                85                  90                  95

Asn Ile Thr Thr Thr Ala Ser Asn Pro Gly Ala Ile Asn Val Gln Gly
            100                 105                 110

Gln Gly Lys Thr Leu Gly Ile Ser Gly Phe Ser Leu Phe Ser Cys Ala
        115                 120                 125

Tyr Cys Pro Pro Gly Thr Thr Gly Tyr Gly Ala Ile Gln Thr Lys Gly
    130                 135                 140

Asn Thr Thr Leu Lys Asp Asn Ser Ser Leu Val Phe His Lys Asn Cys
145                 150                 155                 160

Ser Thr Ala Glu Gly Gly Ala Ile Gln Cys Lys Gly Ser Ser Asp Ala
                165                 170                 175

Glu Leu Lys Ile Glu Asn Asn Gln Asn Leu Val Phe Ser Glu Asn Ser
            180                 185                 190

Ser Thr Ser Lys Gly Gly Ala Ile Tyr Ala Asp Lys Leu Thr Ile Val
        195                 200                 205

Ser Gly Gly Pro Thr Leu Phe Ser Asn Asn Ser Val Ser Asn Gly Ser
    210                 215                 220

Ser Pro Lys Gly Gly Ala Ile Ser Ile Lys Asp Ser Ser Gly Glu Cys
225                 230                 235                 240

Ser Leu Thr Ala Asp Leu Gly Asp Ile Thr Phe Asp Gly Asn Lys Ile
                245                 250                 255

Ile Lys Thr Ser Gly Gly Ser Ser Thr Val Thr Arg Asn Ser Ile Asp
            260                 265                 270

Leu Gly Thr Gly Lys Phe Thr Lys Leu Arg Ala Lys Asp Gly Phe Gly
        275                 280                 285

Ile Phe Phe Tyr Asp Pro Ile Thr Gly Gly Gly Ser Asp Glu Leu Asn
    290                 295                 300
```

```
Ile Asn Lys Lys Glu Thr Val Asp Tyr Thr Gly Lys Ile Val Phe Ser
305                 310                 315                 320

Gly Glu Lys Leu Ser Asp Glu Lys Ala Arg Ala Glu Asn Leu Ala
            325                 330                 335

Ser Thr Phe Asn Gln Pro Ile Thr Leu Ser Ala Gly Ser Leu Val Leu
            340                 345                 350

Lys Asp Gly Val Ser Val Thr Ala Lys Gln Val Thr Gln Glu Ala Gly
            355                 360                 365

Ser Thr Val Val Met Asp Leu Gly Thr Thr Leu Gln Thr Pro Ser Ser
370                 375                 380

Gly Gly Glu Thr Ile Thr Leu Thr Asn Leu Asp Ile Asn Ile Ala Ser
385                 390                 395                 400

Leu Gly Gly Gly Gly Thr Ser Pro Ala Lys Leu Ala Thr Asn Thr
            405                 410                 415

Ala Ser Gln Ala Ile Thr Ile Asn Ala Val Asn Leu Val Asp Ala Asp
            420                 425                 430

Gly Asn Ala Tyr Glu Asp Pro Ile Leu Ala Thr Ser Lys Pro Phe Thr
            435                 440                 445

Ala Ile Val Ala Thr Thr Asn Ala Ser Thr Val Thr Gln Pro Thr Asp
450                 455                 460

Asn Leu Thr Asn Tyr Val Pro Pro Thr His Tyr Gly Tyr Gln Gly Asn
465                 470                 475                 480

Trp Thr Val Thr Trp Asp Thr Glu Thr Ala Lys Thr Ala Thr Leu
            485                 490                 495

Thr Trp Glu Gln Thr Gly Tyr Ser Pro Asn Pro Glu Arg Gln Gly Pro
            500                 505                 510

Leu Val Pro Asn Thr Leu Trp Gly Ala Phe Ser Asp Leu Arg Ala Ile
            515                 520                 525

Gln Asn Leu Met Asp Ile Ser Val Asn Gly Ala Asp Tyr His Arg Gly
530                 535                 540

Phe Trp Val Ser Gly Leu Ala Asn Phe Leu His Lys Ser Gly Ser Asp
545                 550                 555                 560

Thr Lys Arg Lys Phe Arg His Asn Ser Ala Gly Tyr Ala Leu Gly Val
            565                 570                 575

Tyr Ala Lys Thr Pro Ser Asp Asp Ile Phe Ser Ala Ala Phe Cys Gln
            580                 585                 590

Leu Phe Gly Lys Asp Lys Asp Tyr Leu Val Ser Lys Asn Asn Ala Asn
            595                 600                 605

Ile Tyr Ala Gly Ser Leu Tyr Tyr Gln His Ile Ser Tyr Trp Ser Ala
610                 615                 620

Trp Gln Asn Leu Leu Gln Asn Thr Ile Gly Ala Glu Ala Pro Leu Val
625                 630                 635                 640

Leu Asn Ala Gln Leu Thr Tyr Cys His Ala Ser Asn Asp Met Lys Thr
            645                 650                 655

Asn Met Thr Thr Thr Tyr Ala Pro Arg Lys Thr Thr Tyr Ala Glu Ile
            660                 665                 670

Lys Gly Asp Trp Gly Asn Asp Cys Phe Gly Val Glu Leu Gly Ala Thr
            675                 680                 685

Val Pro Ile Gln Thr Glu Ser Ser Leu Leu Phe Asp Met Tyr Ser Pro
690                 695                 700

Phe Leu Lys Phe Gln Leu Val His Thr His Gln Asp Asp Phe Lys Glu
705                 710                 715                 720

Asn Asn Ser Asp Gln Gly Arg Tyr Phe Glu Ser Ser Asn Leu Thr Asn
            725                 730                 735
```

```
Leu Ser Leu Pro Ile Gly Ile Lys Phe Glu Arg Phe Ala Asn Asn Asp
            740                 745                 750

Thr Ala Ser Tyr His Val Thr Ala Ala Tyr Ser Pro Asp Ile Val Arg
            755                 760                 765

Ser Asn Pro Asp Cys Thr Thr Ser Leu Leu Val Ser Pro Asp Ser Ala
            770                 775                 780

Val Trp Val Thr Lys Ala Asn Asn Leu Ala Arg Ser Ala Phe Met Leu
785                 790                 795                 800

Gln Ala Gly Asn Tyr Leu Ser Leu Ser His Asn Ile Glu Ile Phe Ser
            805                 810                 815

Gln Phe Gly Phe Glu Leu Arg Gly Ser Ser Arg Thr Tyr Asn Val Asp
            820                 825                 830

Leu Gly Ser Lys Ile Gln Phe
            835

<210> SEQ ID NO 24
<211> LENGTH: 1039
<212> TYPE: DNA
<213> ORGANISM: Chlamydia psittaci

<400> SEQUENCE: 24
aaacgttttc atattaatgg ggttcctgaa tggtctttat ctacgcctta ttctcttgct     60
atggggtata atatcttggc tacgggagtg cagatggtta agcctatgc cattcttgcc    120
aacggtggtt atgatgtgcg ccctaccttg ataaaaaaaa tagtcactac ttctggaaaa    180
gagtacgtgt tgcatcctca agttcgtgga gaaagaattc tttctcagga cattgtggat    240
gaggtattga agctacgcg ttttactacc tatcctggag aacgggatt tcgggctgcg    300
cctaaaaagc attccagtgc agggaaaaca ggaacaacag aaaagctagt tcatggaaag    360
tatgataagc atcggcatat ttcttcattt ataggtatca cgccgatata cccttcggca    420
gggggggagtg ttcctttggt catgcttgtc tctatcagtt atacgaccga caacggtagt    480
caagtgtacg tcgttcaatt gcgacatgag ggtatcgaaa tctgtcgtca attcgtccat    540
gttaacctaa ttgtgtggtc attatcgctt tctttatact acttaccgta gttcctacgg    600
atactagcaa aaagttctgc tctttgcgtt gctctttgaa cagcatactg tactttaaa    660
aagtctgcta aattttcccg ttctccattc ctatctgaga agtagagaag gctctatttt    720
aacacttctt ctccagaaga cacccaattg accatcttac gggcaacgga ctcgtgttct    780
tcttcttttt tggtttgtaa gttttgttgc gtatgctcag ctatatcatt cagatcacca    840
ttgattaaat caatgatcac actgacagct tcaaaatgtt cttgcgatag tttatttga    900
tcttgttgta gagtggattg tgcatcccat aaacgctctt ttagattgtt tatttgctct    960
ttcagctctt ccgaatctaa cgcctcttcc agttcaggat cgataatgtt agagtttctg   1020
tcttgcatca tcgccatag                                                1039

<210> SEQ ID NO 25
<211> LENGTH: 196
<212> TYPE: PRT
<213> ORGANISM: Chlamydia psittaci

<400> SEQUENCE: 25

Lys Arg Phe His Ile Asn Gly Val Pro Glu Trp Ser Leu Ser Thr Pro
1               5                   10                  15

Tyr Ser Leu Ala Met Gly Tyr Asn Ile Leu Ala Thr Gly Val Gln Met
            20                  25                  30
```

```
Val Lys Ala Tyr Ala Ile Leu Ala Asn Gly Gly Tyr Asp Val Arg Pro
        35                  40                  45
Thr Leu Ile Lys Lys Ile Val Thr Thr Ser Gly Lys Glu Tyr Val Leu
    50                  55                  60
His Pro Gln Val Arg Gly Glu Arg Ile Leu Ser Gln Asp Ile Val Asp
65                  70                  75                  80
Glu Val Leu Lys Ala Thr Arg Phe Thr Thr Tyr Pro Gly Gly Thr Gly
                85                  90                  95
Phe Arg Ala Ala Pro Lys Lys His Ser Ser Ala Gly Lys Thr Gly Thr
            100                 105                 110
Thr Glu Lys Leu Val His Gly Lys Tyr Asp Lys His Arg His Ile Ser
        115                 120                 125
Ser Phe Ile Gly Ile Thr Pro Ile Tyr Pro Ser Ala Gly Gly Ser Val
    130                 135                 140
Pro Leu Val Met Leu Val Ser Ile Ser Tyr Thr Thr Asp Asn Gly Ser
145                 150                 155                 160
Gln Val Tyr Val Val Gln Leu Arg His Glu Gly Ile Glu Ile Cys Arg
                165                 170                 175
Gln Phe Val His Val Asn Leu Ile Val Trp Ser Leu Ser Leu Ser Leu
            180                 185                 190
Tyr Tyr Leu Pro
        195

<210> SEQ ID NO 26
<211> LENGTH: 1950
<212> TYPE: DNA
<213> ORGANISM: Chlamydia psittaci

<400> SEQUENCE: 26
atgaatcacc gtaaatgctt aaccatgatt acctatggag ttctgctctc ctattctttc      60
ctgatcatac ggtattataa aattcagatt tgtgaggaga aacgttgggc agcagaagct     120
ttaggacaac atgaatttcg agtaaaggac ccttttcgta gggggacgtt ttttctcag     180
atgaatttac gtaagggaga ttcagagcaa cgacaagctc tggccgtgga cattacgaaa     240
tttcatcttt gtttagatgc tgtagctgtt cctgaagaac accgtgatgt gattgctaag     300
aaagttttta gtctcattgg agaaggtgat tatgacaaac tccgtgcgga gtttgataaa     360
aaatctcgct atcgaaagtt atttctttgg ttagatcgtg cggatcatga ccgcatcctg     420
tcttggtggc gggggtacgc agcaaaatct aaaatacccct cgaatgcttt gttttcatg     480
accgactatc aaagatctta tccctttggc aaacttttag gccaagttct acatactctg     540
agagaagtca aggatgagaa acaggcaaa gctttcccta caggagggttt agaagcctat     600
tttaaccacg tccttgaagg agagccagga gaacggaaat tcctacgttc tcctttaaat     660
cgtttagatc tagataaagt cacaaagatt cctagggatg gttcggatat ttatctcaca     720
gtcaatccct gtatacagac tatagcggaa gaggaattag aaaaagggt aaaggaagcc     780
aaagctaaag gtgggcgtct aatttttaatg aatgcttata caggcgagat tcttgcttta     840
gcacagtatc ctttcttta tccttcggaa tacaaggaat ttttcaatga taggaaaaa     900
atagagcaca caaaagtaac atcagtcagt gatgtgtttg aacccggctc tatcatgaaa     960
cctctgactc tggctatagc gttgctggcc aacgaagaga tggtgaaaag atcaggaaag    1020
ccctttatttg atcctaatga acctatagat gtaaccccgca ggattttccc aggaagaaag    1080
caattttccgc ttaggatat ctcatcgaat cggcgtttaa atatgtacat ggcgattcaa    1140
aagtcttcga acgttattgt agcgcaactt gctgatcta tagtgcaaca tctagggaac    1200
```
cactggtatg aagacaagtt attgttatta ggatttggta aaaagacggg gatagaattg 1260
ccaggggaag cgtcaggatt ggtaccttca cctaaacgtt ttcatattaa tggggttcct 1320
gaatggtctt tatctacgcc ttattctctt gctatggggt ataatatctt ggctacggga 1380
gtgcagatgg ttaaagccta tgccattctt gccaacggtg gttatgatgt gcgccctacc 1440
ttgataaaaa aaatagtcac tacttctgga aaagagtacg tgttgcatcc tcaagttcgt 1500
ggagaaagaa ttctttctca ggacattgtg gatgaggtat tgaaagctac gcgttttact 1560
acctatcctg gaggaacggg atttcgggct gcgcctaaaa agcattccag tgcagggaaa 1620
acaggaacaa cagaaaagct agttcatgga aagtatgata agcatcggca tatttcttca 1680
tttataggta tcacgccgat ataccccttcg gcaggggggga gtgttccttt ggtcatgctt 1740
gtctctatag atgatcctga tcattgtgtt cgcgaggatg gaacaaagaa ctatatggga 1800
ggccgatgtg ccgcccctgt atttggcaga gttgcggatc gtgttttatc ttatctagga 1860
gttcccgaag ataaagaaaa atacagttat cagagtgagg tggctgctat gaaagctttg 1920
tatgaggaat ggaatcgttc ggggaaataa 1950

<210> SEQ ID NO 27
<211> LENGTH: 649
<212> TYPE: PRT
<213> ORGANISM: Chlamydia psittaci

<400> SEQUENCE: 27

Met Asn His Arg Lys Cys Leu Thr Met Ile Thr Tyr Gly Val Leu Leu
1 5 10 15

Ser Tyr Ser Phe Leu Ile Ile Arg Tyr Tyr Lys Ile Gln Ile Cys Glu
20 25 30

Glu Lys Arg Trp Ala Ala Glu Ala Leu Gly Gln His Glu Phe Arg Val
35 40 45

Lys Asp Pro Phe Arg Arg Gly Thr Phe Phe Ser Gln Met Asn Leu Arg
50 55 60

Lys Gly Asp Ser Glu Gln Arg Gln Ala Leu Ala Val Asp Ile Thr Lys
65 70 75 80

Phe His Leu Cys Leu Asp Ala Val Ala Val Pro Glu Glu His Arg Asp
85 90 95

Val Ile Ala Lys Lys Val Phe Ser Leu Ile Gly Glu Gly Asp Tyr Asp
100 105 110

Lys Leu Arg Ala Glu Phe Asp Lys Lys Ser Arg Tyr Arg Lys Leu Phe
115 120 125

Leu Trp Leu Asp Arg Ala Asp His Asp Arg Ile Leu Ser Trp Trp Arg
130 135 140

Gly Tyr Ala Ala Lys Ser Lys Ile Pro Ser Asn Ala Leu Phe Phe Met
145 150 155 160

Thr Asp Tyr Gln Arg Ser Tyr Pro Phe Gly Lys Leu Leu Gly Gln Val
165 170 175

Leu His Thr Leu Arg Glu Val Lys Asp Glu Lys Thr Gly Lys Ala Phe
180 185 190

Pro Thr Gly Gly Leu Glu Ala Tyr Phe Asn His Val Leu Glu Gly Glu
195 200 205

Pro Gly Glu Arg Lys Phe Leu Arg Ser Pro Leu Asn Arg Leu Asp Leu
210 215 220

Asp Lys Val Thr Lys Ile Pro Arg Asp Gly Ser Asp Ile Tyr Leu Thr
225 230 235 240

```
Val Asn Pro Cys Ile Gln Thr Ile Ala Glu Glu Leu Glu Lys Gly
            245                 250                 255
Val Lys Glu Ala Lys Ala Lys Gly Gly Arg Leu Ile Leu Met Asn Ala
        260                 265                 270
Tyr Thr Gly Glu Ile Leu Ala Leu Ala Gln Tyr Pro Phe Phe Asn Pro
        275                 280                 285
Ser Glu Tyr Lys Glu Phe Phe Asn Asp Lys Glu Lys Ile Glu His Thr
        290                 295                 300
Lys Val Thr Ser Val Ser Asp Val Phe Glu Pro Gly Ser Ile Met Lys
305                 310                 315                 320
Pro Leu Thr Leu Ala Ile Ala Leu Leu Ala Asn Glu Glu Met Val Lys
                325                 330                 335
Arg Ser Gly Lys Pro Leu Phe Asp Pro Asn Glu Pro Ile Asp Val Thr
            340                 345                 350
Arg Arg Ile Phe Pro Gly Arg Lys Gln Phe Pro Leu Lys Asp Ile Ser
        355                 360                 365
Ser Asn Arg Arg Leu Asn Met Tyr Met Ala Ile Gln Lys Ser Ser Asn
    370                 375                 380
Val Tyr Val Ala Gln Leu Ala Asp Leu Ile Val Gln His Leu Gly Asn
385                 390                 395                 400
His Trp Tyr Glu Asp Lys Leu Leu Leu Leu Gly Phe Gly Lys Lys Thr
                405                 410                 415
Gly Ile Glu Leu Pro Gly Glu Ala Ser Gly Leu Val Pro Ser Pro Lys
            420                 425                 430
Arg Phe His Ile Asn Gly Val Pro Glu Trp Ser Leu Ser Thr Pro Tyr
        435                 440                 445
Ser Leu Ala Met Gly Tyr Asn Ile Leu Ala Thr Gly Val Gln Met Val
450                 455                 460
Lys Ala Tyr Ala Ile Leu Ala Asn Gly Gly Tyr Asp Val Arg Pro Thr
465                 470                 475                 480
Leu Ile Lys Lys Ile Val Thr Thr Ser Gly Lys Glu Tyr Val Leu His
                485                 490                 495
Pro Gln Val Arg Gly Glu Arg Ile Leu Ser Gln Asp Ile Val Asp Glu
            500                 505                 510
Val Leu Lys Ala Thr Arg Phe Thr Thr Tyr Pro Gly Gly Thr Gly Phe
        515                 520                 525
Arg Ala Ala Pro Lys Lys His Ser Ser Ala Gly Lys Thr Gly Thr Thr
    530                 535                 540
Glu Lys Leu Val His Gly Lys Tyr Asp Lys His Arg His Ile Ser Ser
545                 550                 555                 560
Phe Ile Gly Ile Thr Pro Ile Tyr Pro Ser Ala Gly Gly Ser Val Pro
                565                 570                 575
Leu Val Met Leu Val Ser Ile Asp Asp Pro Asp His Cys Val Arg Glu
            580                 585                 590
Asp Gly Thr Lys Asn Tyr Met Gly Gly Arg Cys Ala Ala Pro Val Phe
        595                 600                 605
Gly Arg Val Ala Asp Arg Val Leu Ser Tyr Leu Gly Val Pro Glu Asp
    610                 615                 620
Lys Glu Lys Tyr Ser Tyr Gln Ser Glu Val Ala Ala Met Lys Ala Leu
625                 630                 635                 640
Tyr Glu Glu Trp Asn Arg Ser Gly Lys
                645

<210> SEQ ID NO 28
```

-continued

```
<211> LENGTH: 960
<212> TYPE: DNA
<213> ORGANISM: Chlamydia psittaci

<400> SEQUENCE: 28
atgttcaata agctcattga acagcacag  aaacgggtgg aagcaagaaa ctatactatt    60
cgaaagcata ctcttgagta tgacgatgtt atgaataggc aaaggcagac gatctatgct   120
tttcgtaatg acgttatccg ctctgaagat atctttggtt tagctaagga agcaatatct   180
catgttgcat taatgatcgc ttcgttgata gtgagccgtg atcatcctac agggaattct   240
cttcctaggc tggaagaatg gatgaactat tcttcccac  tgcaattgaa attgaagaa    300 ttgaaaagat tgaagtctat agatgccatt gccgaacggg ttgctgatga tctcatagaa   360
gttttccaga taagtttgc  ttctatggtg caggaaatta ccgaagcagc cggagaaaaa   420
gtcgatgcta atggtgtctg taaagatgtt attcgctcgg tcatgattat gcatatcgat   480
gagcagtgga aaattcatct tgtagatatg gatttattac gtagtgaagt aggtttacgt   540
actgtcggtc agaaagaccc tcttatcgaa tttaaacatg agtcgttctt actattcgaa   600
agtcttattc gcgatattcg tattgctatt gtaaagcatt gttccgtttt agagttgacg   660
atgactagag aacagcggcc tcaaaatgtc gtgcctgttg ttgccacatc tttccaaaat   720
aatgaaaatt tcggtccttt ggaactcaca gttatcagtg attctgacga tgaataaaaa   780
gagctttagg gctgggctag cttccagcct tttcccttac gttattgatt tatagtttta   840
aataaatacg gaccactcag accaggattg tgtgtcgtgg tggcgtatcc aaaatgttct   900
gtgattatcc tcaatcagaa attgtacatg atgatcgcga ttgcgtgttg tcatgcaaat   960

<210> SEQ ID NO 29
<211> LENGTH: 258
<212> TYPE: PRT
<213> ORGANISM: Chlamydia psittaci

<400> SEQUENCE: 29

Met Phe Asn Lys Leu Ile Glu Thr Ala Gln Lys Arg Val Glu Ala Arg
1               5                   10                  15

Asn Tyr Thr Ile Arg Lys His Thr Leu Glu Tyr Asp Asp Val Met Asn
                20                  25                  30

Arg Gln Arg Gln Thr Ile Tyr Ala Phe Arg Asn Asp Val Ile Arg Ser
            35                  40                  45

Glu Asp Ile Phe Gly Leu Ala Lys Glu Ala Ile Ser His Val Ala Leu
        50                  55                  60

Met Ile Ala Ser Leu Ile Val Ser Arg Asp His Pro Thr Gly Asn Ser
65                  70                  75                  80

Leu Pro Arg Leu Glu Glu Trp Met Asn Tyr Ser Phe Pro Leu Gln Leu
                85                  90                  95

Asn Ile Glu Glu Leu Lys Arg Leu Lys Ser Ile Asp Ala Ile Ala Glu
            100                 105                 110

Arg Val Ala Asp Asp Leu Ile Glu Val Phe Gln Asn Lys Phe Ala Ser
        115                 120                 125

Met Val Gln Glu Ile Thr Glu Ala Ala Gly Glu Lys Val Asp Ala Asn
    130                 135                 140

Gly Val Cys Lys Asp Val Ile Arg Ser Val Met Ile Met His Ile Asp
145                 150                 155                 160

Glu Gln Trp Lys Ile His Leu Val Asp Met Asp Leu Leu Arg Ser Glu
                165                 170                 175

Val Gly Leu Arg Thr Val Gly Gln Lys Asp Pro Leu Ile Glu Phe Lys
```

```
                    180               185               190
His Glu Ser Phe Leu Leu Phe Glu Ser Leu Ile Arg Asp Ile Arg Ile
            195                       200                   205

Ala Ile Val Lys His Leu Phe Arg Leu Glu Leu Thr Met Thr Arg Glu
210                     215                       220

Gln Arg Pro Gln Asn Val Val Pro Val Val Ala Thr Ser Phe Gln Asn
225                 230                     235                 240

Asn Glu Asn Phe Gly Pro Leu Glu Leu Thr Val Ile Ser Asp Ser Asp
                245                     250                     255

Asp Glu
```

<210> SEQ ID NO 30
<211> LENGTH: 697
<212> TYPE: DNA
<213> ORGANISM: Chlamydia psittaci

<400> SEQUENCE: 30

```
gggtttgatt atctcagaga taattctatt gcaacttctg tggatgagca ggtgggacgt    60
gggttttatt ttgctattat cgatgaagtc gactcgattt taattgatga agccagaact   120
cctttaatta tttctggtcc tggggaaaaa cataatcctg tgtatttcga actcaaagat   180
aaagtggctg acctcgttca gttacaaagg gagttatgta accagttagc tcttgaagct   240
agacggggac tagaattgtt cttggatatg gatattcttc ctaaggataa aaaagttatc   300
gaagctatct ccgaattttg ccgtagctta tggttagtta gtaagggaat gcctttaaat   360
cgtgttttgc gtagagtgcg cgaacaccca gatttgcgag ccatgataga taatgggat    420
acttattatc atgctgagca aaataaagaa gagagtatag agaagctatc tcagctgtat   480
atcattgttg atgaacataa taacgatttt gaattgacag atcgtggcat gcaacaatgg   540
gtggataagg ctggaggttc tgctgaagat tttgtcatga tggacatggg gcatgaatat   600
gctcttatag atggtgacga taccttatca ccgacagaga aaatcaatag aaaaatagct   660
atttccgaag aagatacgag gagaaaagct cgagctc                            697
```

<210> SEQ ID NO 31
<211> LENGTH: 232
<212> TYPE: PRT
<213> ORGANISM: Chlamydia psittaci

<400> SEQUENCE: 31

```
Gly Phe Asp Tyr Leu Arg Asp Asn Ser Ile Ala Thr Ser Val Asp Glu
1               5                   10                  15

Gln Val Gly Arg Gly Phe Tyr Phe Ala Ile Ile Asp Glu Val Asp Ser
            20                  25                  30

Ile Leu Ile Asp Glu Ala Arg Thr Pro Leu Ile Ile Ser Gly Pro Gly
        35                  40                  45

Glu Lys His Asn Pro Val Tyr Phe Glu Leu Lys Asp Lys Val Ala Asp
    50                  55                  60

Leu Val Gln Leu Gln Arg Glu Leu Cys Asn Gln Leu Ala Leu Glu Ala
65                  70                  75                  80

Arg Arg Gly Leu Glu Leu Phe Leu Asp Met Asp Ile Leu Pro Lys Asp
                85                  90                  95

Lys Lys Val Ile Glu Ala Ile Ser Glu Phe Cys Arg Ser Leu Trp Leu
            100                 105                 110

Val Ser Lys Gly Met Pro Leu Asn Arg Val Leu Arg Arg Val Arg Glu
        115                 120                 125
```

-continued

```
His Pro Asp Leu Arg Ala Met Ile Asp Lys Trp Asp Thr Tyr Tyr His
            130                 135                 140
Ala Glu Gln Asn Lys Glu Ser Ile Glu Lys Leu Ser Gln Leu Tyr
145                 150                 155                 160
Ile Ile Val Asp Glu His Asn Asn Asp Phe Glu Leu Thr Asp Arg Gly
                165                 170                 175
Met Gln Gln Trp Val Asp Lys Ala Gly Gly Ser Ala Glu Asp Phe Val
            180                 185                 190
Met Met Asp Met Gly His Glu Tyr Ala Leu Ile Asp Gly Asp Asp Thr
        195                 200                 205
Leu Ser Pro Thr Glu Lys Ile Asn Arg Lys Ile Ala Ile Ser Glu Glu
    210                 215                 220
Asp Thr Arg Arg Lys Ala Arg Ala
225                 230
```

<210> SEQ ID NO 32
<211> LENGTH: 2910
<212> TYPE: DNA
<213> ORGANISM: Chlamydia psittaci

<400> SEQUENCE: 32

```
atgttagatt tcttaaacg tttctttgga tcttctcaag agcgcacctt aaaaaaattt      60
caaaaacttg tggataaggt caacctctat gatgagatgc tagctccttt gtctgatgag     120
gagttacgta ataaaacagc agagttaaaa aagcgttatc aggacggcga atccttagat     180
gatatgcttc ccgaggctta tgccgtagtg aaaaatgtat gcaggcgttt aacaggaact     240
cctgtagaag tgtcgggtta tcatcaaaat gggacatgg ttccctatga tgtgcaggtt      300
ctcggtgcta tagctatgca taagggcttt ataaccgaga tgcagacagg agaggggaaa     360
actctcaccg ctgttatgcc tctatattta aatgcattga caggcaagcc tgtgcattta     420
gtcacagtga atgattatct cgctcaaagg gattgtgagt gggtcggctc tatattgcgt     480
tggttaggtt taactaccgg agtattgata tcaggatcgc ctttagaaaa agaaaagac      540
atttatcgtt gtgacgttgt ctacggtaca gcatcagagt tcgggtttga ttatctcaga     600
gataattcta ttgcaacttc tgtggatgag caggtgggac gtgggtttta ttttgctatt     660
atcgatgaag tcgactcgat tttaattgat gaagccagaa ctcctttaat tatttctggt     720
cctggggaaa aacataatcc tgtgtatttc gaactcaaag ataaagtggc tgacctcgtt     780
cagttacaaa gggagttatg taaccagtta gctcttgaag ctagacgggg actagaattg     840
ttcttggata tggatattct tcctaaggat aaaaaaagtta tcgaagctat ctccgaattt     900
tgccgtagct tatggttagt tagtaaggga atgcctttaa atcgtgtttt gcgtagagtg     960
cgcgaacacc cagatttgcg agccatgata gataaatggg atacttatta tcatgctgag    1020
caaaataaag aagagagtat agagaagcta tctcagctgt atatcattgt tgatgaacat    1080
aataacgatt ttgaattgac agatcgtggc atgcaacaat gggtggataa ggctggaggt    1140
tctgctgaag attttgtcat gatggacatg gggcatgaat atgctcttat agatggtgac    1200
gatacccttat caccgacaga gaaaatcaat agaaaaatag ctatttccga agaagatacg    1260
aggagaaaag ctcgagctca tggcttgcgc caactattaa gagcgcatct tcttatggaa    1320
cgcgatgtgg attatattgt tcgtaatgat caaattgtca tcattgacga acatacgggc    1380
cgcccgcaac aggtcgtcg ttttttccgaa ggactgcatc aagccataga agcaaaagaa    1440
catgtcacta tccgtaagga atcacaaacg tttgctacag ttaccttaca gaatttcttc    1500
cgtctgtatg aaaaaactcgc aggtatgacg ggaacagcaa ttacggaatc taaagagttt    1560
```

```
aaagagattt ataatctttta tgtattgcag gtgcccacgt ttaaagaatg tttgcgtgta    1620
gatcacaatg acgaatttta tatgacagag cgtgaaaagt accacgcgat tgttaaggaa    1680
attgcccgta tacatgccgt agggaacccg attctcatag aacggagtc tgtagaggtt     1740 tctgagaaac tttctcgtat tttgagacaa aatcgcatag aacatacagt gttaaatgcg    1800
aaaaatcatg ctcaagaagc agagatcatt gcagcagcag gaaagctggg agctgtgact    1860
gtagctacca atatggctgg ccgtggtaca gatattaagc tggatgaaga agctgtagtt    1920
gttggaggtc tccatgttat tggtacgagt cggcaccaat cacgccgtat agataggcag    1980
ttgcgcgggc gttgcgcacg tttaggagat cctggttcgg cgaaatttt cctatctttt     2040 gaagatcgcc tgatgcgctt atttgcatcg cccaagttaa atgccttgat tcgtcatttc    2100
cgtcctcctg aaggagaggc tatgtcggat cctatgttca ataagctcat tgaaacagca    2160
cagaaacggg tggaagcaag aaactatact attcgaaagc atactcttga gtatgacgat    2220
gttatgaata ggcaaaggca gacgatctat gcttttcgta atgacgttat ccgctctgaa    2280
gatatctttg gtttagctaa ggaagcaata tctcatgttg cattaatgat cgcttcgttg    2340
atagtgagcc gtgatcatcc tacagggaat tctcttccta ggctggaaga atggatgaac    2400 tattcttttcc cactgcaatt gaatattgaa gaattgaaaa gattgaagtc tatagatgcc    2460
attgccgaac gggttgctga tgatctcata gaagttttcc agaataagtt tgcttctatg    2520
gtgcaggaaa ttaccgaagc agccggagaa aaagtcgatg ctaatggtgt ctgtaaagat    2580
gttattcgct cggtcatgat tatgcatatc gatgagcagt ggaaaattca tcttgtagat    2640
atggatttat tacgtagtga agtaggttta cgtactgtcg gtcagaaaga ccctcttatc    2700
gaatttaaac atgagtcgtt cttactattc gaaagtctta ttcgcgatat tcgtattgct    2760
attgtaaagc atttgttccg tttagagttg acgatgacta gagaacagcg gcctcaaaat    2820
gtcgtgcctg ttgttgccac atctttccaa aataatgaaa atttcggtcc tttggaactc    2880
acagttatca gtgattctga cgatgaataa                                      2910
```

<210> SEQ ID NO 33
<211> LENGTH: 969
<212> TYPE: PRT
<213> ORGANISM: Chlamydia psittaci

<400> SEQUENCE: 33

```
Met Leu Asp Phe Leu Lys Arg Phe Phe Gly Ser Ser Gln Glu Arg Thr
1               5                   10                  15

Leu Lys Lys Phe Gln Lys Leu Val Asp Lys Val Asn Leu Tyr Asp Glu
            20                  25                  30

Met Leu Ala Pro Leu Ser Asp Glu Glu Leu Arg Asn Lys Thr Ala Glu
        35                  40                  45

Leu Lys Lys Arg Tyr Gln Asp Gly Glu Ser Leu Asp Asp Met Leu Pro
    50                  55                  60

Glu Ala Tyr Ala Val Val Lys Asn Val Cys Arg Arg Leu Thr Gly Thr
65                  70                  75                  80

Pro Val Glu Val Ser Gly Tyr His Gln Asn Trp Asp Met Val Pro Tyr
                85                  90                  95

Asp Val Gln Val Leu Gly Ala Ile Ala Met His Lys Gly Phe Ile Thr
            100                 105                 110

Glu Met Gln Thr Gly Glu Gly Lys Thr Leu Thr Ala Val Met Pro Leu
        115                 120                 125

Tyr Leu Asn Ala Leu Thr Gly Lys Pro Val His Leu Val Thr Val Asn
```

```
                130                 135                 140
Asp Tyr Leu Ala Gln Arg Asp Cys Glu Trp Val Gly Ser Ile Leu Arg
145                 150                 155                 160

Trp Leu Gly Leu Thr Thr Gly Val Leu Ile Ser Gly Ser Pro Leu Glu
                165                 170                 175

Lys Arg Lys Asp Ile Tyr Arg Cys Asp Val Val Tyr Gly Thr Ala Ser
                180                 185                 190

Glu Phe Gly Phe Asp Tyr Leu Arg Asp Asn Ser Ile Ala Thr Ser Val
                195                 200                 205

Asp Glu Gln Val Gly Arg Gly Phe Tyr Phe Ala Ile Ile Asp Glu Val
210                 215                 220

Asp Ser Ile Leu Ile Asp Glu Ala Arg Thr Pro Leu Ile Ile Ser Gly
225                 230                 235                 240

Pro Gly Glu Lys His Asn Pro Val Tyr Phe Glu Leu Lys Asp Lys Val
                245                 250                 255

Ala Asp Leu Val Gln Leu Gln Arg Glu Leu Cys Asn Gln Leu Ala Leu
                260                 265                 270

Glu Ala Arg Arg Gly Leu Glu Leu Phe Leu Asp Met Asp Ile Leu Pro
                275                 280                 285

Lys Asp Lys Lys Val Ile Glu Ala Ile Ser Glu Phe Cys Arg Ser Leu
290                 295                 300

Trp Leu Val Ser Lys Gly Met Pro Leu Asn Arg Val Leu Arg Arg Val
305                 310                 315                 320

Arg Glu His Pro Asp Leu Arg Ala Met Ile Asp Lys Trp Asp Thr Tyr
                325                 330                 335

Tyr His Ala Glu Gln Asn Lys Glu Glu Ser Ile Glu Lys Leu Ser Gln
                340                 345                 350

Leu Tyr Ile Ile Val Asp Glu His Asn Asn Asp Phe Glu Leu Thr Asp
                355                 360                 365

Arg Gly Met Gln Gln Trp Val Asp Lys Ala Gly Gly Ser Ala Glu Asp
                370                 375                 380

Phe Val Met Met Asp Met Gly His Glu Tyr Ala Leu Ile Asp Gly Asp
385                 390                 395                 400

Asp Thr Leu Ser Pro Thr Glu Lys Ile Asn Arg Lys Ile Ala Ile Ser
                405                 410                 415

Glu Glu Asp Thr Arg Arg Lys Ala Arg Ala His Gly Leu Arg Gln Leu
                420                 425                 430

Leu Arg Ala His Leu Leu Met Glu Arg Asp Val Asp Tyr Ile Val Arg
                435                 440                 445

Asn Asp Gln Ile Val Ile Ile Asp Glu His Thr Gly Arg Pro Gln Pro
450                 455                 460

Gly Arg Arg Phe Ser Glu Gly Leu His Gln Ala Ile Glu Ala Lys Glu
465                 470                 475                 480

His Val Thr Ile Arg Lys Glu Ser Gln Thr Phe Ala Thr Val Thr Leu
                485                 490                 495

Gln Asn Phe Phe Arg Leu Tyr Glu Lys Leu Ala Gly Met Thr Gly Thr
                500                 505                 510

Ala Ile Thr Glu Ser Lys Glu Phe Lys Glu Ile Tyr Asn Leu Tyr Val
                515                 520                 525

Leu Gln Val Pro Thr Phe Lys Glu Cys Leu Arg Val Asp His Asn Asp
                530                 535                 540

Glu Phe Tyr Met Thr Glu Arg Glu Lys Tyr His Ala Ile Val Lys Glu
545                 550                 555                 560
```

Ile Ala Arg Ile His Ala Val Gly Asn Pro Ile Leu Ile Gly Thr Glu
             565                 570                 575

Ser Val Glu Val Ser Glu Lys Leu Ser Arg Ile Leu Arg Gln Asn Arg
        580                 585                 590

Ile Glu His Thr Val Leu Asn Ala Lys Asn His Ala Gln Glu Ala Glu
    595                 600                 605

Ile Ile Ala Ala Ala Gly Lys Leu Gly Ala Val Thr Val Ala Thr Asn
610                 615                 620

Met Ala Gly Arg Gly Thr Asp Ile Lys Leu Asp Glu Glu Ala Val Val
625                 630                 635                 640

Val Gly Gly Leu His Val Ile Gly Thr Ser Arg His Gln Ser Arg Arg
                645                 650                 655

Ile Asp Arg Gln Leu Arg Gly Arg Cys Ala Arg Leu Gly Asp Pro Gly
            660                 665                 670

Ser Ala Lys Phe Phe Leu Ser Phe Glu Asp Arg Leu Met Arg Leu Phe
        675                 680                 685

Ala Ser Pro Lys Leu Asn Ala Leu Ile Arg His Phe Arg Pro Pro Glu
    690                 695                 700

Gly Glu Ala Met Ser Asp Pro Met Phe Asn Lys Leu Ile Glu Thr Ala
705                 710                 715                 720

Gln Lys Arg Val Glu Ala Arg Asn Tyr Thr Ile Arg Lys His Thr Leu
                725                 730                 735

Glu Tyr Asp Asp Val Met Asn Arg Gln Arg Gln Thr Ile Tyr Ala Phe
            740                 745                 750

Arg Asn Asp Val Ile Arg Ser Asp Ile Phe Gly Leu Ala Lys Glu
        755                 760                 765

Ala Ile Ser His Val Ala Leu Met Ile Ala Ser Leu Ile Val Ser Arg
    770                 775                 780

Asp His Pro Thr Gly Asn Ser Leu Pro Arg Leu Glu Glu Trp Met Asn
785                 790                 795                 800

Tyr Ser Phe Pro Leu Gln Leu Asn Ile Glu Glu Leu Lys Arg Leu Lys
                805                 810                 815

Ser Ile Asp Ala Ile Ala Glu Arg Val Ala Asp Asp Leu Ile Glu Val
            820                 825                 830

Phe Gln Asn Lys Phe Ala Ser Met Val Gln Glu Ile Thr Glu Ala Ala
        835                 840                 845

Gly Glu Lys Val Asp Ala Asn Gly Val Cys Lys Asp Val Ile Arg Ser
    850                 855                 860

Val Met Ile Met His Ile Asp Glu Gln Trp Lys Ile His Leu Val Asp
865                 870                 875                 880

Met Asp Leu Leu Arg Ser Glu Val Gly Leu Arg Thr Val Gly Gln Lys
                885                 890                 895

Asp Pro Leu Ile Glu Phe Lys His Glu Ser Phe Leu Leu Phe Glu Ser
            900                 905                 910

Leu Ile Arg Asp Ile Arg Ile Ala Ile Val Lys His Leu Phe Arg Leu
        915                 920                 925

Glu Leu Thr Met Thr Arg Glu Gln Arg Pro Gln Asn Val Val Pro Val
    930                 935                 940

Val Ala Thr Ser Phe Gln Asn Asn Glu Asn Phe Gly Pro Leu Glu Leu
945                 950                 955                 960

Thr Val Ile Ser Asp Ser Asp Asp Glu
                965

<210> SEQ ID NO 34

<211> LENGTH: 577
<212> TYPE: DNA
<213> ORGANISM: Chlamydia psittaci

<400> SEQUENCE: 34

```
gttgatgctg cagttattcc agggaacttc gccattgcag ggggaatctg tccgtataaa     60
aacagtctat acctagaaga tgtccgtact tcccaataca ccaatgtcgt tgtcatacgt    120
gctgaagata tggaagactc gagaatgcat aaactaaaac agctattgca aagcagttct    180
gtgcaggatt tctttaatac gaaatataag gggatctttt tatcgcagta acacatctgg    240
atggcttagg gaagagttga gccaccccgt tctccgtagg tttaaggcat attgggaaac    300
gattttcttg aattttttga aaaactttga ctgtttttct tttgattatt cgaagcagat    360
gtatgtcgag tatggcggtt ttagggccca gaggtccttt cagttctcct tttacatgtt    420
ctctataccc aacccaccta aaaatgcact tgctaggttc cattcctata gttggcatat    480
acattggagc gaagcggata gccgccgttg ctcaatatca tagaatgtgt agagcgaata    540
caggagtgtc tcaggtgatt attcaggatt caggatt                             577
```

<210> SEQ ID NO 35
<211> LENGTH: 76
<212> TYPE: PRT
<213> ORGANISM: Chlamydia psittaci

<400> SEQUENCE: 35

```
Val Asp Ala Ala Val Ile Pro Gly Asn Phe Ala Ile Ala Gly Gly Ile
1               5                   10                  15

Cys Pro Tyr Lys Asn Ser Leu Tyr Leu Glu Asp Val Arg Thr Ser Gln
            20                  25                  30

Tyr Thr Asn Val Val Val Ile Arg Ala Glu Asp Met Glu Asp Ser Arg
        35                  40                  45

Met His Lys Leu Lys Gln Leu Leu Gln Ser Ser Ser Val Gln Asp Phe
    50                  55                  60

Phe Asn Thr Lys Tyr Lys Gly Ile Phe Leu Ser Gln
65                  70                  75
```

<210> SEQ ID NO 36
<211> LENGTH: 804
<212> TYPE: DNA
<213> ORGANISM: Chlamydia psittaci

<400> SEQUENCE: 36

```
atgaaaaaaa tcacaatact ctcgttactt gctttagcca tctctttaac aggttgttgc     60
aagaattcag aaggagtctt gcggattgcg gcgagtccca cgccacatgc agagcttctt    120
tatagtttag aaaaggaggc tcaatccctt ggattgcaat tgaaaatact tcccatagat    180
gattaccgtg tacctaaccg tttgctttta gataagcaaa tagaggcaaa ttatttccaa    240
catgaagatt tcttaaaaga tgagtgtgct cggtaccaat gcgaaggaaa acttgcgatt    300
ttggctaagg tacatttaga acctatgggt ttatattcta ataaaaccca gtctctcgaa    360
gagcttaaag tcaaggaaca gctacgtata gcggttccta tagatagaac aaacgaacaa    420
cgtgcgctag acttattgcg agactgcaat ttgattagtt acaaagaagc ttctcatcta    480
gatatcaccg caaaagatgt ctttggttgt ggagggaaaa aggtaacgat tatagagatg    540
gcagcacctt tattagtatc ttctttacca gacgttgatg ctgcagttat tccagggaac    600
ttcgccattg caggggggaat ctgtccgtat aaaaacagtc tatacctaga agatgtccgt    660
acttcccaat acaccaatgt cgttgtcata cgtgctgaag atatggaaga ctcgagaatg    720
```

```
cataaactaa aacagctatt gcaaagcagt tctgtgcagg atttctttaa tacgaaatat      780 aagggatct ttttatcgca gtaa                                             804
```

<210> SEQ ID NO 37
<211> LENGTH: 267
<212> TYPE: PRT
<213> ORGANISM: Chlamydia psittaci

<400> SEQUENCE: 37

```
Met Lys Lys Ile Thr Ile Leu Ser Leu Leu Ala Leu Ala Ile Ser Leu
1               5                   10                  15

Thr Gly Cys Cys Lys Asn Ser Glu Gly Val Leu Arg Ile Ala Ala Ser
            20                  25                  30

Pro Thr Pro His Ala Glu Leu Leu Tyr Ser Leu Glu Lys Glu Ala Gln
        35                  40                  45

Ser Leu Gly Leu Gln Leu Lys Ile Leu Pro Ile Asp Asp Tyr Arg Val
    50                  55                  60

Pro Asn Arg Leu Leu Leu Asp Lys Gln Ile Glu Ala Asn Tyr Phe Gln
65                  70                  75                  80

His Glu Asp Phe Leu Lys Asp Glu Cys Ala Arg Tyr Gln Cys Glu Gly
                85                  90                  95

Lys Leu Ala Ile Leu Ala Lys Val His Leu Glu Pro Met Gly Leu Tyr
            100                 105                 110

Ser Asn Lys Thr Gln Ser Leu Glu Glu Leu Lys Val Lys Glu Gln Leu
        115                 120                 125

Arg Ile Ala Val Pro Ile Asp Arg Thr Asn Glu Gln Arg Ala Leu Asp
    130                 135                 140

Leu Leu Arg Asp Cys Asn Leu Ile Ser Tyr Lys Glu Ala Ser His Leu
145                 150                 155                 160

Asp Ile Thr Ala Lys Asp Val Phe Gly Cys Gly Gly Lys Lys Val Thr
                165                 170                 175

Ile Ile Glu Met Ala Ala Pro Leu Leu Val Ser Ser Leu Pro Asp Val
            180                 185                 190

Asp Ala Ala Val Ile Pro Gly Asn Phe Ala Ile Ala Gly Gly Ile Cys
        195                 200                 205

Pro Tyr Lys Asn Ser Leu Tyr Leu Glu Asp Val Arg Thr Ser Gln Tyr
    210                 215                 220

Thr Asn Val Val Val Ile Arg Ala Glu Asp Met Glu Asp Ser Arg Met
225                 230                 235                 240

His Lys Leu Lys Gln Leu Leu Gln Ser Ser Val Gln Asp Phe Phe
                245                 250                 255

Asn Thr Lys Tyr Lys Gly Ile Phe Leu Ser Gln
            260                 265
```

<210> SEQ ID NO 38
<211> LENGTH: 402
<212> TYPE: DNA
<213> ORGANISM: Chlamydia psittaci

<400> SEQUENCE: 38

```
catgtatttt acgcaaaaaa taaacggtat aactcctgct tacaagccgc gctataccac      60
aataatatcc cgacaaccgt gtacacaaac cttattgata tcgtgaagaa aaattcttca     120
ctaatcacga agtactttc catcaaacaa cgatgcttaa atctaaaaga tttccatttt     180
tatgatgttt atgctcccct aagtcagtcc aaagagaaaa aatatacgtt ccaagaagct     240
```

```
gtggatctta tctatactag cctttctcct ctaggaacgg aatacattga taccttaaaa      300 cagggggttaa caactcaagg ctgggtagat aaatacgaaa atcttaataa acgctccgga    360
gcctattctt cgggatgtta cgatagccac ccttatgtcc tc                        402
```

<210> SEQ ID NO 39
<211> LENGTH: 134
<212> TYPE: PRT
<213> ORGANISM: Chlamydia psittaci

<400> SEQUENCE: 39

```
His Val Phe Tyr Ala Lys Asn Lys Arg Tyr Asn Ser Cys Leu Gln Ala
1               5                   10                  15

Ala Leu Tyr His Asn Asn Ile Pro Thr Thr Val Tyr Thr Asn Leu Ile
            20                  25                  30

Asp Ile Val Lys Lys Asn Ser Ser Leu Ile Thr Lys Tyr Phe Ser Ile
        35                  40                  45

Lys Gln Arg Cys Leu Asn Leu Lys Asp Phe His Phe Tyr Asp Val Tyr
    50                  55                  60

Ala Pro Leu Ser Gln Ser Lys Glu Lys Lys Tyr Thr Phe Gln Glu Ala
65                  70                  75                  80

Val Asp Leu Ile Tyr Thr Ser Leu Ser Pro Leu Gly Thr Glu Tyr Ile
                85                  90                  95

Asp Thr Leu Lys Gln Gly Leu Thr Thr Gln Gly Trp Val Asp Lys Tyr
            100                 105                 110

Glu Asn Leu Asn Lys Arg Ser Gly Ala Tyr Ser Ser Gly Cys Tyr Asp
        115                 120                 125

Ser His Pro Tyr Val Leu
    130
```

<210> SEQ ID NO 40
<211> LENGTH: 1827
<212> TYPE: DNA
<213> ORGANISM: Chlamydia psittaci

<400> SEQUENCE: 40

```
atgagcgtag aattcaacaa gcaacaagtc cgtccaagaa gtgaaatttc ccctcaagat      60
tgttgggata tcacccccctt atatctaaat agaaaagcat ggaaagcaga tcttgattct    120
ttcggattaa aaacagacgg ctcacctacg tggcccgctc ttcaagcaac gcaataccaa    180
ctggacaact cagaatctct actatcctta ttaactactc tcttctctat tgagagaaaa    240
ttaaacaaac tctacgttta cgctcatctg actcatgatc aggatattac aaatcaagaa    300
ggcatcgcag atcttaaatc tatcacgcat ctacataccct atttgccga agaaaccctct   360 tgggtacaac ccgctttaac cagcctatcg gaatctctca ttgctcagca cctatcagct   420
ccctgtttag ctccttatag attctatttta gagaaaatct ttagactatc tatacacaca   480
ggcactcctg gagaagaaaa aattctcgct tccgccttta ctcctcttga gtagccagt    540 aaggcatttt cttcttaag tgactctgaa attcccttttg gcaagctac agactcagaa   600 ggaaactctc acccgctttc tcatgcactg gcttcattgt atatgcaatc cacagatcgg   660
gaattacgaa aaacatccta cctagcacaca tgtgaaagat atcatagtta ccgacatacc   720
tttgctaact tactcaatgg gaaaatccaa gcccatgtat tttacgcaaa aaataaacgg    780
tataactcct gcttacaagc cgcgctatac acaataata tcccgacaac cgtgtacaca   840
aaccttattg atatcgtgaa gaaaaattct tcactaatca cgaagtactt ttccatcaaa    900
caacgatgct taaatctaaa agattttccat tttatgatg tttatgctcc cctaagtcag   960
```

```
tccaaagaga aaaaatatac gttccaagaa gctgtggatc ttatctatac tagcctttct   1020
cctctaggaa cggaatacat tgatacctta aaacaggggt taacaactca aggctgggta   1080
gataaatacg aaaatcttaa taaacgctcc ggagcctatt cttcgggatg ttacgatagc   1140
cacccttatg tcctcctaaa ctatacaggc accctgtatg atgtatccgt cattgcccac   1200
gaaggcggac acagtatgca ctcgtatttt agtaggaagc atcaaccttt ccatgacgct   1260
caatatccta ttttccttgc tgaaattgct tctaccttaa atgaaatgct tcttatggat   1320
tccatgctga aggagagcga ctcaaaagaa gagaaaatca ccattctgac acgatgtttg   1380
gataccatct tctctacact attccgtcag gtattattcg cctcttttga atacgatatt   1440
catcacgcag cagaacatgg ggttcctcta actgaagaat acctatcctc aacttacaag   1500
aatttacaaa atgagtttta cggagaaatt atcacatttg atgtcctgtc gaacatagaa   1560
tgggcaagaa ttcctcattt ctattacaat ttctacgtat accaatatgc aacgggcatt   1620
atagccgccc tgtgcttttt agaaaaaatt cttaacaacg aagataacgc tcttaactcc   1680
tatctcaact tttaaaaag tggtggatca gatttcccct tagaaatctt aaaaaaatca   1740
ggattagata tgggcacagt tgagccaatc caaaaagctt tttgctttat cgagaaaaaa   1800
atccaggagc tatcatcttt aatttga                                        1827
```

```
<210> SEQ ID NO 41
<211> LENGTH: 608
<212> TYPE: PRT
<213> ORGANISM: Chlamydia psittaci

<400> SEQUENCE: 41

Met Ser Val Glu Phe Asn Lys Gln Gln Val Arg Pro Arg Ser Glu Ile
1               5                   10                  15

Ser Pro Gln Asp Cys Trp Asp Ile Thr Pro Leu Tyr Leu Asn Arg Lys
            20                  25                  30

Ala Trp Lys Ala Asp Leu Asp Ser Phe Gly Leu Lys Thr Asp Gly Ser
        35                  40                  45

Pro Thr Trp Pro Ala Leu Gln Ala Thr Gln Tyr Gln Leu Asp Asn Ser
    50                  55                  60

Glu Ser Leu Leu Ser Leu Leu Thr Thr Leu Phe Ser Ile Glu Arg Lys
65                  70                  75                  80

Leu Asn Lys Leu Tyr Val Tyr Ala His Leu Thr His Asp Gln Asp Ile
                85                  90                  95

Thr Asn Gln Glu Gly Ile Ala Asp Leu Lys Ser Ile Thr His Leu His
            100                 105                 110

Thr Leu Phe Ala Glu Glu Thr Ser Trp Val Gln Pro Ala Leu Thr Ser
        115                 120                 125

Leu Ser Glu Ser Leu Ile Ala Gln His Leu Ser Ala Pro Cys Leu Ala
    130                 135                 140

Pro Tyr Arg Phe Tyr Leu Glu Lys Ile Phe Arg Leu Ser Ile His Thr
145                 150                 155                 160

Gly Thr Pro Gly Glu Glu Lys Ile Leu Ala Ser Ala Phe Thr Pro Leu
                165                 170                 175

Glu Val Ala Ser Lys Ala Phe Ser Ser Leu Ser Asp Ser Glu Ile Pro
            180                 185                 190

Phe Gly Gln Ala Thr Asp Ser Glu Gly Asn Ser His Pro Leu Ser His
        195                 200                 205

Ala Leu Ala Ser Leu Tyr Met Gln Ser Thr Asp Arg Glu Leu Arg Lys
    210                 215                 220
```

Thr Ser Tyr Leu Ala Gln Cys Glu Arg Tyr His Ser Tyr Arg His Thr
225                 230                 235                 240

Phe Ala Asn Leu Leu Asn Gly Lys Ile Gln Ala His Val Phe Tyr Ala
            245                 250                 255

Lys Asn Lys Arg Tyr Asn Ser Cys Leu Gln Ala Ala Leu Tyr His Asn
        260                 265                 270

Asn Ile Pro Thr Thr Val Tyr Thr Asn Leu Ile Asp Ile Val Lys Lys
    275                 280                 285

Asn Ser Ser Leu Ile Thr Lys Tyr Phe Ser Ile Lys Gln Arg Cys Leu
290                 295                 300

Asn Leu Lys Asp Phe His Phe Tyr Asp Val Tyr Ala Pro Leu Ser Gln
305                 310                 315                 320

Ser Lys Glu Lys Lys Tyr Thr Phe Gln Glu Ala Val Asp Leu Ile Tyr
            325                 330                 335

Thr Ser Leu Ser Pro Leu Gly Thr Glu Tyr Ile Asp Thr Leu Lys Gln
        340                 345                 350

Gly Leu Thr Thr Gln Gly Trp Val Asp Lys Tyr Glu Asn Leu Asn Lys
    355                 360                 365

Arg Ser Gly Ala Tyr Ser Ser Gly Cys Tyr Asp Ser His Pro Tyr Val
370                 375                 380

Leu Leu Asn Tyr Thr Gly Thr Leu Tyr Asp Val Ser Val Ile Ala His
385                 390                 395                 400

Glu Gly Gly His Ser Met His Ser Tyr Phe Ser Arg Lys His Gln Pro
            405                 410                 415

Phe His Asp Ala Gln Tyr Pro Ile Phe Leu Ala Glu Ile Ala Ser Thr
        420                 425                 430

Leu Asn Glu Met Leu Leu Met Asp Ser Met Leu Lys Glu Ser Asp Ser
    435                 440                 445

Lys Glu Glu Lys Ile Thr Ile Leu Thr Arg Cys Leu Asp Thr Ile Phe
450                 455                 460

Ser Thr Leu Phe Arg Gln Val Leu Phe Ala Ser Phe Glu Tyr Asp Ile
465                 470                 475                 480

His His Ala Ala Glu His Gly Val Pro Leu Thr Glu Glu Tyr Leu Ser
            485                 490                 495

Ser Thr Tyr Lys Asn Leu Gln Asn Glu Phe Tyr Gly Leu Ile Ile Thr
        500                 505                 510

Phe Asp Val Leu Ser Asn Ile Glu Trp Ala Arg Ile Pro His Phe Tyr
    515                 520                 525

Tyr Asn Phe Tyr Val Tyr Gln Tyr Ala Thr Gly Ile Ile Ala Ala Leu
530                 535                 540

Cys Phe Leu Glu Lys Ile Leu Asn Asn Glu Asp Asn Ala Leu Asn Ser
545                 550                 555                 560

Tyr Leu Asn Phe Leu Lys Ser Gly Gly Ser Asp Phe Pro Leu Glu Ile
            565                 570                 575

Leu Lys Lys Ser Gly Leu Asp Met Gly Thr Val Glu Pro Ile Gln Lys
        580                 585                 590

Ala Phe Cys Phe Ile Glu Lys Lys Ile Gln Glu Leu Ser Ser Leu Ile
    595                 600                 605

<210> SEQ ID NO 42
<211> LENGTH: 1517
<212> TYPE: DNA
<213> ORGANISM: Chlamydia psittaci

<400> SEQUENCE: 42

```
gcgttagatt cggaagagct gaaagagcaa ataaacaatc taaaagagcg tttatgggat    60
gcacaatcca ctctacaaca agatcaaaat aaactatcgc aagaacattt tgaagctgtc   120
agtgtgatca ttgatttaat caatggtgat ctgaatgata tagctgagca tacgcaacaa   180
aacttacaaa ccaaaaaaga agaagaacac gagtccgttg cccgtaagat ggtcaattgg   240
gtgtcttctg gagaagaagt gttaaataga gcccttctct acttctcaga taggaatgga   300
gaacgggaaa atttagcaga cttttaaaa gtacagtatg ctgttcaaag agcaacgcaa   360
agagcagaac tttttgctag tatcgtagga actacggtaa gtagtataaa gacgataatg   420
accacacaat taggttaaca tggacgaatt gacgacagat ttcgataccc tcatgtcgca   480
attgaacgac gtacacttga ctaccgttgt cggtcgtata actgaagtcg tcggtatgtt   540
aattaaagct gtcgttccca atgtacgcgt tggggaggta tgcttagtta aacgttatgg   600
tatggagccg ctcgtgaccg aagtcgtcgg cttcacacaa aatttcgctt ttttatcgcc   660
actaggagaa cttactggag tcagcccttc ttcagaggtt attcccacag gtctgccttt   720
gtatatccgt gcaggtaacg gtcttttagg tcgtgtattg aatggtctgg gagaacctat   780
cgactccgag atcaaaggac ctttggttga tgttaacgaa acctaccctg tgtttcgcgc   840
tccaccagat ccattgcata gagaaaaatt aagaacaatt ttatccaccg gcgtgcggtg   900
tatcgacggt atgctcacag tcgccagagg ccagcgtata ggcattttg ctggagctgg   960
ggtgggtaaa tcgtctctct tgggaatgat cgctagaaac gcggaagaag ccgatgtcaa  1020
tgtgattgct ctcatcggag agcggggccg agaggttcgt gaatttatcg agggcgatct  1080
cggagaagaa ggaatgaaac gttcggtgat cgtcgtctct acttcagatc aatcctcaca  1140
gttgcgatta aatgctgctt acgtaggcac cgctatagca gagtattttc gtgatcaggg  1200
caaaaccgta gttttgatga tggattctgt cacccgattt gcccgagccc taagagaagt  1260
cggtctagct gccggagaac cgccagctcg aggaggatac acaccttctg tattctcaac  1320
tttgcctagg ttattagaac gttccggagc ttcggataaa ggaacaatca cagccttta  1380
cacagtactt gttgccgggg atgatatgaa tgaaccggtc gctgatgaag ttaaatcgat  1440
tcttgatggt cacgttgtct tgtctaacgc tttagctcag gcataccatt atcctgctat  1500
tgatgtctta gcatcta                                                  1517
```

<210> SEQ ID NO 43
<211> LENGTH: 145
<212> TYPE: PRT
<213> ORGANISM: Chlamydia psittaci

<400> SEQUENCE: 43

```
Ala Leu Asp Ser Glu Glu Leu Lys Glu Gln Ile Asn Asn Leu Lys Glu
1               5                   10                  15

Arg Leu Trp Asp Ala Gln Ser Thr Leu Gln Gln Asp Gln Asn Lys Leu
            20                  25                  30

Ser Gln Glu His Phe Glu Ala Val Ser Val Ile Ile Asp Leu Ile Asn
        35                  40                  45

Gly Asp Leu Asn Asp Ile Ala Glu His Thr Gln Gln Asn Leu Gln Thr
    50                  55                  60

Lys Lys Glu Glu Glu His Glu Ser Val Ala Arg Lys Met Val Asn Trp
65                  70                  75                  80

Val Ser Ser Gly Glu Glu Val Leu Asn Arg Ala Leu Leu Tyr Phe Ser
                85                  90                  95

Asp Arg Asn Gly Glu Arg Glu Asn Leu Ala Asp Phe Leu Lys Val Gln
```

-continued

```
                   100                 105                 110
Tyr Ala Val Gln Arg Ala Thr Gln Arg Ala Glu Leu Phe Ala Ser Ile
            115                 120                 125
Val Gly Thr Thr Val Ser Ser Ile Lys Thr Ile Met Thr Thr Gln Leu
    130                 135                 140
Gly
145

<210> SEQ ID NO 44
<211> LENGTH: 669
<212> TYPE: DNA
<213> ORGANISM: Chlamydia psittaci

<400> SEQUENCE: 44
atggtagatc ctttgaagct tttcccaaag ctagactccg agaaagaaac agcttctata    60
cagaagcctt taggaactcc tttagccagt gagttacata ggaagttcc tgcattttct    120 ttagggacgg cagcagactc cttgaataaa aatatagagg atgtcaagcc taaccctatg    180
gcgatgatgc aagacagaaa ctctaacatt atcgatcctg aactggaaga ggcgttagat    240
tcggaagagc tgaaagagca aataaacaat ctaaaagagc gtttatggga tgcacaatcc    300
actctacaac aagatcaaaa taaactatcg caagaacatt ttgaagctgt cagtgtgatc    360
attgatttaa tcaatggtga tctgaatgat atagctgagc atacgcaaca aaacttacaa    420
accaaaaaag aagaagaaca cgagtccgtt gcccgtaaga tggtcaattg ggtgtcttct    480
ggagaagaag tgttaaatag agcccttctc tacttctcag ataggaatgg agaacgggaa    540
aatttagcag acttttttaaa agtacagtat gctgttcaaa gagcaacgca aagagcagaa    600 cttttttgcta gtatcgtagg aactacggta agtagtataa agacgataat gaccacacaa    660
ttaggttaa                                                            669

<210> SEQ ID NO 45
<211> LENGTH: 222
<212> TYPE: PRT
<213> ORGANISM: Chlamydia psittaci

<400> SEQUENCE: 45

Met Val Asp Pro Leu Lys Leu Phe Pro Lys Leu Asp Ser Glu Lys Glu
1               5                   10                  15

Thr Ala Ser Ile Gln Lys Pro Leu Gly Thr Pro Leu Ala Ser Glu Leu
            20                  25                  30

His Lys Glu Val Pro Ala Phe Ser Leu Gly Thr Ala Ala Asp Ser Leu
        35                  40                  45

Asn Lys Asn Ile Glu Asp Val Lys Pro Asn Pro Met Ala Met Met Gln
    50                  55                  60

Asp Arg Asn Ser Asn Ile Ile Asp Pro Glu Leu Glu Glu Ala Leu Asp
65                  70                  75                  80

Ser Glu Glu Leu Lys Glu Gln Ile Asn Asn Leu Lys Glu Arg Leu Trp
                85                  90                  95

Asp Ala Gln Ser Thr Leu Gln Gln Asp Gln Asn Lys Leu Ser Gln Glu
            100                 105                 110

His Phe Glu Ala Val Ser Val Ile Ile Asp Leu Ile Asn Gly Asp Leu
        115                 120                 125

Asn Asp Ile Ala Glu His Thr Gln Gln Asn Leu Gln Thr Lys Lys Glu
    130                 135                 140

Glu Glu His Glu Ser Val Ala Arg Lys Met Val Asn Trp Val Ser Ser
145                 150                 155                 160
```

Gly Glu Glu Val Leu Asn Arg Ala Leu Leu Tyr Phe Ser Asp Arg Asn
            165                 170                 175

Gly Glu Arg Glu Asn Leu Ala Asp Phe Leu Lys Val Gln Tyr Ala Val
            180                 185                 190

Gln Arg Ala Thr Gln Arg Ala Glu Leu Phe Ala Ser Ile Val Gly Thr
            195                 200                 205

Thr Val Ser Ser Ile Lys Thr Ile Met Thr Thr Gln Leu Gly
            210                 215                 220

<210> SEQ ID NO 46
<211> LENGTH: 1329
<212> TYPE: DNA
<213> ORGANISM: Chlamydia psittaci

<400> SEQUENCE: 46

| | | | | | | |
|---|---|---|---|---|---|---|
| atggacgaat | tgacgacaga | tttcgatacc | ctcatgtcgc | aattgaacga | cgtacacttg | 60 |
| actaccgttg | tcggtcgtat | aactgaagtc | gtcggtatgt | taattaaagc | tgtcgttccc | 120 |
| aatgtacgcg | ttggggaggt | atgcttagtt | aaacgttatg | gtatggagcc | gctcgtgacc | 180 |
| gaagtcgtcg | gcttcacaca | aaatttcgct | tttttatcgc | cactaggaga | acttactgga | 240 |
| gtcagccctt | cttcagaggt | tattcccaca | ggtctgcctt | tgtatatccg | tgcaggtaac | 300 |
| ggtcttttag | tcgtgtatt | gaatggtctg | ggagaaccta | tcgactccga | gatcaaagga | 360 |
| cctttggttg | atgttaacga | aacctaccct | gtgtttcgcg | ctccaccaga | tccattgcat | 420 |
| agagaaaaat | taagaacaat | tttatccacc | ggcgtgcggt | tatcgacgg | tatgctcaca | 480 |
| gtcgccagag | gccagcgtat | aggcattttt | gctggagctg | gggtgggtaa | atcgtctctc | 540 |
| ttgggaatga | tcgctagaaa | cgcggaagaa | gccgatgtca | atgtgattgc | tctcatcgga | 600 |
| gagcggggcc | gagaggttcg | tgaatttatc | gagggcgatc | tcggagaaga | aggaatgaaa | 660 |
| cgttcggtga | tcgtcgtctc | tacttcagat | caatcctcac | agttgcgatt | aaatgctgct | 720 |
| tacgtaggca | ccgctatagc | agagtatttt | cgtgatcagg | gcaaaaccgt | agttttgatg | 780 |
| atggattctg | tcacccgatt | tgcccgagcc | taagagaag | tcggtctagc | tgccggagaa | 840 |
| ccgccagctc | gaggaggata | cacaccttct | gtattctcaa | ctttgcctag | ttattagaa | 900 |
| cgttccggag | cttcggataa | aggaacaatc | acagcctttt | acacagtact | tgttgccggg | 960 |
| gatgatatga | atgaaccggt | cgctgatgaa | gttaaatcga | ttcttgatgg | tcacgttgtc | 1020 |
| ttgtctaacg | ctttagctca | ggcataccat | tatcctgcta | ttgatgtctt | agcatctatc | 1080 |
| agccgattgc | tgacagcaat | tgttcctgag | gaacaacgac | gcatcatagg | aaaagcccga | 1140 |
| gaggtgctgg | caaaatacaa | agcaaacgaa | atgcttatac | gtattggaga | atatcgccga | 1200 |
| gggtccgatc | gtgaagtgga | ttttgctata | gatcacattg | ataaattgaa | cagattctta | 1260 |
| aagcaagata | ttcatgaaaa | aacaaattac | gaggaagcct | cgcaacagct | tcgggctatt | 1320 |
| ttccgataa | | | | | | 1329 |

<210> SEQ ID NO 47
<211> LENGTH: 442
<212> TYPE: PRT
<213> ORGANISM: Chlamydia psittaci

<400> SEQUENCE: 47

Met Asp Glu Leu Thr Thr Asp Phe Asp Thr Leu Met Ser Gln Leu Asn
1               5                   10                  15

Asp Val His Leu Thr Thr Val Val Gly Arg Ile Thr Glu Val Val Gly
            20                  25                  30

```
Met Leu Ile Lys Ala Val Val Pro Asn Val Arg Val Gly Glu Val Cys
             35                  40                  45
Leu Val Lys Arg Tyr Gly Met Glu Pro Leu Val Thr Glu Val Val Gly
 50                  55                  60
Phe Thr Gln Asn Phe Ala Phe Leu Ser Pro Leu Gly Glu Leu Thr Gly
 65                  70                  75                  80
Val Ser Pro Ser Ser Glu Val Ile Pro Thr Gly Leu Pro Leu Tyr Ile
                 85                  90                  95
Arg Ala Gly Asn Gly Leu Leu Gly Arg Val Leu Asn Gly Leu Gly Glu
                100                 105                 110
Pro Ile Asp Ser Glu Ile Lys Gly Pro Leu Val Asp Val Asn Glu Thr
                115                 120                 125
Tyr Pro Val Phe Arg Ala Pro Asp Pro Leu His Arg Glu Lys Leu
                130                 135                 140
Arg Thr Ile Leu Ser Thr Gly Val Arg Cys Ile Asp Gly Met Leu Thr
145                 150                 155                 160
Val Ala Arg Gly Gln Arg Ile Gly Ile Phe Ala Gly Ala Gly Val Gly
                165                 170                 175
Lys Ser Ser Leu Leu Gly Met Ile Ala Arg Asn Ala Glu Glu Ala Asp
                180                 185                 190
Val Asn Val Ile Ala Leu Ile Gly Glu Arg Gly Arg Glu Val Arg Glu
                195                 200                 205
Phe Ile Glu Gly Asp Leu Gly Glu Glu Gly Met Lys Arg Ser Val Ile
                210                 215                 220
Val Val Ser Thr Ser Asp Gln Ser Ser Gln Leu Arg Leu Asn Ala Ala
225                 230                 235                 240
Tyr Val Gly Thr Ala Ile Ala Glu Tyr Phe Arg Asp Gln Gly Lys Thr
                245                 250                 255
Val Val Leu Met Met Asp Ser Val Thr Arg Phe Ala Arg Ala Leu Arg
                260                 265                 270
Glu Val Gly Leu Ala Ala Gly Glu Pro Pro Ala Arg Gly Gly Tyr Thr
                275                 280                 285
Pro Ser Val Phe Ser Thr Leu Pro Arg Leu Leu Glu Arg Ser Gly Ala
                290                 295                 300
Ser Asp Lys Gly Thr Ile Thr Ala Phe Tyr Thr Val Leu Val Ala Gly
305                 310                 315                 320
Asp Asp Met Asn Glu Pro Val Ala Asp Val Lys Ser Ile Leu Asp
                325                 330                 335
Gly His Val Val Leu Ser Asn Ala Leu Ala Gln Ala Tyr His Tyr Pro
                340                 345                 350
Ala Ile Asp Val Leu Ala Ser Ile Ser Arg Leu Leu Thr Ala Ile Val
                355                 360                 365
Pro Glu Glu Gln Arg Arg Ile Ile Gly Lys Ala Arg Glu Val Leu Ala
                370                 375                 380
Lys Tyr Lys Ala Asn Glu Met Leu Ile Arg Ile Gly Glu Tyr Arg Arg
385                 390                 395                 400
Gly Ser Asp Arg Glu Val Asp Phe Ala Ile Asp His Ile Asp Lys Leu
                        405                 410                 415
Asn Arg Phe Leu Lys Gln Asp Ile His Glu Lys Thr Asn Tyr Glu Glu
                420                 425                 430
Ala Ser Gln Gln Leu Arg Ala Ile Phe Arg
                435                 440
```

<210> SEQ ID NO 48
<211> LENGTH: 477
<212> TYPE: DNA
<213> ORGANISM: Chlamydia psittaci

<400> SEQUENCE: 48
cttcttgcag atgccgactc tgtcaacctt gcaactggat tcaacggctc cactagtgaa 60
actttcaatg ttaaacaaac agataatgct gacgggacaa catatattct aggcagcgcg 120
atcacctttg aacacataaa tcaattaaaa ccagcaaaca ctagctgttt tgctaataca 180
gctggagatc taacgtttac tgggaatcga cgacttctct atttcaataa tatttcatca 240
acagcgaaag gtgccgctat cagcacaact gcggatggta agacactcac aatatccggg 300
gctctacaac tgattttcta catgtcgcca agattggcca cgggaaatgg cgtcatttat 360
tctaatagct ctgtactcat cgagaacaat tctcaaggta gctcgggact gaataagtct 420
gcagggaaag gcgtctttat ttgttgtgag aaaagtacgg atgtgggagc tacatca 477

<210> SEQ ID NO 49
<211> LENGTH: 159
<212> TYPE: PRT
<213> ORGANISM: Chlamydia psittaci

<400> SEQUENCE: 49

Leu Leu Ala Asp Ala Asp Ser Val Asn Leu Ala Thr Gly Phe Asn Gly
1 5 10 15

Ser Thr Ser Glu Thr Phe Asn Val Lys Gln Thr Asp Asn Ala Asp Gly
20 25 30

Thr Thr Tyr Ile Leu Gly Ser Ala Ile Thr Phe Glu His Ile Asn Gln
35 40 45

Leu Lys Pro Ala Asn Thr Ser Cys Phe Ala Asn Thr Ala Gly Asp Leu
50 55 60

Thr Phe Thr Gly Asn Arg Arg Leu Leu Tyr Phe Asn Asn Ile Ser Ser
65 70 75 80

Thr Ala Lys Gly Ala Ala Ile Ser Thr Thr Ala Asp Gly Lys Thr Leu
85 90 95

Thr Ile Ser Gly Ala Leu Gln Leu Ile Phe Tyr Met Ser Pro Arg Leu
100 105 110

Ala Thr Gly Asn Gly Val Ile Tyr Ser Asn Ser Ser Val Leu Ile Glu
115 120 125

Asn Asn Ser Gln Gly Ser Ser Gly Leu Asn Lys Ser Ala Gly Lys Gly
130 135 140

Val Phe Ile Cys Cys Glu Lys Ser Thr Asp Val Gly Ala Thr Ser
145 150 155

<210> SEQ ID NO 50
<211> LENGTH: 591
<212> TYPE: DNA
<213> ORGANISM: Chlamydia psittaci

<400> SEQUENCE: 50
acctttgaac acataaatca attaaaacca gcaaacacta gctgttttgc taatacagct 60
ggagatctaa cgtttactgg gaatcgacga cttctctatt tcaataatat ttcatcaaca 120
gcgaaaggtg ccgctatcag cacaactgcg gatggtaaga cactcacaat atccggggct 180
ctacaactga ttttctacat gtcgccaaga ttggccacgg gaaatggcgt catttattct 240
aatagctctg tactcatcga gaacaattct caaggtagct cgggactgaa taagtctgca 300
gggaaaggcg tctttatttg ttgtgagaaa agtacggatg tgggagctac atcaccgaca 360

```
ttaatcatac ggaataacgg agagtttctt actgtaggta atgcagctac tagctctgga    420
ggagcgattt atgcggagaa atgatcttta tcctcaggag gatatacaaa atttcaatcc    480
aatgttagct atgatcaagg tggggccatt gccattgctc ctaatggaga aattagtctc    540
tccgcggata aaggaaatat cgtctttgaa agaaacctta  aaattgccaa c           591

<210> SEQ ID NO 51
<211> LENGTH: 197
<212> TYPE: PRT
<213> ORGANISM: Chlamydia psittaci

<400> SEQUENCE: 51

Thr Phe Glu His Ile Asn Gln Leu Lys Pro Ala Asn Thr Ser Cys Phe
1               5                  10                  15

Ala Asn Thr Ala Gly Asp Leu Thr Phe Thr Gly Asn Arg Arg Leu Leu
            20                  25                  30

Tyr Phe Asn Asn Ile Ser Ser Thr Ala Lys Gly Ala Ala Ile Ser Thr
        35                  40                  45

Thr Ala Asp Gly Lys Thr Leu Thr Ile Ser Gly Ala Leu Gln Leu Ile
    50                  55                  60

Phe Tyr Met Ser Pro Arg Leu Ala Thr Gly Asn Gly Val Ile Tyr Ser
65                  70                  75                  80

Asn Ser Ser Val Leu Ile Glu Asn Asn Ser Gln Gly Ser Ser Gly Leu
                85                  90                  95

Asn Lys Ser Ala Gly Lys Gly Val Phe Ile Cys Cys Glu Lys Ser Thr
            100                 105                 110

Asp Val Gly Ala Thr Ser Pro Thr Leu Ile Ile Arg Asn Asn Gly Glu
        115                 120                 125

Phe Leu Thr Val Gly Asn Ala Ala Thr Ser Ser Gly Gly Ala Ile Tyr
    130                 135                 140

Ala Glu Lys Met Ile Leu Ser Ser Gly Gly Tyr Thr Lys Phe Gln Ser
145                 150                 155                 160

Asn Val Ser Tyr Asp Gln Gly Gly Ala Ile Ala Ile Ala Pro Asn Gly
                165                 170                 175

Glu Ile Ser Leu Ser Ala Asp Lys Gly Asn Ile Val Phe Glu Arg Asn
            180                 185                 190

Leu Lys Ile Ala Asn
        195

<210> SEQ ID NO 52
<211> LENGTH: 2040
<212> TYPE: DNA
<213> ORGANISM: Chlamydia psittaci

<400> SEQUENCE: 52 atgcaggggaa tactaatgaa aaactctatt tatgggggttt tactgttttc ctcttttgcc    60
ttatccactg ctaccaaact tcttgcagat gccgactctg tcaaccttgc aactggattc    120
aacggctcca ctagtgaaac tttcaatgtt aaacaaacag ataatgctga cgggacaaca    180
tatattctag gcagcgcgat caccctttgaa cacataaaatc aattaaaacc agcaaacact    240
agctgttttg ctaatacagc tggagatcta acgttactg ggaatcgacg acttctctat    300
ttcaataata tttcatcaac agcgaaaggt gccgctatca gcacaactgc ggatggtaag    360
acactcacaa tatccggggc tctacaactg atttttctaca tgtcgccaag attggccacg    420
ggaaatggcg tcatttattc taatagctct gtactcatcg agaacaattc tcaaggtagc    480
```

-continued

```
tcgggactga ataagtctgc agggaaaggc gtctttattt gttgtgagaa aagtacggat     540
gtgggagcta catcaccgac attaatcata cggaataacg gagagtttct tactgtaggt     600
aatgcagcta ctagctctgg aggagcgatt tatgcggaga aaatgatctt atcctcagga     660
ggatatacaa aatttcaatc caatgttagc tatgatcaag gtggggccat tgccattgct     720
cctaatggag aaattagtct ctccgcggat aaaggaaata tcgtctttga aagaaacctt     780
aaaattgcca acaaacaaaa tactcccaat gccattcacc taggagacaa tgcgaaattt     840
cttcaattac gtgctgctaa caacaaagcc atattttttt atgacccgat tacaaccacg     900
ggatctgtgg cagatcggct aattattaat aactcgcaag gagaagcctc gacttacgat     960
ggggcgattg tattttctag tctcaactta ttcactcatt cccctgaatg taaactctct    1020
tcattttctc aaggtcttac tttagcggca ggatcattag ttttagaaga gggggtatgt    1080
gtacaagctc cgtcttttga tcaacgtgct cactcccaac tattcatgaa tcctgggacg    1140
aagttacaag ctacccagaa catctcggta aagaatctcc atctcaatct taatagaata    1200
gcagaagagc cggcgtatat caccacaaca gacgatgctt ctagtgtgga catttgcgga    1260
cctgtagtta tgcatataga tgatgagatc ttctataatc agacagtatt agcaaatgag    1320
ttgtctgtag agtgtttaaa tctcagttct ccacatctcg ataatatcac tattgatgac    1380
gttcccgcag tgcctatcat gacgttagaa tcgcatcgtg gttatcaagg tacatgggaa    1440
atctcttgga aagagcaacc taaacttacc tttgggaagg cgactatcgc gcctaataag    1500
cagatgcacc ttatttggaa accttctggt tacgttcctt tctcaggggg aactggagag    1560
tttacgacat ctttagtgcc taatagctta tggaatctct ttttagatac acgtttttct    1620
caacaagcga ttgagaaaca tgctgtatct tcaggtaacg gtatatggat ttcctccatg    1680
accaattctt ttcttcaagg ttctacgaac aacaaccacg gctttcgtca taagagttca    1740
ggatataccg caggggggaaa aatacaaaca cttcaagatg atatctttag tgtcagtttt    1800
tctcagctat ttgggagatc taaggatttt ggatctgcca catctaagga tacattccta    1860
tcgggctcta tctatgctca gcattcgaga cgcttacttc ctataatgag attccttgca    1920
ggaacatcaa catatagacc gcgactctta ctgagtattc ccaagaatct tcctatcaat    1980
tttgatgttc ttgtgagtta cagctatgac agtaaccaca tgaaagtaca aaaattctaa    2040
```

<210> SEQ ID NO 53
<211> LENGTH: 679
<212> TYPE: PRT
<213> ORGANISM: Chlamydia psittaci

<400> SEQUENCE: 53

```
Met Gln Gly Ile Leu Met Lys Asn Ser Ile Tyr Gly Val Leu Leu Phe
1               5                   10                  15

Ser Ser Phe Ala Leu Ser Thr Ala Thr Lys Leu Leu Ala Asp Ala Asp
            20                  25                  30

Ser Val Asn Leu Ala Thr Gly Phe Asn Gly Ser Thr Ser Glu Thr Phe
        35                  40                  45

Asn Val Lys Gln Thr Asp Asn Ala Asp Gly Thr Thr Tyr Ile Leu Gly
    50                  55                  60

Ser Ala Ile Thr Phe Glu His Ile Asn Gln Leu Lys Pro Ala Asn Thr
65                  70                  75                  80

Ser Cys Phe Ala Asn Thr Ala Gly Asp Leu Thr Phe Thr Gly Asn Arg
                85                  90                  95

Arg Leu Leu Tyr Phe Asn Asn Ile Ser Ser Thr Ala Lys Gly Ala Ala
            100                 105                 110
```

```
Ile Ser Thr Thr Ala Asp Gly Lys Thr Leu Thr Ile Ser Gly Ala Leu
        115                 120                 125

Gln Leu Ile Phe Tyr Met Ser Pro Arg Leu Ala Thr Gly Asn Gly Val
    130                 135                 140

Ile Tyr Ser Asn Ser Ser Val Leu Ile Glu Asn Ser Gln Gly Ser
145                 150                 155                 160

Ser Gly Leu Asn Lys Ser Ala Gly Lys Gly Val Phe Ile Cys Cys Glu
                165                 170                 175

Lys Ser Thr Asp Val Gly Ala Thr Ser Pro Thr Leu Ile Ile Arg Asn
            180                 185                 190

Asn Gly Glu Phe Leu Thr Val Gly Asn Ala Ala Thr Ser Ser Gly Gly
        195                 200                 205

Ala Ile Tyr Ala Glu Lys Met Ile Leu Ser Ser Gly Gly Tyr Thr Lys
        210                 215                 220

Phe Gln Ser Asn Val Ser Tyr Asp Gln Gly Gly Ala Ile Ala Ile Ala
225                 230                 235                 240

Pro Asn Gly Glu Ile Ser Leu Ser Ala Asp Lys Gly Asn Ile Val Phe
                245                 250                 255

Glu Arg Asn Leu Lys Ile Ala Asn Lys Gln Asn Thr Pro Asn Ala Ile
            260                 265                 270

His Leu Gly Asp Asn Ala Lys Phe Leu Gln Leu Arg Ala Ala Asn Asn
        275                 280                 285

Lys Ala Ile Phe Phe Tyr Asp Pro Ile Thr Thr Thr Gly Ser Val Ala
        290                 295                 300

Asp Arg Leu Ile Ile Asn Asn Ser Gln Gly Glu Ala Ser Thr Tyr Asp
305                 310                 315                 320

Gly Ala Ile Val Phe Ser Ser Leu Asn Leu Phe Thr His Ser Pro Glu
                325                 330                 335

Cys Lys Leu Ser Ser Phe Ser Gln Gly Leu Thr Leu Ala Ala Gly Ser
            340                 345                 350

Leu Val Leu Glu Glu Gly Val Cys Val Gln Ala Pro Ser Phe Asp Gln
        355                 360                 365

Arg Ala His Ser Gln Leu Phe Met Asn Pro Gly Thr Lys Leu Gln Ala
        370                 375                 380

Thr Gln Asn Ile Ser Val Lys Asn Leu His Leu Asn Leu Asn Arg Ile
385                 390                 395                 400

Ala Glu Glu Pro Ala Tyr Ile Thr Thr Thr Asp Asp Ala Ser Ser Val
                405                 410                 415

Asp Ile Cys Gly Pro Val Val Met His Ile Asp Asp Glu Ile Phe Tyr
            420                 425                 430

Asn Gln Thr Val Leu Ala Asn Glu Leu Ser Val Glu Cys Leu Asn Leu
        435                 440                 445

Ser Ser Pro His Leu Asp Asn Ile Thr Ile Asp Asp Val Pro Ala Val
450                 455                 460

Pro Ile Met Thr Leu Glu Ser His Arg Gly Tyr Gln Gly Thr Trp Glu
465                 470                 475                 480

Ile Ser Trp Lys Glu Gln Pro Lys Leu Thr Phe Gly Lys Ala Thr Ile
                485                 490                 495

Ala Pro Asn Lys Gln Met His Leu Ile Trp Lys Pro Ser Gly Tyr Val
            500                 505                 510

Pro Phe Ser Gly Gly Thr Gly Glu Phe Thr Thr Ser Leu Val Pro Asn
        515                 520                 525

Ser Leu Trp Asn Leu Phe Leu Asp Thr Arg Phe Ser Gln Gln Ala Ile
```

```
                 530                 535                 540
Glu Lys His Ala Val Ser Ser Gly Asn Gly Ile Trp Ile Ser Ser Met
545                 550                 555                 560

Thr Asn Ser Phe Leu Gln Gly Ser Thr Asn Asn His Gly Phe Arg
                565                 570                 575

His Lys Ser Ser Gly Tyr Thr Ala Gly Gly Lys Ile Gln Thr Leu Gln
                580                 585                 590

Asp Asp Ile Phe Ser Val Ser Phe Ser Gln Leu Phe Gly Arg Ser Lys
                595                 600                 605

Asp Phe Gly Ser Ala Thr Ser Lys Asp Thr Phe Leu Ser Gly Ser Ile
610                 615                 620

Tyr Ala Gln His Ser Arg Arg Leu Leu Pro Ile Met Arg Phe Leu Ala
625                 630                 635                 640

Gly Thr Ser Thr Tyr Arg Pro Arg Leu Leu Leu Ser Ile Pro Lys Asn
                645                 650                 655

Leu Pro Ile Asn Phe Asp Val Leu Val Ser Tyr Ser Tyr Asp Ser Asn
                660                 665                 670

His Met Lys Val Gln Lys Phe
                675

<210> SEQ ID NO 54
<211> LENGTH: 487
<212> TYPE: DNA
<213> ORGANISM: Chlamydia psittaci

<400> SEQUENCE: 54
acctcgagag aggattctct tagtgtggct ttctgtcagt tatttgcaaa agataaagac      60
taccttgtaa gcaagaacgc cgcaaacgtc tatgcgggtt ctgtatatta tcagcatgtg     120
agcaagtttg atgatctcac gcggttattt aatgggccta acacgtgttg ttcagggttt     180
tctaaagaga ttcctatttt cttggatgca caaattacct attgccacac ggccaacaac     240
atgacaacgt cctatacaga ctatcctgaa gtgaaaggtt cttggggtaa tgatacctg      300 ggcttaactt tgtctactag cgtacctatc ccggtattta gttcttctat ctttgatagt     360
tatgcaccgt ttgcaaaatt acaagttgtc tatgcgcacc aagatgactt taaagaacca     420
acaacagaag gccgggtctt tgaaagcagc gatcttctca acgtttctgt acctataggt     480
ataaaat                                                               487

<210> SEQ ID NO 55
<211> LENGTH: 162
<212> TYPE: PRT
<213> ORGANISM: Chlamydia psittaci

<400> SEQUENCE: 55

Thr Ser Arg Glu Asp Ser Leu Ser Val Ala Phe Cys Gln Leu Phe Ala
1               5                   10                  15

Lys Asp Lys Asp Tyr Leu Val Ser Lys Asn Ala Ala Asn Val Tyr Ala
                20                  25                  30

Gly Ser Val Tyr Tyr Gln His Val Ser Lys Phe Asp Asp Leu Thr Arg
                35                  40                  45

Leu Phe Asn Gly Pro Asn Thr Cys Cys Ser Gly Phe Ser Lys Glu Ile
            50                  55                  60

Pro Ile Phe Leu Asp Ala Gln Ile Thr Tyr Cys His Thr Ala Asn Asn
65              70                  75                  80

Met Thr Thr Ser Tyr Thr Asp Tyr Pro Glu Val Lys Gly Ser Trp Gly
                85                  90                  95
```

```
Asn Asp Thr Leu Gly Leu Thr Leu Ser Thr Ser Val Pro Ile Pro Val
            100                 105                 110

Phe Ser Ser Ser Ile Phe Asp Ser Tyr Ala Pro Phe Ala Lys Leu Gln
            115                 120                 125

Val Val Tyr Ala His Gln Asp Asp Phe Lys Glu Pro Thr Thr Glu Gly
        130                 135                 140

Arg Val Phe Glu Ser Ser Asp Leu Leu Asn Val Ser Val Pro Ile Gly
145                 150                 155                 160

Ile Lys

<210> SEQ ID NO 56
<211> LENGTH: 2781
<212> TYPE: DNA
<213> ORGANISM: Chlamydia psittaci

<400> SEQUENCE: 56
atgaggcctt ctttatataa gattttaata tcgtcgacgc tgacgttacc aatatctttt      60
cacttctcgc aattgcatgc agaagtggct ttaactcaag aatctattct cgatgcaaat     120
ggagcattca gtccgcaatc tacaagcact gcggaggaa cgatttacaa cgtcgagagt      180
gatatttcta ttgtagatgt aggacagaca gcggctcttg cttcctcagc ttttgttcag     240
actgcagaca acctaacttt caaagggaac aaccatagct tatccataac gaacgcgaat    300
gccggagcta atcctgcggg aattaacgtt aacactgccg ataagattct tacgctgaca    360
gattttctta gttgagctt taaggaatgc ccatcttctc tagtgaatac tggaaaaggg    420
gctatgaaat ccggaggagc attaaactta gcgaataatg ccagtattct gtttgatcag    480
aactattccg ctgagaatgg tggagccatc tcttgcaaag cttttctct aaccggctcg     540 agcaaagaaa tcagcttcac cactaactct actgcgaaaa aggtggagc gattgctgct    600 acgggaatag ctcatctttc ggacaaccaa ggcacaatca gatttctgg aacactgct    660 gtgaattctg ggggagcagt atattcagaa gcttctatga cgattgcagg taacaaccac    720
gttgctttta gcaacaatgc tgtttccggt tcatctgatg gttgcggtgg agctatccat    780
tgtagcaaaa caggttcagc accgacccttc actataagag ataacaaagt cttgattttt    840
gaggaaaata cttcttcagc aaaaggtgga gcgatttaca ccgataaact catattgact    900
tctggtgggc ctacggcatt tatcaataac aaagttaccc atgctacacc taagggtgga    960
gctattggta ttgctgccaa tggagaatgt agcttaaccg ctgaacatgg ggatattact   1020
tttgataata acctgatggc cacacaagac aatgctacaa taaaagaaa tgccattaac   1080 attgaaggca atggtaaatt cgtcaactta cgtgcagcgt ctggaaagac gatttctttc   1140
tatgatccta tcacagttga aggtaatgct gctgatcttc tcactttgaa taaagctgag   1200
ggtgataaaa cgtataatgg aagaattatt ttttcaggag aaaagctcac tgaagaacaa   1260
gctgctgttg cggataacct aaagacaaca tttacacagc ctatcacttt agctgctggt   1320
gaacttgtgt tacgcagcgg tgtggaagta gaagcaaaaa cagtcgtgca acagcagga   1380 tctttgattc tgatggatgc aggcacaaag ttatccgcaa aaacagaaga tgctacactg   1440
acgaatctgg ctattaatcc gaataccta gatgggaaaa aattcgccgt agtcgatgcc   1500
gttgctgctg gaagaatgt gactttatca ggtgctattg cgttattga tcctacaggg   1560 aagtttatg aaaaccataa gctaaatgat acgttagctt taggaggaat tcaactttct   1620
gggaaaggtt cggtgacaac aaccaacgtg cctagtcatg ttgttggtgt tgctgaaacc   1680
cactatggtt atcaaggaaa ctggtctgtc agttgggtca agataataa ctctgatcct   1740
```

```
aaaacacaaa cagcaatctt tacctggaat aaaacaggat atgttccaaa tcctgaacgt   1800
cgtgctccgc tagtactcaa tagcctttgg ggatccttta tagatttacg ttctattcaa   1860
gatgtcttgg aacgtagtgt tgatagtatt cttgagacac gtcgtggttt gtgggtctct   1920
ggaattggga acttcttcca taaagatcgg aatgctgaaa atcgcaaatt ccgtcatatc   1980
agttcgggat atgtgttagg agccacaaca aatacctcga gagaggattc tcttagtgtg   2040
gctttctgtc agttatttgc aaaagataaa gactaccttg taagcaagaa cgccgcaaac   2100
gtctatgcgg gttctgtata ttatcagcat gtgagcaagt ttgatgatct cacgcggtta   2160
tttaatgggc ctaacacgtg ttgttcaggg ttttctaaag agattcctat tttcttggat   2220
gcacaaatta cctattgcca cacggccaac aacatgacaa cgtcctatac agactatcct   2280
gaagtgaaag gttcttgggg taatgatacc ctgggcttaa ctttgtctac tagcgtacct   2340
atcccggtat ttagttcttc tatctttgat agttatgcac cgtttgcaaa attacaagtt   2400
gtctatgcgc accaagatga ctttaaagaa ccaacaacag aaggccgggt ctttgaaagc   2460
agcgatcttc tcaacgtttc tgtacctata ggtataaaat ttgagaaact ctcctatgga   2520
gagagaagtg cttatgatct tacactgatg tatatacctg atgtgtaccg tcataatcca   2580
agctgtatga caggattggc gatcaatgac gtttcctggt taaccacagc tacgaatctt   2640
gctagacaag ctttcatagt tcgcgcgggt aaccatattg ccttaacctc tggtgttgag   2700
atgttcagtc agtttggttt cgaattacga agctcttcaa gaaattataa cgtagatctt   2760
ggcgctaagg tcgcgttcta a                                               2781
```

<210> SEQ ID NO 57
<211> LENGTH: 926
<212> TYPE: PRT
<213> ORGANISM: Chlamydia psittaci

<400> SEQUENCE: 57

```
Met Arg Pro Ser Leu Tyr Lys Ile Leu Ile Ser Ser Thr Leu Thr Leu
1               5                   10                  15

Pro Ile Ser Phe His Phe Ser Gln Leu His Ala Glu Val Ala Leu Thr
            20                  25                  30

Gln Glu Ser Ile Leu Asp Ala Asn Gly Ala Phe Ser Pro Gln Ser Thr
        35                  40                  45

Ser Thr Ala Gly Gly Thr Ile Tyr Asn Val Glu Ser Asp Ile Ser Ile
    50                  55                  60

Val Asp Val Gly Gln Thr Ala Ala Leu Ala Ser Ser Ala Phe Val Gln
65                  70                  75                  80

Thr Ala Asp Asn Leu Thr Phe Lys Gly Asn Asn His Ser Leu Ser Ile
                85                  90                  95

Thr Asn Ala Asn Ala Gly Ala Asn Pro Ala Gly Ile Asn Val Asn Thr
            100                 105                 110

Ala Asp Lys Ile Leu Thr Leu Thr Asp Phe Ser Lys Leu Ser Phe Lys
        115                 120                 125

Glu Cys Pro Ser Ser Leu Val Asn Thr Gly Lys Gly Ala Met Lys Ser
    130                 135                 140

Gly Gly Ala Leu Asn Leu Ala Asn Asn Ala Ser Ile Leu Phe Asp Gln
145                 150                 155                 160

Asn Tyr Ser Ala Glu Asn Gly Gly Ala Ile Ser Cys Lys Ala Phe Ser
                165                 170                 175

Leu Thr Gly Ser Ser Lys Glu Ile Ser Phe Thr Thr Asn Ser Thr Ala
            180                 185                 190
```

-continued

Lys Lys Gly Gly Ala Ile Ala Ala Thr Gly Ile Ala His Leu Ser Asp
            195                 200                 205

Asn Gln Gly Thr Ile Arg Phe Ser Gly Asn Thr Ala Val Asn Ser Gly
        210                 215                 220

Gly Ala Val Tyr Ser Glu Ala Ser Met Thr Ile Ala Gly Asn Asn His
225                 230                 235                 240

Val Ala Phe Ser Asn Asn Ala Val Ser Gly Ser Asp Gly Cys Gly
                245                 250                 255

Gly Ala Ile His Cys Ser Lys Thr Gly Ser Ala Pro Thr Leu Thr Ile
                260                 265                 270

Arg Asp Asn Lys Val Leu Ile Phe Glu Glu Asn Thr Ser Ser Ala Lys
            275                 280                 285

Gly Gly Ala Ile Tyr Thr Asp Lys Leu Ile Leu Thr Ser Gly Gly Pro
        290                 295                 300

Thr Ala Phe Ile Asn Asn Lys Val Thr His Ala Thr Pro Lys Gly Gly
305                 310                 315                 320

Ala Ile Gly Ile Ala Ala Asn Gly Glu Cys Ser Leu Thr Ala Glu His
                325                 330                 335

Gly Asp Ile Thr Phe Asp Asn Asn Leu Met Ala Thr Gln Asp Asn Ala
            340                 345                 350

Thr Ile Lys Arg Asn Ala Ile Asn Ile Glu Gly Asn Gly Lys Phe Val
        355                 360                 365

Asn Leu Arg Ala Ala Ser Gly Lys Thr Ile Ser Phe Tyr Asp Pro Ile
    370                 375                 380

Thr Val Glu Gly Asn Ala Ala Asp Leu Leu Thr Leu Asn Lys Ala Glu
385                 390                 395                 400

Gly Asp Lys Thr Tyr Asn Gly Arg Ile Ile Phe Ser Gly Glu Lys Leu
                405                 410                 415

Thr Glu Glu Gln Ala Ala Val Ala Asp Asn Leu Lys Thr Thr Phe Thr
            420                 425                 430

Gln Pro Ile Thr Leu Ala Ala Gly Glu Leu Val Leu Arg Ser Gly Val
        435                 440                 445

Glu Val Glu Ala Lys Thr Val Val Gln Thr Ala Gly Ser Leu Ile Leu
    450                 455                 460

Met Asp Ala Gly Thr Lys Leu Ser Ala Lys Thr Glu Asp Ala Thr Leu
465                 470                 475                 480

Thr Asn Leu Ala Ile Asn Pro Asn Thr Leu Asp Gly Lys Lys Phe Ala
                485                 490                 495

Val Val Asp Ala Val Ala Ala Gly Lys Asn Val Thr Leu Ser Gly Ala
            500                 505                 510

Ile Gly Val Ile Asp Pro Thr Gly Lys Phe Tyr Glu Asn His Lys Leu
        515                 520                 525

Asn Asp Thr Leu Ala Leu Gly Gly Ile Gln Leu Ser Gly Lys Gly Ser
    530                 535                 540

Val Thr Thr Thr Asn Val Pro Ser His Val Val Gly Val Ala Glu Thr
545                 550                 555                 560

His Tyr Gly Tyr Gln Gly Asn Trp Ser Val Ser Trp Val Lys Asp Asn
                565                 570                 575

Asn Ser Asp Pro Lys Thr Gln Thr Ala Ile Phe Thr Trp Asn Lys Thr
            580                 585                 590

Gly Tyr Val Pro Asn Pro Glu Arg Arg Ala Pro Leu Val Leu Asn Ser
        595                 600                 605

Leu Trp Gly Ser Phe Ile Asp Leu Arg Ser Ile Gln Asp Val Leu Glu

```
                  610             615             620
Arg Ser Val Asp Ser Ile Leu Glu Thr Arg Arg Gly Leu Trp Val Ser
625                 630                 635                 640

Gly Ile Gly Asn Phe Phe His Lys Asp Arg Asn Ala Glu Asn Arg Lys
                    645                 650                 655

Phe Arg His Ile Ser Ser Gly Tyr Val Leu Gly Ala Thr Thr Asn Thr
                660                 665                 670

Ser Arg Glu Asp Ser Leu Ser Val Ala Phe Cys Gln Leu Phe Ala Lys
                675                 680                 685

Asp Lys Asp Tyr Leu Val Ser Lys Asn Ala Ala Asn Val Tyr Ala Gly
690                 695                 700

Ser Val Tyr Tyr Gln His Val Ser Lys Phe Asp Leu Thr Arg Leu
705                 710                 715                 720

Phe Asn Gly Pro Asn Thr Cys Cys Ser Gly Phe Ser Lys Glu Ile Pro
                725                 730                 735

Ile Phe Leu Asp Ala Gln Ile Thr Tyr Cys His Thr Ala Asn Asn Met
                740                 745                 750

Thr Thr Ser Tyr Thr Asp Tyr Pro Glu Val Lys Gly Ser Trp Gly Asn
                755                 760                 765

Asp Thr Leu Gly Leu Thr Leu Ser Thr Ser Val Pro Ile Pro Val Phe
770                 775                 780

Ser Ser Ser Ile Phe Asp Ser Tyr Ala Pro Phe Ala Lys Leu Gln Val
785                 790                 795                 800

Val Tyr Ala His Gln Asp Asp Phe Lys Glu Pro Thr Thr Glu Gly Arg
                805                 810                 815

Val Phe Glu Ser Ser Asp Leu Leu Asn Val Ser Val Pro Ile Gly Ile
                820                 825                 830

Lys Phe Glu Lys Leu Ser Tyr Gly Glu Arg Ser Ala Tyr Asp Leu Thr
835                 840                 845

Leu Met Tyr Ile Pro Asp Val Tyr Arg His Asn Pro Ser Cys Met Thr
                850                 855                 860

Gly Leu Ala Ile Asn Asp Val Ser Trp Leu Thr Thr Ala Thr Asn Leu
865                 870                 875                 880

Ala Arg Gln Ala Phe Ile Val Arg Ala Gly Asn His Ile Ala Leu Thr
                885                 890                 895

Ser Gly Val Glu Met Phe Ser Gln Phe Gly Phe Glu Leu Arg Ser Ser
                900                 905                 910

Ser Arg Asn Tyr Asn Val Asp Leu Gly Ala Lys Val Ala Phe
                915                 920                 925

<210> SEQ ID NO 58
<211> LENGTH: 559
<212> TYPE: DNA
<213> ORGANISM: Chlamydia psittaci

<400> SEQUENCE: 58
tgtgttcatt ctttagcagg agttgcattt acgttgtttc tctgtgagca tatgtttacc    60
aatatgcttg cttcttctta ttttaaggaa ggcagtggtt tgttcagtt agtgagcaaa    120 tttcatcaga ttcctggtct gaagatcata gaaattgttt ttttagccct accgtttact    180
tgtcacgcta tcctaggtat tttctatctt tttcaagcgc aaactaattc acgggcttct    240
gacggcagaa aacccgcgtt aatctatgcg agaaatcttg cctatacttg cagagaaga    300 actgcttgga ttttactttt cggtcttatt tttcacgtag ttcagtttcg ttttcttcgt    360
tatcctattc atgtagagct gcatgggcaa acatactatg ttgtcgatat tgacgcttct    420
```

```
cggtatgcgg cgatagtgcg gggtacacaa ggattttta ctataaattt ttcagctcct    480
caacttgaaa cgattcgttt ggataaagag gatcttgacg gcagcgcagt ttctcaatta    540
ttagacagaa aagcgtatc                                                559

<210> SEQ ID NO 59
<211> LENGTH: 186
<212> TYPE: PRT
<213> ORGANISM: Chlamydia psittaci

<400> SEQUENCE: 59

Cys Val His Ser Leu Ala Gly Val Ala Phe Thr Leu Phe Leu Cys Glu
1               5                   10                  15

His Met Phe Thr Asn Met Leu Ala Ser Ser Tyr Phe Lys Glu Gly Ser
            20                  25                  30

Gly Phe Val Gln Leu Val Ser Lys Phe His Gln Ile Pro Gly Leu Lys
        35                  40                  45

Ile Ile Glu Ile Val Phe Leu Ala Leu Pro Phe Thr Cys His Ala Ile
    50                  55                  60

Leu Gly Ile Phe Tyr Leu Phe Gln Ala Gln Thr Asn Ser Arg Ala Ser
65                  70                  75                  80

Asp Gly Arg Lys Pro Ala Leu Ile Tyr Ala Arg Asn Leu Ala Tyr Thr
                85                  90                  95

Trp Gln Arg Arg Thr Ala Trp Ile Leu Leu Phe Gly Leu Ile Phe His
            100                 105                 110

Val Val Gln Phe Arg Phe Leu Arg Tyr Pro Ile His Val Glu Leu His
        115                 120                 125

Gly Gln Thr Tyr Tyr Val Val Asp Ile Asp Ala Ser Arg Tyr Ala Ala
    130                 135                 140

Ile Val Arg Gly Thr Gln Gly Phe Phe Thr Ile Asn Phe Ser Ala Pro
145                 150                 155                 160

Gln Leu Glu Thr Ile Arg Leu Asp Lys Glu Asp Leu Asp Gly Ser Ala
                165                 170                 175

Val Ser Gln Leu Leu Asp Arg Lys Ala Tyr
            180                 185

<210> SEQ ID NO 60
<211> LENGTH: 687
<212> TYPE: DNA
<213> ORGANISM: Chlamydia psittaci

<400> SEQUENCE: 60
atgatgaatg aaaaggaatc atgttctgag gctactcaga ggtcatggaa gtactacact     60
agctttgttt tacgttgtgt tcattcttta gcaggagttg catttacgtt gtttctctgt    120
gagcatatgt ttaccaatat gcttgcttct tcttatttta aggaaggcag tggttttgtt    180
cagttagtga gcaaatttca tcagattcct ggtctgaaga tcatagaaat tgttttttta    240
gccctaccgt ttacttgtca cgctatccta ggtattttct atctttttca agcgcaaact    300
aattcacggg cttctgacgg cagaaaaccc gcgttaatct atgcgagaaa tcttgcctat    360
acttggcaga gaagaactgc ttggatttta cttttcggtc ttatttttca cgtagttcag    420
tttcgttttc ttcgttatcc tattcatgta gagctgcatg ggcaaacata ctatgttgtc    480
gatattgacg cttctcggta tgcggcgata gtgcggggta cacaaggatt ttttactata    540
aatttttcag ctcctcaact tgaaacgatt cgtttggata aagaggatct tgacggcagc    600
gcagtttctc aattattaga cagaaaagcg tatctcctga ctcctaatgt tggaccgctt    660
```
ttctttatgt tgttcgggat tctttag 687

<210> SEQ ID NO 61
<211> LENGTH: 228
<212> TYPE: PRT
<213> ORGANISM: Chlamydia psittaci

<400> SEQUENCE: 61

Met Met Asn Glu Lys Glu Ser Cys Ser Glu Ala Thr Gln Arg Ser Trp
1               5                   10                  15

Lys Tyr Tyr Thr Ser Phe Val Leu Arg Cys Val His Ser Leu Ala Gly
            20                  25                  30

Val Ala Phe Thr Leu Phe Leu Cys Glu His Met Phe Thr Asn Met Leu
        35                  40                  45

Ala Ser Ser Tyr Phe Lys Glu Gly Ser Gly Phe Val Gln Leu Val Ser
    50                  55                  60

Lys Phe His Gln Ile Pro Gly Leu Lys Ile Ile Glu Ile Val Phe Leu
65                  70                  75                  80

Ala Leu Pro Phe Thr Cys His Ala Ile Leu Gly Ile Phe Tyr Leu Phe
                85                  90                  95

Gln Ala Gln Thr Asn Ser Arg Ala Ser Asp Gly Arg Lys Pro Ala Leu
            100                 105                 110

Ile Tyr Ala Arg Asn Leu Ala Tyr Thr Trp Gln Arg Thr Ala Trp
        115                 120                 125

Ile Leu Leu Phe Gly Leu Ile Phe His Val Val Gln Phe Arg Phe Leu
    130                 135                 140

Arg Tyr Pro Ile His Val Glu Leu His Gly Gln Thr Tyr Tyr Val Val
145                 150                 155                 160

Asp Ile Asp Ala Ser Arg Tyr Ala Ala Ile Val Arg Gly Thr Gln Gly
                165                 170                 175

Phe Phe Thr Ile Asn Phe Ser Ala Pro Gln Leu Glu Thr Ile Arg Leu
            180                 185                 190

Asp Lys Glu Asp Leu Asp Gly Ser Ala Val Ser Gln Leu Leu Asp Arg
        195                 200                 205

Lys Ala Tyr Leu Leu Thr Pro Asn Val Gly Pro Leu Phe Phe Met Leu
    210                 215                 220

Phe Gly Ile Leu
225

<210> SEQ ID NO 62
<211> LENGTH: 1329
<212> TYPE: DNA
<213> ORGANISM: Chlamydia psittaci

<400> SEQUENCE: 62
atgactctac aaccctacca agcatcctct agaaagtacc gtccacaaat ctttcgagaa     60
attctaggtc agagctctgt tgtcgctgta ttaaaaaatg ccttggtctt caaccgagcc    120
gcccacgcct atctattttc tggaattcgt ggtacaggga aaaccacact agctcgcatt    180
ttagcaaaag ctctgaactg cgtgcatctt agcgaggatg gcgagccctg caaccagtgt    240
ttttcttgta agagattgc ttcaggatcc tctttagacg ttttagaaat tgacggagcc    300
tcccaccgtg gtatcgaaga tatccgtcaa attaatgaaa ctgtattatt cactcctgta    360
aaagcaaagt ttaaaattta tatcatagat gaagttcata tgctcactaa ggaagccttc    420
aatgctttat tgaagacttt agaagagcct ccacaacatg taaaatttt ctttgcaact    480

```
acagaaatcc ataaaattcc cggaactatt ttaagtcgtt gtcaaaaaat gcatcttcaa    540
aggattcctg aaaaaacgat cctggagaag ctatcgctta tggctcaaga tgaccatatt    600
gaggcgtcgc aagaagcatt ggcgccgatc gcccgtgcag cacaaggaag cttgcgtgat    660
gcagaatctc tttatgacta cgtaatatct ttatttccta aatctctctc tcccgacacg    720
gttgcccaag ctttaggctt tgcttcccaa gattctctcc ggactttaga caatgcgatt    780
cttcaaaggg actatgcgac agccttaggg atcgtaacgg acttcttaaa ttctggggta    840
gcacctgtca catttctcca tgaccttaca ttatttatc gtaatcttct tcttacgaat    900
tctacaacaa gcaagttcag ctctcagtat aagacggagc agcttctaga atcatagat    960
ttccttggag aatctgctaa gcacctacaa ataccatct tcgaacagac attttagaa    1020
accgtcatca ttcatatcat tcgcatttat caaaggcctg ttttatcaga gttgatctct   1080
tctattaaga gtcggcagtt tgaagggctt cgcaatatta aggagcccac cttgacgcag   1140
caagtatcag ctcctcaacc tcagcccacc tacaaagaac agagtttttt agagaaaaaa   1200
aatcaacctg ctgcggaagg taaaattata tctgtagaag ttaaaagctc agcttcaata   1260
aaatctgcag ctgtagacac attattacag tttgctgttg tagaattttc aggaattttα   1320
agacaataa                                                            1329

<210> SEQ ID NO 63
<211> LENGTH: 442
<212> TYPE: PRT
<213> ORGANISM: Chlamydia psittaci

<400> SEQUENCE: 63

Met Thr Leu Gln Pro Tyr Gln Ala Ser Ser Arg Lys Tyr Arg Pro Gln
1               5                   10                  15

Ile Phe Arg Glu Ile Leu Gly Gln Ser Ser Val Val Ala Val Leu Lys
            20                  25                  30

Asn Ala Leu Val Phe Asn Arg Ala Ala His Ala Tyr Leu Phe Ser Gly
        35                  40                  45

Ile Arg Gly Thr Gly Lys Thr Thr Leu Ala Arg Ile Leu Ala Lys Ala
    50                  55                  60

Leu Asn Cys Val His Leu Ser Glu Asp Gly Glu Pro Cys Asn Gln Cys
65                  70                  75                  80

Phe Ser Cys Lys Glu Ile Ala Ser Gly Ser Ser Leu Asp Val Leu Glu
                85                  90                  95

Ile Asp Gly Ala Ser His Arg Gly Ile Glu Asp Ile Arg Gln Ile Asn
            100                 105                 110

Glu Thr Val Leu Phe Thr Pro Val Lys Ala Lys Phe Lys Ile Tyr Ile
        115                 120                 125

Ile Asp Glu Val His Met Leu Thr Lys Glu Ala Phe Asn Ala Leu Leu
    130                 135                 140

Lys Thr Leu Glu Glu Pro Pro Gln His Val Lys Phe Phe Ala Thr
145                 150                 155                 160

Thr Glu Ile His Lys Ile Pro Gly Thr Ile Leu Ser Arg Cys Gln Lys
                165                 170                 175

Met His Leu Gln Arg Ile Pro Glu Lys Thr Ile Leu Glu Lys Leu Ser
            180                 185                 190

Leu Met Ala Gln Asp Asp His Ile Glu Ala Ser Gln Glu Ala Leu Ala
        195                 200                 205

Pro Ile Ala Arg Ala Ala Gln Gly Ser Leu Arg Asp Ala Glu Ser Leu
    210                 215                 220
```

```
Tyr Asp Tyr Val Ile Ser Leu Phe Pro Lys Ser Leu Ser Pro Asp Thr
225                 230                 235                 240

Val Ala Gln Ala Leu Gly Phe Ala Ser Gln Asp Ser Leu Arg Thr Leu
            245                 250                 255

Asp Asn Ala Ile Leu Gln Arg Asp Tyr Ala Thr Ala Leu Gly Ile Val
        260                 265                 270

Thr Asp Phe Leu Asn Ser Gly Val Ala Pro Val Thr Phe Leu His Asp
    275                 280                 285

Leu Thr Leu Phe Tyr Arg Asn Leu Leu Thr Asn Ser Thr Thr Ser
290                 295                 300

Lys Phe Ser Ser Gln Tyr Lys Thr Glu Gln Leu Leu Glu Ile Ile Asp
305                 310                 315                 320

Phe Leu Gly Glu Ser Ala Lys His Leu Gln Asn Thr Ile Phe Glu Gln
                325                 330                 335

Thr Phe Leu Glu Thr Val Ile Ile His Ile Ile Arg Ile Tyr Gln Arg
            340                 345                 350

Pro Val Leu Ser Glu Leu Ile Ser Ser Ile Lys Ser Arg Gln Phe Glu
        355                 360                 365

Gly Leu Arg Asn Ile Lys Glu Pro Thr Leu Thr Gln Gln Val Ser Ala
    370                 375                 380

Pro Gln Pro Gln Pro Thr Tyr Lys Glu Gln Ser Phe Leu Glu Lys Lys
385                 390                 395                 400

Asn Gln Pro Ala Ala Glu Gly Lys Ile Ile Ser Val Glu Val Lys Ser
                405                 410                 415

Ser Ala Ser Ile Lys Ser Ala Ala Val Asp Thr Leu Leu Gln Phe Ala
            420                 425                 430

Val Val Glu Phe Ser Gly Ile Leu Arg Gln
        435                 440

<210> SEQ ID NO 64
<211> LENGTH: 1479
<212> TYPE: DNA
<213> ORGANISM: Chlamydia psittaci

<400> SEQUENCE: 64
atgtatcgat atagtgcttt agaattagca aaagctgtga ctttagggga actgacagcc     60 acagggtga ctcaacattt ttttcataga atagaagaag ctgaggggca ggtaggtgcc    120
tttatttcct tgtgtaagga acaagcttta gaacaggcag agctcataga taaaaagcgt    180
tcgcgtggag aacctttagg aaaactcgca ggtgttcctg taggaattaa agataatatt    240
cacgttacag gcctgaagac aacatgcgcc tctcgtgtgc tcgagaatta tcaaccaccg    300
tttgatgcta ctgttgtaga agaatcaaa aaagaagatg ggattatctt aggcaaactc    360
aatatggatg agtttgctat gggatcaaca acgctatatt ctgcttttca tcctacccac    420 aaccctggg atttatctcg tgttcctgga ggttcttcag gggatctgc ggccgcagtt    480 tctgctagat tttgtcccgt agccctagga tcagataccg aggatccat ccgtcagccc    540 gcagcatttt tgtggtgttgt aggttttaag ccttcctacg gagccgtttc gcgttacggg    600
cttgtagcct ttgcctcttc gctagatcaa atcggtcctt tagccaatac tgtagaagac    660
gtcgccctaa tgatggatgt gttttctggt agagatccta agatgcaac tcaagagag    720 ttttttccgtg attctttttat gagcaagttg tctacggagg ttcctaaagt gattggggtg    780 cctagaaacat tttagagggg actccgtgat gatattaggg agaatttctt ctcttcatta    840 gccattttg aaggagaagg aacccatctt gtggatgtgg agttggatat tctcagccac    900
```

```
gctgtatcta tatattacat tttagcatct gctgaagctg ccacgaattt agcaaggttc     960
gatggggtgc gttatggata tcgttctcct caagcgcata ccatcagcca actctacgat    1020
ctctcacgtg gagaaggatt tggcaaagag gtcatgcgca gaatcctctt agggaactat    1080
gtcttgtctg cggagagaca gaatgtttat tataagaaag ctacggcagt gcgtgctaag    1140
attgtaaaag catttagaac tgcatttgaa aagtgtgaaa tcttagccat gcccgtctgt    1200
tctagccccg cgtttgaaat aggagaaatt ctagatcctg tgactttata tctacaggat    1260
atctatactg tagctatgaa tttagcgtat cttcctgcca ttgccgtacc ctctggattt    1320
tctaaggagg gcctgccctt aggcctacag attatcggac agcaaggaca agaccaacaa    1380
gtgtgccaag tgggttacag tttccaagag catgcgcaaa ttaagcaatt gttttctaag    1440
agatatgcca aaagtgttgt tctaggaggt caatcatga                            1479

<210> SEQ ID NO 65
<211> LENGTH: 492
<212> TYPE: PRT
<213> ORGANISM: Chlamydia psittaci

<400> SEQUENCE: 65

Met Tyr Arg Tyr Ser Ala Leu Glu Leu Ala Lys Ala Val Thr Leu Gly
1               5                   10                  15

Glu Leu Thr Ala Thr Gly Val Thr Gln His Phe Phe His Arg Ile Glu
            20                  25                  30

Glu Ala Glu Gly Gln Val Gly Ala Phe Ile Ser Leu Cys Lys Glu Gln
        35                  40                  45

Ala Leu Glu Gln Ala Glu Leu Ile Asp Lys Lys Arg Ser Arg Gly Glu
    50                  55                  60

Pro Leu Gly Lys Leu Ala Gly Val Pro Val Gly Ile Lys Asp Asn Ile
65                  70                  75                  80

His Val Thr Gly Leu Lys Thr Thr Cys Ala Ser Arg Val Leu Glu Asn
                85                  90                  95

Tyr Gln Pro Pro Phe Asp Ala Thr Val Val Glu Arg Ile Lys Lys Glu
            100                 105                 110

Asp Gly Ile Ile Leu Gly Lys Leu Asn Met Asp Glu Phe Ala Met Gly
        115                 120                 125

Ser Thr Thr Leu Tyr Ser Ala Phe His Pro Thr His Asn Pro Trp Asp
    130                 135                 140

Leu Ser Arg Val Pro Gly Gly Ser Ser Gly Gly Ser Ala Ala Ala Val
145                 150                 155                 160

Ser Ala Arg Phe Cys Pro Val Ala Leu Gly Ser Asp Thr Gly Gly Ser
                165                 170                 175

Ile Arg Gln Pro Ala Ala Phe Cys Gly Val Val Gly Phe Lys Pro Ser
            180                 185                 190

Tyr Gly Ala Val Ser Arg Tyr Gly Leu Val Ala Phe Ala Ser Ser Leu
        195                 200                 205

Asp Gln Ile Gly Pro Leu Ala Asn Thr Val Glu Asp Val Ala Leu Met
    210                 215                 220

Met Asp Val Phe Ser Gly Arg Asp Pro Lys Asp Ala Thr Ser Arg Glu
225                 230                 235                 240

Phe Phe Arg Asp Ser Phe Met Ser Lys Leu Ser Thr Glu Val Pro Lys
                245                 250                 255

Val Ile Gly Val Pro Arg Thr Phe Leu Glu Gly Leu Arg Asp Asp Ile
            260                 265                 270

Arg Glu Asn Phe Phe Ser Ser Leu Ala Ile Phe Glu Gly Glu Gly Thr
```

|  |  |  | 275 |  |  |  | 280 |  |  |  | 285 |  |
|---|---|---|---|---|---|---|---|---|---|---|---|---|

His Leu Val Asp Val Glu Leu Asp Ile Leu Ser His Ala Val Ser Ile
                        290                 295                 300

Tyr Tyr Ile Leu Ala Ser Ala Glu Ala Ala Thr Asn Leu Ala Arg Phe
305                 310                 315                 320

Asp Gly Val Arg Tyr Gly Tyr Arg Ser Pro Gln Ala His Thr Ile Ser
                325                 330                 335

Gln Leu Tyr Asp Leu Ser Arg Gly Glu Gly Phe Gly Lys Glu Val Met
            340                 345                 350

Arg Arg Ile Leu Leu Gly Asn Tyr Val Leu Ser Ala Glu Arg Gln Asn
            355                 360                 365

Val Tyr Tyr Lys Lys Ala Thr Ala Val Arg Ala Lys Ile Val Lys Ala
        370                 375                 380

Phe Arg Thr Ala Phe Glu Lys Cys Glu Ile Leu Ala Met Pro Val Cys
385                 390                 395                 400

Ser Ser Pro Ala Phe Glu Ile Gly Glu Ile Leu Asp Pro Val Thr Leu
                405                 410                 415

Tyr Leu Gln Asp Ile Tyr Thr Val Ala Met Asn Leu Ala Tyr Leu Pro
            420                 425                 430

Ala Ile Ala Val Pro Ser Gly Phe Ser Lys Glu Gly Leu Pro Leu Gly
        435                 440                 445

Leu Gln Ile Ile Gly Gln Gln Gly Gln Asp Gln Gln Val Cys Gln Val
        450                 455                 460

Gly Tyr Ser Phe Gln Glu His Ala Gln Ile Lys Gln Leu Phe Ser Lys
465                 470                 475                 480

Arg Tyr Ala Lys Ser Val Val Leu Gly Gly Gln Ser
                485                 490

<210> SEQ ID NO 66
<211> LENGTH: 1962
<212> TYPE: DNA
<213> ORGANISM: Chlamydia psittaci

<400> SEQUENCE: 66

```
atgagctacc gtaaacgttc gactctaatt gttctaggag tgtttgctct ttatgctctt      60
ctagtattgc gttattataa aattcaaatt tgtgaaggag accactgggc cgcagaagct     120
ctcgggcaac acgaattttg tgtccgtgat ccttttcgaa ggggcacctt ttttgctaac     180
acgacagtac gtaagggaga caaagacctt cagcagcctt cgctgtcga tattacaaaa      240
tttcaccttt gtgcagatcc tttagctatt cccgaatgtc atcgtgatga gatcatccaa     300
gggattctcc aatttattga ggggcagacc tacgacgacc tctccctaaa gttagataag     360
aaatctcggt attgtaagct gtatccttta ttagatgttt ctgtccatga ccggctatcc     420
ctttggtgga aggatatgc aacaaagcat cgcttaccaa caaacgccct atttttatt      480
acggactacc aacgctcgta tccttttggg aagctccttg acaagttct ccataccta      540
agagaaatta aggatgagaa acaggaaaa gcctttccca caggcgggat ggaggcgtac     600
tttaatcata ttctggaagg ggacgttgga gagagaaagc tgttgcgttc tccttttgaac     660
cgtttagata cgaatcgtgt tatcaaactg cctaaagatg gctctgatat ctaccttacg     720
atcaatcctg tgatccagac cattgcagag gaagaactcg aacggggcgt gctagaagct     780
aaagcccagg gggtaggct cattctaatg aactcccaaa caggagagat tcttgcactg     840
gctcaatatc cgtttttcga tcccacaat tataaggaat acttcaataa caaagagcgc     900
atcgaacata cgaaggtatc ttttgtgagc gatgtttttg aacccgggtc gatcatgaaa     960
```

-continued

```
cctttgactg tggcgattgc tttacaagct aacgaagagg ctagcttaaa atcgcagaaa      1020 aagattttg atcctgaaga acctatcgat gtgaccagga cactcttccc tggacgaaaa       1080
ggatctccgc ttaaggatat ttctagaaac tctcaattga atatgtacat ggctatccag      1140
aaatcttcga atgtctatgt agctcagctg gctgaccgca tcatacaatc tttaggagtg      1200
gcctggtacc aacagaagtt gctagctctg ggatttggaa gaaaaacagg gatcgagctt      1260
cccagtgagg cctctggttt ggtgccttct ccccatcgtt tccatattaa tggttccctg      1320
gaatggtcct tatctactcc atattctttg gctatgggat ataatatttt ggcaacaggg      1380
atacaaatgg ttcaagccta cgctatcctt gcaaacggag gttatgccgt ccggcccact      1440
ttagtaaaaa agatcgtctc tgcttcagga gaggaatatc atcttcctac taaagagaag      1500
acacgactct tttcagaaga aattactaga gaagttgttc gtgccatgcg ttttacaacg      1560
ttacccggag gttcgggatt tcgagcctct cctaagcatc actctagtgc tgggaaaaca      1620
ggaactacag aaaagatgat tcatggaaaa tatgataaac gccgtcatat tgcttctttt      1680
ataggtttta ctcccgtaga gagctcggag ggaaatttcc cacctttagt gatgctcgtc      1740
tccatagatg atcctgaata tggtttgcga gccgacggca cgaaaaatta tatgggggg       1800 cgttgtgcgg cacccatttt ttctagggtt gctgaccgca cactcctcta tttagggatt      1860
cttccagaca agaagctaag aaattgcgac gaagaagctg ctgcattaaa gcgtctctat      1920
gaagaatgga atcgttctcc gaaacaaggg ggaacgaggt ga                         1962
```

<210> SEQ ID NO 67
<211> LENGTH: 653
<212> TYPE: PRT
<213> ORGANISM: Chlamydia psittaci

<400> SEQUENCE: 67

```
Met Ser Tyr Arg Lys Arg Ser Thr Leu Ile Val Leu Gly Val Phe Ala
1               5                   10                  15

Leu Tyr Ala Leu Leu Val Leu Arg Tyr Tyr Lys Ile Gln Ile Cys Glu
            20                  25                  30

Gly Asp His Trp Ala Ala Glu Ala Leu Gly Gln His Glu Phe Cys Val
        35                  40                  45

Arg Asp Pro Phe Arg Arg Gly Thr Phe Phe Ala Asn Thr Thr Val Arg
    50                  55                  60

Lys Gly Asp Lys Asp Leu Gln Gln Pro Phe Ala Val Asp Ile Thr Lys
65                  70                  75                  80

Phe His Leu Cys Ala Asp Pro Leu Ala Ile Pro Glu Cys His Arg Asp
                85                  90                  95

Glu Ile Ile Gln Gly Ile Leu Gln Phe Ile Glu Gly Thr Tyr Asp
            100                 105                 110

Asp Leu Ser Leu Lys Leu Asp Lys Lys Ser Arg Tyr Cys Lys Leu Tyr
        115                 120                 125

Pro Leu Leu Asp Val Ser Val His Asp Arg Leu Ser Leu Trp Trp Lys
    130                 135                 140

Gly Tyr Ala Thr Lys His Arg Leu Pro Thr Asn Ala Leu Phe Phe Ile
145                 150                 155                 160

Thr Asp Tyr Gln Arg Ser Tyr Pro Phe Gly Lys Leu Leu Gly Gln Val
                165                 170                 175

Leu His Thr Leu Arg Glu Ile Lys Asp Glu Lys Thr Gly Lys Ala Phe
            180                 185                 190

Pro Thr Gly Gly Met Glu Ala Tyr Phe Asn His Ile Leu Glu Gly Asp
```

```
              195                 200                 205
Val Gly Glu Arg Lys Leu Leu Arg Ser Pro Leu Asn Arg Leu Asp Thr
210                 215                 220

Asn Arg Val Ile Lys Leu Pro Lys Asp Gly Ser Asp Ile Tyr Leu Thr
225                 230                 235                 240

Ile Asn Pro Val Ile Gln Thr Ile Ala Glu Glu Leu Glu Arg Gly
                245                 250                 255

Val Leu Glu Ala Lys Ala Gln Gly Gly Arg Leu Ile Leu Met Asn Ser
                260                 265                 270

Gln Thr Gly Glu Ile Leu Ala Leu Ala Gln Tyr Pro Phe Phe Asp Pro
                275                 280                 285

Thr Asn Tyr Lys Glu Tyr Phe Asn Asn Lys Glu Arg Ile Glu His Thr
                290                 295                 300

Lys Val Ser Phe Val Ser Asp Val Phe Glu Pro Gly Ser Ile Met Lys
305                 310                 315                 320

Pro Leu Thr Val Ala Ile Ala Leu Gln Ala Asn Glu Glu Ala Ser Leu
                325                 330                 335

Lys Ser Gln Lys Lys Ile Phe Asp Pro Glu Pro Ile Asp Val Thr
                340                 345                 350

Arg Thr Leu Phe Pro Gly Arg Lys Gly Ser Pro Leu Lys Asp Ile Ser
                355                 360                 365

Arg Asn Ser Gln Leu Asn Met Tyr Met Ala Ile Gln Lys Ser Ser Asn
                370                 375                 380

Val Tyr Val Ala Gln Leu Ala Asp Arg Ile Ile Gln Ser Leu Gly Val
385                 390                 395                 400

Ala Trp Tyr Gln Gln Lys Leu Leu Ala Leu Gly Phe Gly Arg Lys Thr
                405                 410                 415

Gly Ile Glu Leu Pro Ser Glu Ala Ser Gly Leu Val Pro Ser Pro His
                420                 425                 430

Arg Phe His Ile Asn Gly Ser Leu Glu Trp Ser Leu Ser Thr Pro Tyr
                435                 440                 445

Ser Leu Ala Met Gly Tyr Asn Ile Leu Ala Thr Gly Ile Gln Met Val
450                 455                 460

Gln Ala Tyr Ala Ile Leu Ala Asn Gly Gly Tyr Ala Val Arg Pro Thr
465                 470                 475                 480

Leu Val Lys Lys Ile Val Ser Ala Ser Gly Glu Glu Tyr His Leu Pro
                485                 490                 495

Thr Lys Glu Lys Thr Arg Leu Phe Ser Glu Glu Ile Thr Arg Glu Val
                500                 505                 510

Val Arg Ala Met Arg Phe Thr Thr Leu Pro Gly Gly Ser Gly Phe Arg
515                 520                 525

Ala Ser Pro Lys His His Ser Ser Ala Gly Lys Thr Gly Thr Thr Glu
530                 535                 540

Lys Met Ile His Gly Lys Tyr Asp Lys Arg His Ile Ala Ser Phe
545                 550                 555                 560

Ile Gly Phe Thr Pro Val Glu Ser Ser Glu Gly Asn Phe Pro Pro Leu
                565                 570                 575

Val Met Leu Val Ser Ile Asp Asp Pro Glu Tyr Gly Leu Arg Ala Asp
                580                 585                 590

Gly Thr Lys Asn Tyr Met Gly Gly Arg Cys Ala Ala Pro Ile Phe Ser
                595                 600                 605

Arg Val Ala Asp Arg Thr Leu Leu Tyr Leu Gly Ile Leu Pro Asp Lys
610                 615                 620
```

Lys Leu Arg Asn Cys Asp Glu Glu Ala Ala Ala Leu Lys Arg Leu Tyr
625 630 635 640

Glu Glu Trp Asn Arg Ser Pro Lys Gln Gly Gly Thr Arg
645 650

<210> SEQ ID NO 68
<211> LENGTH: 819
<212> TYPE: DNA
<213> ORGANISM: Chlamydia psittaci

<400> SEQUENCE: 68
atgaaaaaaa aattatcatt acttgtaggt ttaatttttg ttttgagttc ttgccataag 60
gaagatgctc agaataaaat acgtattgta gccagtccga cacctcatgc ggaattattg 120
gagagtttac aggaagaggc taaagatctt ggaatcaagc tgaaaatact tccagtagat 180
gattatcgta ttcctaatcg tttgcttttg gataaacaag tagatgcaaa ttactttcaa 240
catcaagctt ttcttgatga cgaatgcgag cgttatgatt gtaagggtga attagttgtt 300
atcgctaaag ttcatttgga acctcaagca atttattcta agaaacattc ttctttagag 360
cgcttaaaaa gccagaagaa actgactata gcgattcctg tggatcgtac gaatgctcag 420
cgtgctctac acttgttaga agagtgcgga ctcattgttt gcaaagggcc tgctaattta 480
aatatgacag ctaaagatgt ctgtgggaaa gaaaatagaa gtatcaacat attagaggtg 540
tcagctcctc ttcttgtcgg atctcttcct gacgttgatg ctgctgtcat tcctggaaat 600
tttgctatag cagcaaacct ttctccaaag aaagatagtc tttgtttaga ggatctttcg 660
gtatctaagt atacaaacct tgttgtcatt cgttctgaag acgtaggttc tcctaaaatg 720
ataaaattac agaagctgtt tcaatctcct tctgtacaac atttttttga tacaaaatat 780
catgggaata ttttgacaat gactcaagac aatggttag 819

<210> SEQ ID NO 69
<211> LENGTH: 272
<212> TYPE: PRT
<213> ORGANISM: Chlamydia psittaci

<400> SEQUENCE: 69

Met Lys Lys Lys Leu Ser Leu Leu Val Gly Leu Ile Phe Val Leu Ser
1 5 10 15

Ser Cys His Lys Glu Asp Ala Gln Asn Lys Ile Arg Ile Val Ala Ser
20 25 30

Pro Thr Pro His Ala Glu Leu Leu Glu Ser Leu Gln Glu Glu Ala Lys
35 40 45

Asp Leu Gly Ile Lys Leu Lys Ile Leu Pro Val Asp Asp Tyr Arg Ile
50 55 60

Pro Asn Arg Leu Leu Leu Asp Lys Gln Val Asp Ala Asn Tyr Phe Gln
65 70 75 80

His Gln Ala Phe Leu Asp Asp Glu Cys Glu Arg Tyr Asp Cys Lys Gly
85 90 95

Glu Leu Val Val Ile Ala Lys Val His Leu Glu Pro Gln Ala Ile Tyr
100 105 110

Ser Lys Lys His Ser Ser Leu Glu Arg Leu Lys Ser Gln Lys Lys Leu
115 120 125

Thr Ile Ala Ile Pro Val Asp Arg Thr Asn Ala Gln Arg Ala Leu His
130 135 140

Leu Leu Glu Glu Cys Gly Leu Ile Val Cys Lys Gly Pro Ala Asn Leu
145 150 155 160

```
Asn Met Thr Ala Lys Asp Val Cys Gly Lys Glu Asn Arg Ser Ile Asn
            165             170             175

Ile Leu Glu Val Ser Ala Pro Leu Leu Val Gly Ser Leu Pro Asp Val
            180             185             190

Asp Ala Ala Val Ile Pro Gly Asn Phe Ala Ile Ala Ala Asn Leu Ser
        195             200             205

Pro Lys Lys Asp Ser Leu Cys Leu Glu Asp Leu Ser Val Ser Lys Tyr
        210             215             220

Thr Asn Leu Val Val Ile Arg Ser Glu Asp Val Gly Ser Pro Lys Met
225             230             235             240

Ile Lys Leu Gln Lys Leu Phe Gln Ser Pro Ser Val Gln His Phe Phe
            245             250             255

Asp Thr Lys Tyr His Gly Asn Ile Leu Thr Met Thr Gln Asp Asn Gly
            260             265             270
```